United States Patent [19]
Foulkes et al.

[11] Patent Number: 6,165,712
[45] Date of Patent: *Dec. 26, 2000

[54] METHODS OF TRANSCRIPTIONALLY MODULATING EXPRESSION OF VIRAL GENES AND GENES USEFUL FOR PRODUCTION OF PROTEINS

[75] Inventors: J. Gordon Foulkes, Huntington Station; Franz E. Leichtfried, Bellerose; Christian Pieler, Westbury; John R. Stephenson, Rockville Center; Casey C. Case, Linbrook, all of N.Y.

[73] Assignee: OSI Pharmaceuticals, Inc., Uniondale, N.Y.

[*] Notice: This patent is subject to a terminal disclaimer.

[21] Appl. No.: 08/463,691

[22] Filed: Jun. 5, 1995

Related U.S. Application Data

[62] Division of application No. 08/255,236, Jun. 7, 1994, which is a continuation of application No. 07/644,233, Jan. 18, 1991, abandoned, which is a continuation-in-part of application No. 07/555,196, Jul. 18, 1990, abandoned, which is a continuation-in-part of application No. 07/382,712, Jul. 18, 1989, abandoned.

[51] Int. Cl.$^7$ .............................. C12Q 1/68; C12N 15/09
[52] U.S. Cl. .............................. 435/6; 435/440; 435/455; 435/471; 435/475; 435/325; 435/252.3; 435/252.33; 435/254.11; 435/4; 435/69.1; 435/320.1; 536/24.1
[58] Field of Search ................... 435/4, 6, 69.1, 435/172.3, 240.2, 252.3, 254.11, 320.1, 440, 455, 471, 475, 325; 536/24.1; 935/36, 39, 43, 77, 79

[56] References Cited

U.S. PATENT DOCUMENTS

| | | | |
|---|---|---|---|
| 4,535,058 | 8/1985 | Weinberg et al. | 435/6 |
| 4,601,978 | 7/1986 | Karin | 435/69.1 |
| 4,699,877 | 10/1987 | Cline et al. | 424/138.1 |
| 4,736,866 | 4/1988 | Leder et al. | 800/2 |
| 4,738,922 | 4/1988 | Haseltine et al. | 435/69.3 |
| 4,740,461 | 4/1988 | Kaufman | 435/172.3 |
| 4,740,463 | 4/1988 | Weinberg et al. | 435/172.3 |
| 4,761,367 | 8/1988 | Edgell et al. | 435/6 |
| 4,761,371 | 8/1988 | Bell et al. | 435/69.1 |
| 4,774,182 | 9/1988 | Szybalski | 435/69.1 |
| 4,806,463 | 2/1989 | Goodchild et al. | 435/5 |
| 4,827,079 | 5/1989 | Evans et al. | 800/2 |
| 4,861,709 | 8/1989 | Ulitzer et al. | 435/6 |
| 4,885,238 | 12/1989 | Reddel et al. | 435/29 |
| 4,935,363 | 6/1990 | Brown et al. | 435/172.3 |
| 4,981,783 | 1/1991 | Augenlicht | 435/6 |
| 4,981,790 | 1/1991 | Haseltine et al. | 435/69.1 |
| 5,070,012 | 12/1991 | Nolan et al. | 435/6 |

(List continued on next page.)

FOREIGN PATENT DOCUMENTS

| | | |
|---|---|---|
| 117058 | 8/1984 | European Pat. Off. . |
| 332104 | 9/1989 | European Pat. Off. . |
| WO8902472 | 5/1989 | WIPO . |

OTHER PUBLICATIONS

S.T. Crooke. "Basic Principles of Antisense Therapeutics". in Antisense Research and Application. New York :Springer–Verlag. pp. 1–50, 1998.

Ringold et al. "Glucocorticoid stimulated accumulation of mouse mammary tumor virus RNA: Increased rate of synthesis of viral RNA." Proc. Nat. Acad. Sci., USA 74 (7):2879–2883, Jul. 1977.

Ritzi et al. "Glucocorticoids stimulate the release of a viral tumor marker (MMTV gp52) while inhibiting tumor cell growth" J. steroid Biochem. 32(4):499–505, Apr. 1989.

Ucker et al. "Glucocorticoids and chromosomal position modulate murine mammary tumor virus transcription by affecting efficiency of promoter utilization." Mol. Cell. Biology 3(4): 551–561, Apr. 1983.

Cripe et al.. Transcriptional regulation of the human papillomavirus–16– E6–E7 promoter by a keratinocyte dependent enhancer and by viral E2 transactivator and repressor gene products:implications for cervical carcinogenesis. EMBO J. 6(12): 3745–3753, 1987.

Davis et al. Immediate–early gene region of human cytomegalovirus trans–activates the promoter of human immunodeficiency virus. Proc. Nat. Acad. Sci., USA, 84(23): 8642–8646, Dec. 1987.

Mosca et al. Activation of human immunodeficiency virus by herpesvirus infection: Identification of a region within the long terminal repeat that responds to a transacting factor encoded by herpes simplex virus 1. Proc. Nat. Acad. Sci., USA 84: 7408–7, Nov. 1987.

Schneider et al. Mutational analysis of the adenovirus E1a gene: the role of transcriptional regulation in transformation. EMBO J. 6(7): 2053–2060, 1987.

Paterson et al. Mutational dissection of the HSV–1 immediate early protein Vmw175 involved in transcriptoinal transactivation and repression. Virology 166 (1): 186–196, 1988.

Jordan et al. The L protein of a VSV mutant isolated from a persistent infection is responsible for viral interference and dominance over the wild type. Virology 169(1):137–141, Mar. 1989.

Lambert et al. A transciptional repressor encoded by BPV–1 shares a common carboxyterminal domain with the E2 transactivator. Cell 50(1):69–78, Jul. 3, 1987.

(List continued on next page.)

Primary Examiner—Karen Cochrane Carlson
Assistant Examiner—Gabriel E. Bugaisky
Attorney, Agent, or Firm—John P. White; Cooper & Dunham LLP

[57] ABSTRACT

The present invention provides a method of transcriptionally modulating the expression of a gene encoding a protein of interest, the expression of which gene is associated with the production in cell culture of a protein encoded by the gene, which comprises contacting a cell, which is capable of expressing the gene, with an amount of a molecule effective to transcriptionally modulate expression of the gene and thereby affect the level of the protein encoded by the gene which is expressed by the cell in culture, which molecule (a) directly transcriptionally modulates expression of the gene.

23 Claims, 29 Drawing Sheets

U.S. PATENT DOCUMENTS

| | | | |
|---|---|---|---|
| 5,071,773 | 12/1991 | Evans et al. | 436/501 |
| 5,075,229 | 12/1991 | Hanson et al. | 435/172.3 |
| 5,262,300 | 11/1993 | Evans et al. | 435/6 |
| 5,776,502 | 7/1998 | Foulkes et al. | 424/617 |

OTHER PUBLICATIONS

Uhlmann et al. Antisense Oligonucleotides: A New Therapeutic Principle, In Chemical Reviews, 90(4):544–584, 1990.

Andersen, R. et al. (1990) "Metal–Dependent Binding of A Nuclear Factor to the Rat Metallothionein–I Promoter," Nucleic Acids Research 18 (20): 6049–6055.

Angel, P. et al., (1987 A) "Phorbol Ester–Inducible Genes Contain A Common Cis Element Recognized by An TPA–Modulated Trans–Acting Factor," Cell 49: 729–739.

Angel, P. et al., (1987 B) "12–O–Tetradecanoyl–Phorbol–13–Acetate Induction of the Human Collagenase Gene Is Mediated by an Inducible Enhancer Element Located in the 5'–Flanking Region," Molecular and Cellular Biology, 7: 2256–2266.

Bickel, M. et al., (1988) "Granulocyte–Macrophage Colony–Stimulating Factor Regulation in Murine T Cells and Its Relation to Cyclosporin A," Ex. Hematol. 16: 691–695.

Blumberg, P., (1988) "Protein Kinase C as the Receptor for the Phorbol Ester Tumor Promoters: Sixth Rhoads Memorial Award Lecture," Cancer Research 48: 1–8.

Brasier, A. et al., (1989) "Optimized Use of the Firefly Luciferase Assay as a Reporter Gene in Mammalian Cell Lines," BioTechniques 7 (10): 1116–1122.

Brenner C. et al., (1989) "Message Amplification Phenotyping (Mapping): A Technique to Simultaneously Measure Multiple mRNAs from Small Numbers of Cells," BioTechniques 7 (10): 1096–1103.

Cao, T., (1989) "A Simple and Inexpensive System to Amplify DNA by PCR," BioTechniques 7 (6): 566–567.

Cohen, P. and Foulkes, J.G. eds., (1991) *The Hormonal Control of Gene Transcription*, 92–93, 235–236.

Comb, M. et al. (1986) "A Cyclic AMP– and Phorbol Ester–Inducible DNA Element," Nature 323: 353–356.

Connelly, C. et al., (1989) "The Role of Transgenic Animals in the Analysis of Various Biological Aspects of Normal and Pathologic States," Experimental Cell Research 183: 257–276.

Cybulsky, M. et al., (1991) "Gene Structure, Chromosomal Location, and Basis for Alternative mRNA Splicing of the Human VCAM1 Gene," Proc. Natl. Acad. Sci. USA 88: 7859–7863.

Das. H. et al., (1988) "Cell Type–Specific Expression of the Human ApoB Gene Is Controlled by Two Cis–Acting Regulatory Regions," Journal of Biological Chemistry 263 (23): 11452–11458.

de Wet et al., (1987) "Firefly Luciferase Gene Structure and Expression in Mammalian Cells," Molecular and Cellular Biology 7 (2): 725–737.

Emmel. E. et al., (1989) "Cyclosporin A Specifically Inhibits Function of Nuclear Proteins Involved in T Cell Activation," Science 246: 1617–1620.

Engebrecht. J. et al., (1985) "Measuring Gene Expression with Light." Science 227: 1345–1347.

Gunter. K. et al., (1989) "Cyclosporin A–Mediated Inhibition of Mitogen–Induced Gene Transcription Is Specific for the Mitogenic Stimulus and Cell Type," Journal of Immunology 142: 3286–3291.

Higuchi, K. et al., (1988) "Tissue–Specific Expression of Apolipoprotein A–I (Apo I) Is Regulated by the 5'–Flanking Region of the Human ApoA–I Gene," Journal of Biological Chemistry 263 (34): 18530–18536.

Holbrook, N. et al., (1984) "T–Cell Growth Factor: Complete Nucleotide Sequence of Organization of the Gene in Normal and Malignant Cells," Proc. Natl. Acad. Sci. USA 81: 1634–1638.

Hsu, M. et al., (1991) "Inhibition of HIV Replication in Acute and Chronic Infections in Vitro by a Tat Antagonist," Science, 254: 1799–1802.

Ishii, S. et al., (1985) "Characterization and Sequence of the Promoter Region of the Human Epidermal Growth Factor Receptor Gene," Proc. Natl. Acad. Sci. USA 82: 4920–4924.

Kaushansky, K. et al., (1985) "Genomic Cloning, Characterization, Multilineage Growth–Promoting Activity of Human Granulocyte–Macrophage Colony–Stimulating Factor," Proc. Natl. Acad. Sci. USA 83: 3101–3105.

Kawasaki, E. et al., (1985) "Molecular Cloning of a Complementary DNA Encoding Human Macrophage–Specific Colony–Stimulating Factor (CSF–1)," Science 230: 291–296.

Knott, T. et al., (1986) "Complete Protein Sequence and Identification of Structural Domains of Human Apolipoprotein B," Nature 323: 734–738.

Kronke, M. et al., (1984) "Cyclosporin A Inhibits T–Cell Growth Factor Gene Expression at the Level of mRNA Transcription," Proc. Natl. Acad. Sci. USA 81: 5214–5218.

Ladner, M. et al., (1987) "Human CSF–1: Gene Structure and Alternative splicing of mRNA Precursors," The EMBO Journal 6 (9): 2693–2698.

Lamb, P. et al., (1986) "Characterization of the Human p53 Gene," Molecular and Cellular Biology 6 (5): 1379–1385.

Lee, M–T. et al., (1990) "Differential Expression of M–CSF, G–CSF, and GM–CSF by Human Monocytes," Biol. Abstr. 89 (10): AB–100645.

Lefevre, C. et al., (1987) "Tissue–Specific Expression of the Human Growth Hormone Gene Is Conferred in Part by the Binding of a Specific Trans–Acting Factor," The EMBO Journal 6 (4): 971–981.

Lim, K. et al., (1989) "A Simple Assay for DNA Transfection by Incubation of the Cells in Culture Dishes with Substrates for Beta–Galactosidase," BioTechniques 7 (6): 576–579.

Lin, F. et al., (1985) "Cloning and Expression of the Human Erythropoietin Gene," Proc. Natl. Acad. Sci. USA 82: 7580–7584.

Majesky, M. et al., (1990) "PDGF Ligand and Receptor Gene Expression during Repair of Arterial Injury," Journal of Cell Biology 111: 2149–2158.

Maniatis, T. et al., (1987) "Regulation of Inducible and Tissue–Specific Gene Expression," Science 236: 1237–1245.

Mayo, K. et al., (1982) "Altered Regulation of the Mouse Metallothionein–I Gene Following Gene Amplification or Transfection," (in *Gene Amplification*) Schimke R.T. ed., 67–73.

McCall, C. et al., (1989) Biotherapy: A New Dimension in Cancer Treatment Bio/Technology 7: 231–240.

Metzler, D., (1977) *Biochemistry: The Chemical Reactions of Living Cells*. 116–117.

Munjaal, R. et al., (1989) "In Situ Detection of Progesterone Receptor mRNA in the Chicken Oviduct Using Probe–on Slides," BioTechniques 7 (10): 1104–1108.

Myoken, Y. et al., (1991) "Vascular Endothelial Growth Factor (VEGF) Produced by A 431 Human Epidermoid Carcinoma Cells and Identification of VEGF Membrane Binding Sites," Cell Biology 88: 5819–5823.

Nagata, S. et al., (1986) "The Chromosomal Gene Structure and Two mRNAs for Human Granulocyte Colony–Stimulating Factor," The EMBO Journal 5 (3): 575–581.

Nimer, S. et al., (1988) "Serum Cholesterol–Lowering Activity of Granulocyte–Macrophage Colony–Stimulating Factor," JAMA 260 (22): 3297–3300.

Nishizuka, Y., (1986) "Studies and Perspectives of Protein Kinase C," Science 233: 305–312.

Paul, W. (1984) *Fundamental Immunology*, 275–276.

Pons, M. et al., (1990) "A New Cellular Model of Response to Estrogens: A Bioluminescent Test to Characterize (Anti) Estrogen Molecules," BioTechniques 9 (4) 450–459.

Rao, A. et al., (1990) "A Quantitative Assay for β–D–Glucuronidase (GUS) Using Microtiter Plates," BioTechniques 8 (1): 38–40.

Ratner, M., (1989) "Can the Antisense Message Be Delivered?," Bio/Technology 7: 207.

Reisman, D. et al., (1989) "Two Promoters that Map to 5'–Sequences of the Human p53 Gene Are Differentially Regulated during Terminal Differentiation of Human Myeloid Leukemic Cells," Biol. Abstr. 88 (9): AB–673.

Rinkus, S. et al., (1980) "The Need for Both in Vitro and in Vivo Systems in Mutagenicity Screening," in *Chemical Mutagens*, de Serres et al. ed., 6: 365–473.

Roesler, W. et al., (1988) "Cyclic AMP and the Induction of Eukaryotic Gene Transcription," Journal of Biological Chemistry 263 (19): 9063–9066.

Sambrook, J. et al., (1989) "Strategies for Studying Gene Regulation," *Molecular Cloning: A Laboratory Manual*, 2nd Ed., 16.56–16.58.

Seguin, C. et al., (1987) "Regulation in Vitro of Metallothionein Gene Binding Factors," Science 235: 1383–1387.

Singleton, P. et al., (1987) Dictionary of Microbiology and Molecular Biology, p. 314 and p. 382.

Slack, J. et al., (1989) "Application of the Multiscreen System to Cytokine Radioreceptor Assays," BioTechniques 7 (10): 1132–1138.

Standaert, R. et al., (1990) "Molecular Cloning and Overexpression of the Human FK506–Binding Protein FKBP," Nature 346: 671–674.

Stanley, E. et al., (1985) "The Structure and Expression of the Murine Gene Encoding Granulocyte–Macrophage Colony Stimulating Factor: Evidence for Utilisation of Alternative Promoters," The EMBO Journal 4 (10): 2569–2573.

Stinski, M. et al. (1985) Activation of the Major Immediate Early Gene of Human Cytomegalovirus by Cis–Acting Elements in the Promoter–Regulatory Sequence and by Virus–Specific Trans–Acting Components, Journal of Virology 55 (2): 431–441.

Tal, M. et al., (1987) "Human HER2 (neu) Promoter: Evidence of Multiple Mechanisms for Transcriptional Initiation," Molecular and Cellular Biology 7 (7): 2597–2601.

Tamura, R. et al., (1988) "Effect of Pyrimidine Deoxynucleosides and Sodium Butyrate on Expression of the Glycoprotein Hormone α–Subunit and Placental Alkaline Phosphatase in HeLa Cells," Chemical Abstracts 108 (15): AB–124167.

Tischer, E. et al., (1991) The Human Gene for Vascular Endothelial Growth Factor Journal of Biological Chemistry 266 (18): 11947–11954.

Tocci, M. et al. "The Immunosuppressant FK506 Selectively Inhibits Expression of Early T Cell Activation Genes," Journal of Immunology 143 (2): 718–726.

Vellenga, E. et al., (1988) "Independent Regulation of M–CSF and G–CSF Gene Expression in Human Monocytes," Blood 71 (6): 1529–1532.

Willingham, M. et al., (1990) "A Reversible Multi–Well Chamber for Incubation of Cultured Cells with Small Volumes: Application to Screening of Hybridoma Fusions Using Immunofluorescence Microscopy," BioTechniques 8 (3): 320–324.

Wu, K. et al. "Aspirin Inhibits Interleukin 1–Induced Prostaglandin H Synthase Expression in Cultured Endothelial Cells," Proc. Natl. Acad. Sci. USA 88: 2384–2397.

Yang, Y. et al., (1986) "Human IL–3 (Multi–CSF): Identification by Expression Cloning of a Novel Hematopoietic Growth Factor Related to Murine IL–3," Cell 47: 3–10.

Depto et al. "Regulated Expression of the Human . . . " *Journal of Virology* vol. 63 .No. 3 pp. 1232–1238 Mar. 1989.

DeWet et al "Firefly Luciferase . . . " *Molecular and Cellular Biology* vol. 7, No. 2 pp. 725–737 Feb. 1987.

Mayo et al. "Altered Regulation of the Mouse Metallothionein . . . " *Gene Amplification* pp. 67–73 1982.

Neuhold et al., "Dioxin–Inducible Enhancer Region . . . " *DNA* vol. 5, No. 5. pp. 403–411 1986.

pSVLuci

FIGURE 5

SEQUENCE OF THE pUV OLIGONUCLEOTIDES pUV1:
5'TCGACCCCGGGGCGGCCGCTGATCAGAGTCGGGCCGGTACCGTGCACTACGTAAGATCTAA GCTT3' pUV2:
5'ACTAGTCTGCAGGCTAGCACTCTTCTGGTCCCACAGACTCAGAGAGAACCACCATGGA 3' pUV3:
5'AGACGGCCAAAAACATCAAGAAAAGGCCCGGCCATTCTATCCTCTAGAGGGGATCCAGC TG3' pUV4:
5'TAGATCTTACGTAGTGCACGGTACCGGGCCCGACGTCTGATCAGGCGCCCGGG3' pUV5:
5'GGTGGGTTCTCTCTGAGTCTGTGGGACCAGAAGAGTGCTAGCCTGCAGCTGCAGCTAGTAAGCT3' pUV6:
5'AATTCAGCTGATCCCCTCTAGAGGATAGAATGGCCGGGCCTTTCTTGATGTTTTTGGCGT CTTCCAT3'

FIGURE 7  CONSTRUCTION OF pUV100

FIGURE 10

Oligo #1: 5'- AGCTTGGCCCCCTAGGGCCACTAGTCTGCAGCTATGATGACACAA
ACCCCGCCCAGCGTCTTGTCATTGGCGA-3'

Oligo #2: 3'- ACCGGGGATCCCGGTGATCAGATCGATACTACTGTGTTTGGGG
CGGGTCGCAGAACAGTAACCGCTTAAGCT-5'

Oligo #3: 5'- ATTCGAACACGCAGATGCAGTCGGGGCGGGCGTCCGAGGTC
CACTTCGCATATTAAGGTGACGGCGTGTGGG-3'

Oligo #4: 3'- TGTGCGTCTACGTCAGCCCCGCCCGCGCAGGCTCCAGGTGAAG
CGTATAATTCCACTGCGCACACCCGATC-5'

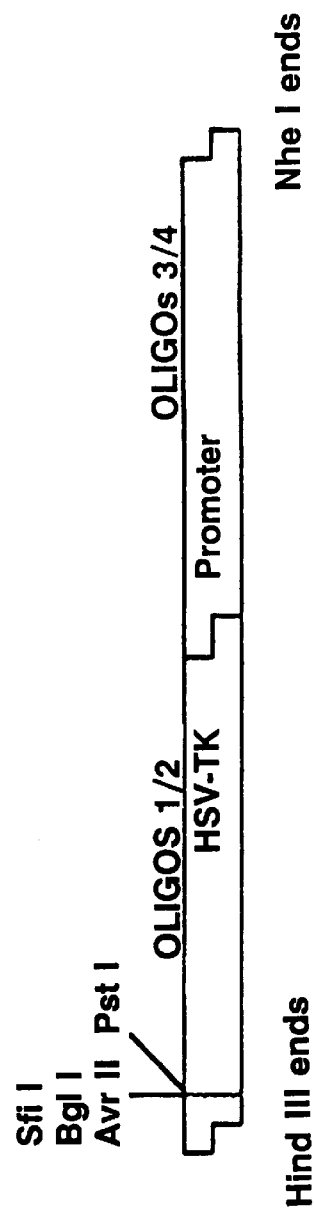

Constuction of pTKL100

CONSTRUCTION OF pTKNEO

CONSTRUCTION OF pTKNEO2

CONSTRUCTION OF pTKNEO3

The Structure of pSV 106

The Structure of pCM106

The Structure of pNEU106

The Structure of pkRAS106

Southern blot of Hep3B clones transfected with pSVluci

SV40

Ratios of Negative Controls

PF000029

EXAMPLES OF PRELIMINARY SCREEN LEAD CHEMICALS SPECIFIC TRANSCRIPTIONAL INHIBITORS

METHODS OF TRANSCRIPTIONALLY MODULATING EXPRESSION OF VIRAL GENES AND GENES USEFUL FOR PRODUCTION OF PROTEINS

This application is a divisional of U.S. Ser. No. 08/255,236, filed Jun. 7, 1994, which was a continuation of U.S. Ser. No. 07/644,233 filed Jan. 18, 1991, now abandoned, which was a continuation-in-part of U.S. Ser. No. 07/555,196, filed Jul. 18, 1990, now abandoned, which was a continuation-in-part of U.S. Ser. No. 07/382,712, filed Jul. 18, 1989 now abandoned. The contents of all of which are hereby incorporated by reference into the present application.

BACKGROUND OF THE INVENTION

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

PROMOTERS USEFUL FOR RECOMBINANT PROTEIN EXPRESSION

Relatively large amounts of substantially pure protein is often necessary (1) to carry out in vitro or in vivo experimentation or (2) for protein structure determination. Often the tissue or cell source harboring the protein of interest may be in short supply or contain insufficient endogenous quantities. Further complicating the ability to obtain adequate amounts of protein is the need to devise often lengthy and multi-stop purification procedures which must usually be specifically designed for a particular protein to be isolated and can ultimately result in drastic losses of product with each successive step being carried out as well as the potential loss of critical protein function due to the inclusion of reagents in the protocol which may be necessary for protein isolation but detrimental to its activity. As a means to circumvent thee and other problems encountered when attempting to isolate large amounts of functional protein, investigators have turned to the use of a variety of different expression systems with which to produce proteins.

Four major expression systems common to investigators include bacterial, yeast, insect and mammalian cells (1). The method of choice is usually dictated by a number of criteria, including size of protein being produced, whether or not the protein is secreted, the presence of host modifying enzymes which can effect the recombinant produced protein structure or function, and for what purpose for which the expressed protein will be used. With these and other parameters in mind, a number of different expression vectors with which to insert the appropriate genetic material has been developed. These often include segments from viral or yeast promoter regions which, when orientated in the proper context to the gene, or cDNA to be expressed, can be recognized by the host cell's transcriptional machinery and result in the production of sufficient protein. The next section of this introduction will deal with some of the more common viral and yeast promoters used for this purpose.

Viral Promoters

A number of viral vectors have been described and include retroviruses, non-defective and defective viral vectors and factors made from various promoters and other regulatory elements derived from DNA and RNA virus sources (2). Promoters consist of short arrays of nucleic acid sequences that interact specifically with cellular proteins involved in transcription. The combination of different recognition sequences and the amounts of the cognate transcription factors determine the efficiency with which a gene is transcribed in a particular cell type (3). Below is a brief description of some viral vectors and their promoters which are used for expressing recombinant proteins.

1. Papovavirusus: These are small, non-enveloped DNA containing viruses, SV-40 and polyoma being two of the best studied examples (4). The viral genome of SV-40 is a covalently closed circular double-stranded DNA molecule of 5243 bp. The genome is divided into early and late regions which are transcribed from the two DNA strands in opposite directions. Various plasmid-based expression vectors contain specific regulatory regions derived from SV-40, the most commonly used being a 300 by segment which lies between the viral early and late transcription units and containing a number of different controlling cis elements, including the DNA origin of replications and promoters, and sites of initiation of transcription of early and late mRNAs (5). Use of the SV-40 regulatory region can result in high levels of expression in transfected host cells.

2. Cytomegalovirus (CMV): The human CMV immediate early promoters serves as an efficient transcription element with which to express foreign proteins. In combination with the CMV enhancer element, the CMV promoter's transcriptional activity can be increased to 10 to 100- fold. The human CMV enhancers are also active in a wide variety of cells from many species.

3. Mouse Mammary Tumor Virus (MMTV): The long terminal repeat (LTR) promoter region of MMTV is probably the best studied example of glucocorticoid-inducible promoters. The glucocorticoid-responsive element (GRE) behaves as an enhancer element and has been localized between −100 and −200 of the MMTV LTR (6). High level protein expression, using the MMTV LTR in combination with other viral promoters/enhancers, can occur in glucocorticoid-responsive cells.

4. Baculovirus: High level expression of foreign proteins in insect cells has been demonstrated using the Baculovirus expression vectors (7,8). The baculovirus vector utilizes the highly expressed and regulated *Autographa californica* nuclear polyhedrosis virus polyhedron promoter which has been modified for the insertion of foreign genes. The viral genome consists of double-stranded circular, supercoiled DNA 128 kilobases long. Most transfer vectors contain the promoter of the polyhedron gene (which is non-essential for replication or production of extracellular virus in cultured cells). The foreign gene sequences in the recombinant plasmid can be transferred to the wild type virus by homologous recombination within a cell transfected with both the plasmid and wild-type virus DNAs.

Yeast Promoters

Protein expression in yeast offers certain advantages over bacterial expression systems. Yeast, being eukaryoic, possess much of the complex cell biology typical of multicellular organisms, including a highly compartmentalized intracellular organization and an elaborate secretory pathway which mediates the secretion and modification of many host proteins (9). Using a yeast expression system thus affords a broader range of potential applications than is possible with bacterial expression systems. A number of yeast promoters are available for high level protein expression. Below is a brief description of the now commonly used systems.

1. Galactose-inducible Promoters (GAL): The Saccharomyces galactose-inducible promoters GAL1, GAL7 and GAL10 have been used for high-level protein production in yeast (10) These promoters can be switched from a near-zero off state to a very high on state by the addition of galactose to a nonglycose-containing medium. At least 28 GAL promoter-containing plasmids are available for protein expression in yeast.

2. Copper Metallothionine Promoter: Induction of the yeast metallothoinine (MT) promoter results in good expression of recombinant genes. The MT promoter, originating upstream of the CUPI coding sequence, is rapidly induced during addition of copper ions to the media. The promoter has been described as approximately a 450 bp fragment which contains the metal regulatory sequences, the mRNA cap site, the TATA box and associated transcription signals (11).

3. CYC1: The CYC1 gene of *Saccharomyces cerevisiae* encoded the cytochrome C protein. Two independent upstream activation sequenced (UAS) are found in the CYC1 gene, which appears to function as regulatory sites. A limited number of CYC1 promoter-containing vector have been reported.

4. Alcohol dehydrogenase 2 (ADH2) promoter: The ADH2 gene is regulated by glucose repression. When grown on glucose, ADN2 transcription is undetectable; however, derepression to a level of about 1% of soluble cellular proteins occurs when yeast are grown on a non-fermentable carbon source (12). Analysis of the ADH2 promoter reveals two cis-acting regulatory components (upstream activation sequences) which mediates derepression (13,14), both of which act synergistically to confer maximum expression on the promoter while keeping it highly repressed on glucose. The ADH2 promoter provides a strong transcriptional start signal for heterologous gene expression. Furthermore, because ADH2 promoter transcription is highly repressed by glucose, cultures can be grown to a highly repressed by glucose, cultures can be grown to a high density in the presence of glucose. When glucose then becomes depleted by normal cellular metabolism promotes derepression to a high level occurs, alleviating the need for changing the growth medium, adding inducing compounds, or else changing the temperature in order to induce the promoter.

The most straight forward application of this invention is the use of the transcriptionally modulating compounds described herein to increase the production of recombinant proteins whose coding sequence has been put under the transcriptional control of one of the claimed promoters. Examples of this are the use of compounds to increase recombinant protein production in tissue culture application, increase monoclonal antibody production by including active compounds in Ascites injections, increase protein production in fungal fermentations, etc. Fungal and Viral promoters are used in the biotechnology industry for the production of protein because they are considerably stronger than the typical promoter. An additional benefit of screening for compounds which increase viral and fungal promoter transcription is that inevitably compound will be found which do just the opposite. These compounds could potentially be developed into pharmaceuticals useful for the treatment of viral or fungal infections.

Viral Diseases

The analysis of viral and yeast promoters offers the opportunity to identify compounds which can inhibit the expression both viral and yeast genes critical for the growth of these organisms. Such compounds could be developed into efficacious pharmacological agents for use in the treatment of diseases caused by viruses or yeast. The list of viral and yeast-related diseases is well beyond the scope of this brief introduction. However, because of the prevalence of viruses and yeast in disease, it is worthwhile to mention a few in brief description.

A. Viral diseases: The list of virally-related diseases is extensive. Additionally, a number of different viruses can infect a particular organ or tissue, thereby leading to disease. A few examples:

(A) Cytomegalovirus (CMV): In vivo, CMV infects a wide range of host tissues (15), including pneumontisis, retinitis, gastrointestinal disease, hepatitis, renalitis and encephalitis. Most CMV-related diseases occur in immuno-compromised patients, either those undergoing immunosuppression to prevent transplant rejection or else presenting with HIV infection. In fact, CMV is a common infection in high risk populations for HIV infection; nearly all homosexual men have serologic evidence of recently acquired or reactivated CMV infection, and 30% shed CMV in the urine intermittently (16). Current therapy of CMV disease treatment includes discontinuation, if possible, of immunosuppressive therapy or else a variety of agents, either singly or in combination, although this has not been shown to be efficacious in patients with serious CMV disease.

(B) Human papillomaviruses (HPV): Infection with HPV is widespread throughout the population. HPV produce epithelial tumors of the skin and mucous membranes, and have been associated with several genital tract malignancies, particularly carcinoma of the cervix. Papillomaviruses are highly species-specific, and cross-species infections occur rarely. Approximately 57 different HPV types have been identified, causing diseases which range from cutaneous and angogenital warts to respiratory papillomatosis (17). Certain HPVs have been intimately associated with genital tract neoplasia, particularly of the uterine cervix (18).

(C) Epstein-Barr Virus (EBV): EBV is lymphotropic, infecting and replicating within lymphocytes efficiently, especially B-cells, although it has been identified in other organs (ie., the salivary gland, the tongue, and in T-cell lymphomas (19). The paradigm for EBV-induced illness is acute infectious mononucleosis, which displays a wide range of clinical and laboratory findings. EBV-associated malignancies have also been described, particularly with Burkitt's lymphoma in which 95% of tumors from endemic (African) cases are EBV-positive (20). Nasopharyngeal carcinoma is also EBV-associated, along with much rarer human cancers including some salivary tumors, malignant thymomas, and squamous tumors of the head, neck and lung (21).

(D) Hepatitis Virus: Viral hepatitis encompasses at least five different diseases caused by five separate reagents. The hepatitis B virus (HBV), which causes classical serum hepatitis (22) can also lead to a chronic hepatitis. HBV replicates largely in the liver. During the early replicative phase, serum levels of HBV are highest. After a 1–4 month incubation period, clinical symptoms and biochemical evidence of liver injury appear, and the disease typically lasts 2–8 weeks. However, not all patients with acute hepatitis B recover completely; a proportion develop chronic hepatitis B. Primary hepatocellular carcinoma (HCC) represents a complication of chronic hepatitis (23). Epidemiological and molecular biological evidence has linked HCC with chronic HBV infection, and chronic HBV infection appears to be the single major etiologic factor in the development of this tumor.

(E) Human Immunodeficiency Virus (HIV): HIV is a retrovirus in which the single-stranded RNA genome is converted into a double-stranded DNA provirus in the host cell by reverse transcriptase. HIV codes for a number of regulatory proteins that act in trans to regulate HIV-transcription. The virus infects and kill CD4 helper T lymphocytes; infection of monocyte-macrophage and possibly other cells may also be a critical aspect of the pathogenesis of HIV-infection as well (24). Clinically, asymptomatic individuals seropositive for HIV may maintain their status for a year to decades. When present, clinically manifestations may include fever, lymphadenopathy, pharyngitis, aseptic meningitis and a mild erythematous macular exanthem (25). Opportunistic infections or malignancies (ie., pneumonia, encephalitis, Kaposi's sarcoma and lymphoma of the brain, or other non-Hodgkin's, non T-cell lymphomas) may eventually develop as a probable result of suppression of a functional immune system caused by HIV infection.

Fungal diseases

Fungal infections are a critical and rapidly increasing health problem. Typically, fungi are opportunistic pathogens, requiring an immunocompromised host or facilitated entry allowing acute infection (e.g., through catheters). A number of factors have contributed to the recent increase in the population of immunosuppressed individuals, most significant of which is the AIDS epidemic. Nearly 60% of AIDS patients develop life threatening opportunistic fungal infections (in particular *Cryptococcus neoformans*). In addition, the increase in transplantations, with the concomitant use of immunosuppressive drugs, has uncovered a critical new need for effective anti-fungal therapies. Fungal infections are also serious problem in patients suffering from neutropenic leukemias or undergoing intensive chemotherapy. Tissue and/or systemic fungal infections occur in 25–40% of persistently febrile granulocytopenic hosts.

This application describes a method to find small molecular weight organic compounds, which modulate the expression of promoters useful for the production of proteins, and compounds which could be developed into antiviral and antifungal drugs. The general approach is to screen large chemical libraries for compounds with the desired biological activity. In this case the desired biological effect is a modulation of transcription of a particular gene.

The expression of a specific gene can be regulated at any step in the process of producing an active protein. Modulation of total protein activity may occur via transcriptional, transcript-processing, translational or post-translational mechanisms. Transcription may be modulated by altering the rate of transcriptional initiation or the progression of RNA polymerase (26). Transcript-processing may be influenced by circumstances such as the pattern of RNA splicing, the rate of mRNA transport to the cytoplasm or mRNA stability. This invention concerns the use of molecules which act by modulating the in vivo concentration of their target proteins via regulating gene transcription. The functional properties of these chemicals are distinct from previously described molecules which also affect gene transcription.

The regulation of transcription in bacteria by low molecular weight chemicals has been documented (27,28). Additionally, extracellular xenobiotics, amino acids and sugars have been reported to interact directly with an intracellular proteinaceous transcriptional activator or repressor to affect the transcription of specific genes. Transcriptional regulation is sufficiently different between procaryotic and eucaryotic organisms so that a direct comparison cannot readily be made. Procaryotic cells lack a distinct membrane bound nuclear compartment. The structure and organization of procaryotic DNA elements responsible for initiation of transcription differ markedly from those of eucaryotic cells.

The eucaryotic transcriptional unit is much more complex than its procaryotic counterpart and consists of additional elements which are not found in bacteria. Eucaryotic transcriptional units include enhancers and other cis-acting DNA sequences (29,30). Procaryotic transcription factors most commonly exhibit a "helix-turn-helix" motif in the DNA binding domain of the protein (31,32). Eucaryotic transcriptional factors frequently contain a "zinc finger" (32,33) or a "leucine zipper" (34) in addition to sometimes possessing the "helix-turn-helix" motif (35). Furthermore, several critical mechanisms at the post-transcriptional level such as RNA splicing and polyadenylation are not found in procaryotic systems (36,37).

In higher eucaryotes, modulation of gene transcription in response to extracellular factors can be regulated in both a temporal and tissue specific manner (38). For example, extracellular factors can exert their effects by directly or indirectly activating or inhibiting transcription factors (38, 39).

Modulators of transcription factors involved in direct regulation of gene expression have been described, and include those extracellular chemicals entering the cell passively and binding with high affinity to their receptor-transcription factors. This class of direct transcriptional modulators include steroid hormones and their analogs, thyroid hormones, retinoic acid, vitamin $D_3$ and its derivatives, and dioxins, a chemical family of polycyclic aromatic hydrocarbons (33,40,41).

Dioxins are molecules generally known to modulate transcription. Dioxins, however, bind to naturally-occurring receptors which respond normally to xenobiotic agents via transcriptionally activating the expression of cytochrome P450, part of an enzyme involved in detoxification. Similarly, plants also have naturally occurring receptors to xenobiotics to induce defense pathways. For example, the fungal pathogen *Phytophthora megasperma* induces an antifungal compound in soybeans. Such molecules which bind to the defined ligand binding domains of such naturally occurring receptors are not included on the scope of this invention.

The clinical use of steroid hormones, thyroid hormones, vitamin $D_3$ and their analogs demonstrates that agents which modulate gene transcription can be used for beneficial effects, although these agents can exhibit significant adverse side effects. Analogs of these agents could have similar clinical utility as their naturally occurring counterparts by binding to the same ligand binding domain of such receptors.

Indirect transcriptional regulation involves one or more signal transduction mechanisms. The regulation typically involves interaction with a receptor, the receptor being part of a multistep intracellular signaling pathway, the pathway ultimately modulating the activity of nuclear transcription factors. This class of indirect transcriptional modulators include polypeptide growth factors such as platelet-derived growth factor, epidermal growth factor, cyclic nucleotide analogs, and mitogenic tumor promoters (42,43,44).

It is well documented that a large number of chemicals, both organic and inorganic, e.g. metal ions, can non-specifically modulate transcription.

Nucleotide analogs have been used in methods to modulate transcription. The mechanism involves incorporating nucleotide analogs into nascent mRNA or non-specifically blocking mRNA synthesis. Similarly, alkylating or intercalating agents have been used to non-specifically inhibit transcription, e.g. cyclophosphamide and doxorubicin.

Moreover, chemical inhibitors of hydroxymethyl-glutaryl CoA reductase (e.g. lovastatin) are known to modulate transcription by indirectly increasing expression of hepatic low density lipoprotein receptors as a consequence of lowered cholesterol levels.

Signal effector type molecules such as cyclic AMP, diacylglycerol, and their analogs are known to non-specifically regulate transcription by acting as part of a multistep protein kinase cascade reaction. These signal effector type molecules bind to domains on proteins which are thus subject to normal physiological regulation by low molecular weight ligands (45,46).

The specific use of sterol regulatory elements from the LDL receptor gene to control expression of a reporter gene has recently been documented in PCT/US88/10095. One aspect of PCT/US/88/10095 deals with the use of specific sterol regulatory elements coupled to a reporter as a means to screen for drugs capable of stimulating cells to synthesize the LDL receptor. PCT/US/88/10095 describes neither the concept of simultaneously screening large numbers of chemicals against multiple target genes nor the existence of transcriptional modulators which (a) do not naturally occur in the cell, (b) specifically trans-criptionally modulate expression of the genes of interest, and (c) bind to I) DNA of II) RNA of III) bind to a protein through a domain of such protein which is not a defined ligand binding domain of a nuclear, transcriptionally activating receptor which naturally occurs in the cell, the binding of a ligand to which ligand binding domain is normally associated with the defined physiological effect. The main focus of PCT/US/88/10095 is the use of the sterol regulatory elements from the LDL receptor as a means to inhibit expression of toxic recombinant biologicals.

The use of molecules to specifically modulate transcription of a gene as described herein has not previously been reported. In fact available literature does not propose the use of a molecule, as described, in a method to specifically modulate transcription. Instead, the available literature has reported methods which define domains of transcriptional regulating elements of particular genes.

Further, the practice of using a reporter gene to analyze nucleotide sequences which regulate transcription of a gene-of-interest is well documented. The demonstrated utility of a reporter gene is in its ability to define domains of transcriptional regulatory elements of a gene-of-interest. Reporter genes which express proteins, e.g. luciferase, are widely utilized in such studies. Luciferases expressed by the North American firefly, *Photinus pyralis* and the bacterium, *Vibro fisheri* were first described as transcriptional reporters in 1985 (47,48).

A method to define domains of transcriptional regulating elements of a gene-of-interest typically has also involved use of phorbol esters, cyclic nucleotide analogs, concanavalin A, or steroids, molecules which are commonly known as transcriptional modulators. However, available literature shows that researchers have not considered using a transcription screen to identify specific transcriptional modulators. Apparently, success would be unlikely in doing so, however, we have demonstrated herein that this is not the case.

There is utility in developing the method of transcriptional modulation of genes by using such molecules as described herein. This method will increase the production capacity of recombinant proteins and allow the development of novel pharmaceuticals.

SUMMARY OF THE INVENTION

The present invention provides a method of transcriptionally modulating the expression of a gene encoding a protein of interest, the expression of which gene is associated with the production in cell culture of a protein encoded by the gene, which comprises contacting a cell, which is capable of expressing the gene, with an amount of a molecule effective to transcriptionally modulate expression of the gene and thereby affect the level of the protein encoded by the gene which is expressed by the cell in culture, which molecule (a) does not naturally occur in the cell and (b) directly transcriptionally modulates expression of the gene.

Additionally, this invention also provides a method of transcriptionally modulating the expression of a gene encoding a protein of interest, the expression of which gene is associated with the production in cell culture of a protein encoded by the gene, which comprises contacting a cell, which is capable of expressing the gene, with an amount of a molecule effective to transcriptionally modulate expression of the gene and thereby affect the level of the protein encoded by the gene which is expressed by the cell, which molecule (a) does not naturally occur in the cell and (b) directly transcriptionally modulates expression of the gene, and (c) binds to a protein at a site on such protein which is not a ligand-binding domain of a receptor which naturally occurs in the cell, the binding of a ligand to which ligand-binding domain is normally associated with the production in cell culture of the protein encoded by the gene.

Further, the invention provides a method of transcriptionally modulating the expression of a gene encoding a protein of interest, the expression of which gene is associated with the production of a protein encoded by the gene, which comprises contacting a cell in culture, which is capable of expressing the gene, with an amount of a molecule effective to transcriptionally modulate expression of the gene and thereby affect the level of the protein encoded by the gene which is expressed by the cell, which molecule (a) does not naturally occur in the cell and (b) indirectly transcriptionally modulates expression of the gene.

Also, the invention includes a method of transcriptionally modulating the expression of a gene encoding a viral protein, the expression of which gene is associated with a defined pathological effect within a multicellular organism, which comprises contacting a cell, which is capable of expressing the gene, with an amount of a molecule effective to transcriptionally modulate expression of the gene and thereby affect the level of the protein encoded by the gene which is expressed by the cell, which molecule (a) does not naturally occur in the cell and (b) directly transcriptionally modulates expression of the gene.

The present invention further includes a method of transcriptionally modulating the expression of a gene encoding a viral protein, the expression of which gene is associated with a defined pathological effect within a multicellular organism, which comprises contacting a cell, which is capable of expressing the gene, with an amount of a molecule effective to transcriptionally modulate expression of the gene and thereby affect the level of the protein encoded by the gene which is expressed by the cell, which molecule (a) does not naturally occur in the cell and (b) directly transcriptionally modulates expression of the gene encoding the protein, and (c) binds to a protein at a site on such protein which is not a ligand-binding domain of a receptor which naturally occurs in the cell, the binding of a ligand to which ligand-looking domain is normally associated with the defined pathological effect.

Additionally, this invention provides a method of transcriptionally modulating the expression of a gene encoding a viral protein, the expression of which gene is associated with a defined pathological effect within a multicellular organism, which comprises contacting a cell, which is capable of expressing the gene, with an amount of a molecule effective to transcriptionally modulate expression of the gene and thereby affect the level of the protein encoded by the gene which is expressed by the cell, which molecule (a) does not naturally occur in the cell and (b) indirectly transcriptionally modulates expression of the gene.

Additionally, this present invention also provides a method of determining whether a molecule not previously known to be a modulator of protein biosynthesis is capable of transcriptionally modulating the expression of a gene encoding a protein of interest which gene is associated with the production in a cell culture of the protein encoded by the gene, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a DNA sequence encoding a polypeptide, which polypeptide is capable of producing a detectable signal, which DNA sequence is coupled to, and under the control of, the promoter, under conditions such that the molecule, if capable of acting as a transcriptional modulator of the gene, causes a measurable detectable signal to be produced by the polypeptide so expressed, quantitatively determining the amount of the signal produced, comparing the amount so determined with the amount of produced signal detected in the absence of any molecule being tested or upon contacting the sample with any other molecule, and thereby identifying the molecule as one which causes a change in the detectable signal produced by the polypeptide so expressed, and thus identifying the molecule as a molecule capable of transcriptionally modulating the expression of the gene.

Further provided is a method of determining whether a molecule not previously known to be a modulator of protein biosynthesis is capable of transcriptionally modulating the expression of a gene encoding a protein of interest which gene is associated with the production in a cell culture of the protein encoded by the gene, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a reporter gene, which expresses a polypeptide, coupled to, and under the control of, the promoter, under conditions such that the molecule, if capable of acting as a transcriptional modulator of the gene, causes a measurable change in the amount of the polypeptide produced, quantitatively determining the amount of the polypeptide so produced, comparing the amount so determined with the amount of polypeptide produced in the absence of any molecule being tested or upon contacting the sample with any other molecule, and thereby identifying the molecule as one which causes a change in the amount of the polypeptide so expressed, and thus identifying the molecule as a molecule capable of transcriptionally modulating the expression of the gene.

The present invention includes a method of determining whether a molecule not previously known to be a modulator of protein biosynthesis is capable of transcriptionally modulating the expression of a gene encoding a protein of interest which gene is associated with the production in a cell culture of the protein encoded by the gene, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a DNA sequence transcribable into mRNA coupled to and under the control of, the promoter, under conditions such that the molecule, if capable of acting as a transcriptional modulator of the gene, causes a measurable difference in the amount of mRNA transcribed from the DNA sequence, quantitatively determining the amount of mRNA produced, comparing the amount so determined with the amount of mRNA detected in the absence of any molecule being tested or upon contacting the sample with any other molecule, and thereby identifying the molecule as one which causes a change in the detectable mRNA amount of, and thus identifying the molecule as a molecule capable of transcriptionally modulating the expression of the gene.

Also, this invention includes a method of determining whether a molecule not previously known to be a modulator of protein biosynthesis is capable of transcriptionally modulating the expression of a gene encoding a viral protein, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a DNA sequence encoding a polypeptide, which polypeptide is capable of producing a detectable signal, which DNA sequence is coupled to, and under the control of, the promoter, under conditions such that the molecule, if capable of acting as a transcriptional modulator of the gene, causes a measurable detectable signal to be produced by the polypeptide so expressed, quantitatively determining the amount of the signal produced, comparing the amount so determined with the amount of produced signal detected in the absence of any molecule being tested or upon contacting the sample with any other molecule, and thereby identifying the molecule as one which causes a change in the detectable signal produced by the polypeptide so expressed, and thus identifying the molecule as a molecule capable of transcriptionally modulating the expression of the gene.

Additionally, this present invention provides a method of determining whether a molecule not previously known to be a modulator of protein biosynthesis is capable of transcriptionally modulating the expression of a gene encoding a viral protein, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a reporter gene, which expresses a polypeptide, coupled to, and under the control of, the promoter, under conditions such that the molecule, if capable of acting as a transcriptional modulator of the gene, causes a measurable change in the amount of the polypeptide produced, quantitatively determining the amount of the polypeptide so produced, comparing the amount so determined with the amount of polypeptide produced in the absence of any molecule being tested or upon contacting the sample with any other molecule, and thereby identifying the molecule as one which causes a change in the amount of the polypeptide so expressed, and thus identifying the molecule as a molecule capable of transcriptionally modulating the expression of the gene.

Finally, this invention provides a method of determining whether a molecule not previously known to be a modulator of protein biosynthesis is capable of transcriptionally modulating the expression of a gene encoding a viral protein, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a DNA sequence transcribable into mRNA coupled to and under the control of, the promoter, under conditions such that the molecule, if capable of acting as a transcriptional modulator of the gene, causes a measurable difference in the amount of mRNA detected in the absence of any molecule being tested or upon contacting the sample with any other molecule, and thereby identifying the molecule as one which causes a change in the detectable mRNA amount of, and thus identifying the molecule as a molecule capable of transcriptionally modulating the expression of the gene.

BRIEF DESCRIPTION OF THE FIGURES

FIG. 5 provides the nucleotide sequences of six oligonucleotides, pUV-1 through pUV-6, which were annealed, ligated, and inserted into the SalI/EcoR1 sites of the plasmid pTZ18R.

FIG. 10 provides the nucleotide sequences of oligos 1–4 used for the construction of a synthetic HSV-Thymidine Kinase promoter and provides a diagrammatic representation of the HSV-TK promoter.

DETAILED DESCRIPTION OF THE INVENTION

Figure 1:
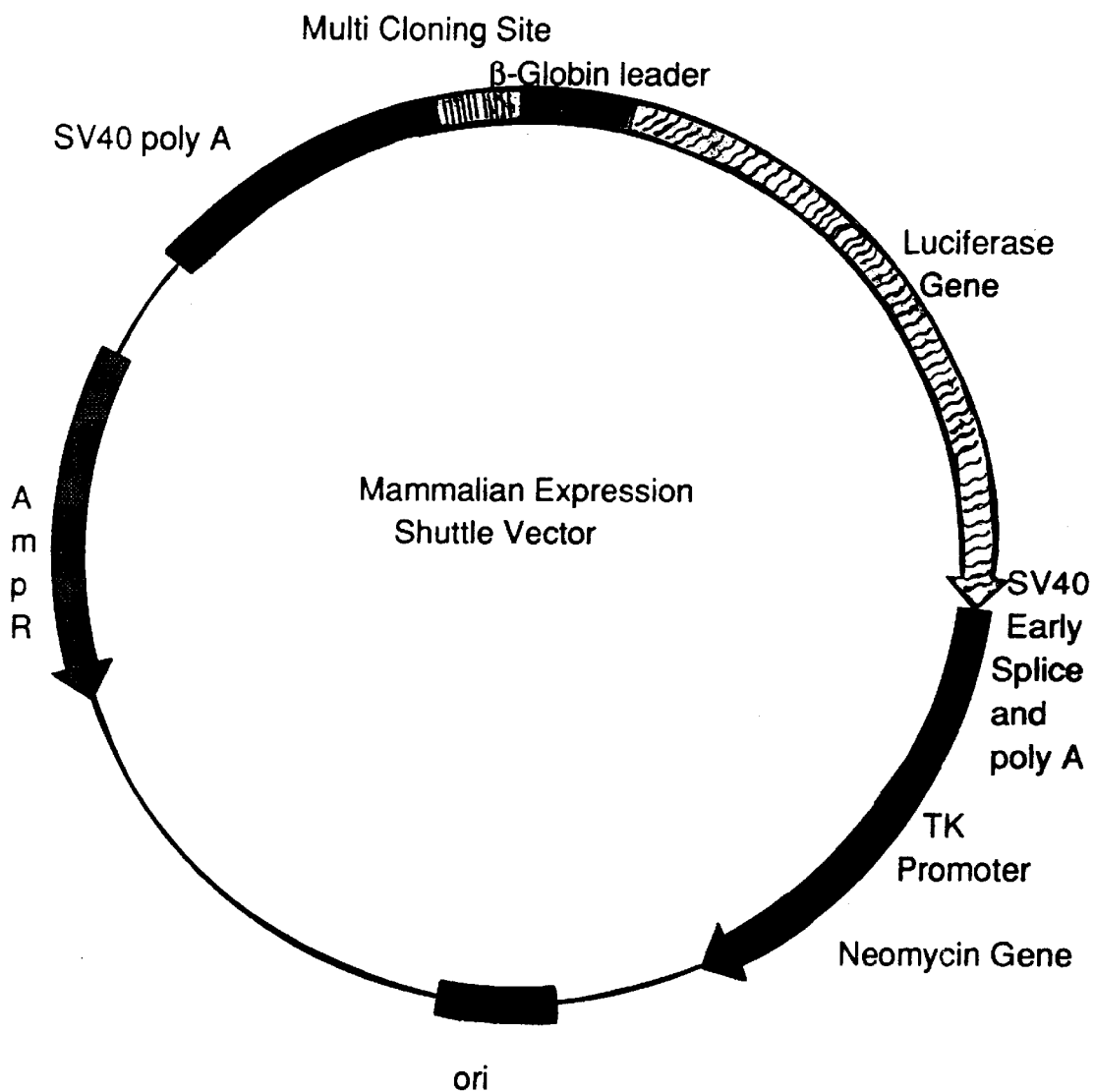
FIG. 1 is a view of the mammalian expression shuttle vector pUV102 with its features. The mammalian expression shuttle vector was designed to allow the construction of the promoter-reporter gene fusions and the insertion of a neomycin resistance gene coupled to the herpes simplex virus thymidine kinase promoter (TK-NEO).

As used in this application, the following words or phrases have the meanings specified.

Antisense nucleic acid means and RNA or DNA molecule or a chemically modified RNA or DNA molecule which is complementary to a sequence present within an RNA transcript of a gene.

Cell culture means the in vitro growth of either single cells or groups of cells by means of tissue culture or fermentation.

Directly transcriptionally modulate the expression of a gene means to transcriptionally modulate the expression of the gene through the binding of a molecule to (1) the gene (2) an RNA transcript of the gene, or (3) a protein which binds to (i) such gene or RNA transcript, or (ii) a protein which binds to such gene or RNA transcript.

A gene means a nucleic acid molecule, the sequence of which includes all the information required for the normal regulated production of a particular protein, including the structural coding sequence, promoters and enhancers.

Indirectly transcriptionally modulate the expression of a gene means to transcriptionally modulate the expression of such gene through the action of a molecule which cause enzymatic modification of a protein which binds to (1) the gene or (2) an RNA transcript of the gene, or (3) protein which binds to (i) the gene or (ii) an RNA transcript of the gene. For example, altering the activity of a kinase which subsequently phosphorylates and alters the activity of a transcription factor constitutes indirect transcript modulation.

Ligand means a molecule with a molecular weight of less than 5,000, which binds to a transcription factor for a gene. The binding of the ligand to the transcription factor transcriptionally modulates the expression of the gene.

Ligand binding domain of a transcription factor means the cite on the transcription factor at which the ligand binds.

Modulatable transcriptional regulatory sequence of a gene means a nucleic acid sequence within the gene to which a transcription factor binds so as to transcriptionally modulate the expression of the gene.

Receptor means a transcription factor containing a ligand binding domain.

Specifically transcriptionally modulate the expression of a gene means to transcriptionally modulate the expression of such gene alone, or together with a limited number of other genes.

Transcription means a cellular process involving the interaction of an RNA polymerase with a gene which directs the expression as RNA of the structural information present in the coding sequences of the gene. The process includes, but is not limited to the following steps: (1) transcription initiation, (2) transcript elongation, (3) transcript splicing, (4) transcript capping, (5) transcript termination, (6) transcript polyadenylation, (7) nuclear export of the transcript, (8) transcript editing, and (9) stabilizing the transcript.

Transcription factor for a gene means a cytoplasmic or nuclear protein which binds to (1) such gene, (2) an RNA transcript of such gene, or (3) a protein which binds to (i) such gene or such RNA transcript or (ii) a protein which binds to such gene or such RNA transcript, so as to thereby transcriptionally modulate expression of the gene.

Transcriptionally modulate the expression of a gene means to change the rate of transcription of such gene.

Triple helix means a helical structure resulting from the binding of one or more oligonucleotide to double stranded DNA.

The present invention provides a method of transcriptionally modulating the expression of a gene encoding a protein of interest. The expression of the gene is associated with the production of a protein (for example a recombinant protein) encoded by the gene. This method comprises contacting a cell in culture, which is capable of expressing the gene, with an amount of a molecule effective to transcriptionally modulate expression of the gene and thereby affect the level of the protein encoded by the gene which is expressed by the cell in culture. In accordance with the practice of this invention the molecule (a) does not naturally occur in the cell and (b) directly transcriptionally modulates expression of the gene.

This invention also provides a method of transcriptionally modulating the expression of a gene encoding a protein of interest, the expression of which gene is associated with the production of a protein encoded by the gene, which comprises contacting a cell in culture, which is capable of expressing the gene, with an amount of a molecule effective to transcriptionally modulate expression of the gene and thereby affect the level of the protein encoded by the gene which is expressed by the cell, which molecule (a) does not naturally occur in the cell and (b) directly transcriptionally modulates expression of the gene, and (c) binds to a protein at a site on such protein which is not a ligand-binding domain of a receptor which naturally occurs in the cell, the binding of a ligand to which ligand-binding domain is normally associated with the production of the protein encoded by the gene.

Further this invention provides a method of transcriptionally modulating the expression of a gene encoding a protein of interest, the expression of which gene is associated with the production of a protein encoded by the gene, which comprises contacting a cell in culture, which is capable of expressing the gene, with an amount of a molecule effective to transcriptionally modulate expression of the gene and thereby affect the level of the protein encoded by the gene which is expressed by the cell. In accordance with the practice of this invention the molecule (a) does not naturally occur in the cell and (b) indirectly transcriptionally modulates expression of the gene.

The present invention also provides a method of transcriptionally modulating the expression of a gene encoding a viral protein, expression of which is associated with a defined pathological effect within the multicellular organism. This method comprises contacting a cell, which is capable of expressing the gene, with an amount of a molecule effective to transcriptionally modulate expression of the gene and thereby affect the level of the protein encoded by the gene which is expressed by the cell. In accordance with the practice of this invention the molecule (a) does not naturally occur in the cell and (b) directly transcriptionally modulates expression of the gene.

The invention further provides a method of transcriptionally modulating the expression of a gene encoding a viral protein, the expression of which is associated with a defined pathological effect within a multicellular organism, which comprises contacting a cell, which is capable of expressing the gene, with an amount of a molecule effective to transcriptionally modulate expression of the gene and thereby affect the level of the protein encoded by the gene which is expressed by the cell, which molecule (a) does not naturally occur in the cell, (b) directly transcriptionally modulates expression of the gene encoding the protein, and (c) binds to a protein at a site on such protein which is not a ligand-binding domain of a receptor which naturally occurs in the cell, the binding of a ligand to which ligand-binding domain is normally associated with the defined pathological effect.

The invention further provides a method of transcriptionally modulating the expression of a gene encoding a viral protein, the expression of which is associated with a defined pathological effect within a multicellular organism, which comprises contacting a cell, which is capable of expressing the gene, with an amount of a molecule effective to transcriptionally modulate expression of the gene and thereby affect the level of the protein encoded by the gene which is expressed by the cell. In accordance with the practice of this invention the molecule (a) does not naturally occur in the cell and (b) indirectly transcriptionally modulates expression of the gene.

In one embodiment of the invention, the molecule does not naturally occur in any cell of a lower eucaryotic organism such as yeast.

In a preferred embodiment, the molecule does not naturally occur in any cell, whether of a multicellular or a unicellular organism. In a presently more preferred embodiment, the molecule is not a naturally occurring molecule, e.g. is a chemically synthesized entity.

In accordance with the invention the cell contacted with the molecule may be a cell of a multicellular organism, for example, an insect cell, an animal cell or a human cell, a hybridoma, a COS cell, a CHO cell, a Hela cell, a fungal cell. (e.g. a yeast cell) of a plant cell.

The method of the invention permits modulating or a transcription of the gene which results in upregulation or downregulation of the expression of the gene (either the gene encoding the protein of interest or the gene encoding the viral protein).

Additionally, the methods of the invention are most advantageously employed to specifically transcriptionally modulate expression of such genes.

In one example, the molecule may bind to a promoter region upstream of the coding sequence encoding the oncogene or the tumor suppressor gene.

In one embodiment of the method of the invention the molecule comprises an antisense nucleic acid which is complementary to a sequence present in a modulatable transcriptional sequence. The molecule may also be a double stranded nucleic acid or a nucleic acid capable of forming a triple helix with a double standed DNA.

In one embodiment the molecule bonds to a modulatable transcription sequence of the gene.

In the case of genes encoding viral proteins, the gene is typically associated with amelioration of a disorder caused by the virus such as a virus infection.

Examples of viruses, the genes of which are subject to transcriptional modulation include cytomegalovirus, hepatitis, herpes, HIV, EBV, papilloma virus. In addition the virus may be one which causes cancer such as hepatocellular carcinoma, a leukemia, or a cervical carcinoma.

In the practice of this invention a gene encoding a protein of interest is a gene encoding any protein of industrial of commercial significance. Many such proteins are either already available commercially or are under commercial development. Merely, by way of example such proteins include human and animal growth hormones, tissue, plasminogen activators erythropoietin, and factor VIII.

The invention may be employed to augment the production of such protein in cell culture, particularly in animal cell culture such as in CHO cells grown in culture and thereby reduce the substantial costs involved in commercial production of such proteins.

The protein invention further provides a method of determining whether a molecule not previously known to be a modulator of protein biosynthesis is capable of transcriptionally modulating the expression of a gene. Such a method comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a DNA sequence encoding a polypeptide, which polypeptide is capable of producing a detectable signal, which DNA sequence is coupled to, and under the control of, the promoter, under conditions such that the molecule, if capable of acting as a transcriptional modulator of the gene, causes a measurable detectable signal to be produced by the polypeptide so expressed, quantitatively determining the amount of the signal produced, comparing the amount so determined with the amount of produced signal detected in the absence of any molecule being tested or upon contacting the sample with any other molecule, and thereby identifying the molecule as one which causes a change in the detectable signal produced by the polypeptide so expressed, and thus identifying the molecule as a molecule capable of transcriptionally modulating the expression of the gene.

Also provided is a method of determining whether a molecule not previously known to be a modulator of protein biosynthesis is capable of transcriptionally modulating the expression of a gene encoding a protein of interest which is associated with the production in a cell cuture of the protein encoded by the gene, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a reporter gene, which expresses a polypeptide, coupled to, and under the control of, the promoter under conditions such that the molecule, if capable of acting as a transcriptional modulator of the gene, causes a measurable change in the amount of the polypeptide produced, quantitatively determining the amount of the polypeptide so produced, comparing the amount so determined with the amount of polypeptide produced in the absence of any molecule being tested or upon contacting the sample with any other molecule, and thereby identifying the molecule as one which causes a change in the amount of the polypeptide so expressed, and thus identifying the molecule as a molecule capable of transcriptionally modulating the expression of the gene.

The invention further includes a method of determining whether a molecule not previously known to be a modulator of protein biosynthesis is capable of transcriptionally modulating the expression of a gene encoding a protein of interest which is associated with production in a cell culture of the protein encoded by the gene, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a DNA sequence transcribable into mRNA coupled to and under the control of, the promoter, under conditions such that the molecule, if capable of acting as a transcriptional modulator of the gene, causes a measurable difference in the amount of mRNA transcribed from the DNA sequence, quantitatively determining the amount of the mRNA produced, comparing the amount so determined with the amount of mRNA detected in the absence of any molecule being tested or upon contacting the sample with any other molecule, and thereby identifying the molecule as one which causes a change in the detectable mRNA amount of, and thus identifying the molecule as a molecule capable of transcriptionally modulating the expression of the gene.

Also provided by this invention is a method of determining whether a molecule not previously known to be a modulator of protein biosynthesis is capable of transcriptionally modulating the expression of a gene encoding a viral protein, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a DNA sequence encoding a polypeptide, which polypeptide is capable of producing a detectable signal, which DNA sequence is coupled to, and under the control of, the promoter, under conditions such that the molecule, if capable of acting as a transcriptional modulator of the gene, causes a measurable detectable signal to be produced by the polypeptide so expressed, quantitatively determining the amount of the signal produced, comparing the amount so determined with the amount of produced signal detected in the absence of any molecule being tested or upon contacting the sample with any other molecule, and thereby identifying the molecule as one which causes a change in the detectable signal produced by the polypeptide so expressed, and thus identifying the molecule as a molecule capable of transcriptionally modulating the expression of the gene.

Additionally, the invention provides a method of determining whether a molecule not previously known to be a modulator of protein biosynthesis is capable of transcriptionally modulating the expression of a gene encoding a viral protein, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a reporter gene, which expresses a polypeptide, coupled to, and under the control of, the promoter, under conditions such that the molecule, if capable of acting as a transcriptional modulator of the gene, causes a measurable change in the amount of the polypeptide produced, quantitatively determining the amount of the polypeptide so produced, comparing the amount so determined with the amount of polypeptide produced in the absence of any molecule being tested or upon contacting the sample with any other molecule, and thereby identifying the molecule as one which causes a change in the amount of the polypeptide so expressed, and thus identifying the molecule as a molecule capable of transcriptionally modulating the expression of the gene.

The invention further provides a method of determining whether a molecule not previously known to be a modulator of protein biosynthesis is capable of transcriptionally modulating the expression of a gene encoding a viral protein, which comprises contacting a sample which contains a predefined number of cells with a predetermined amount of a molecule to be tested, each such cell comprising DNA consisting essentially of (i) a modulatable transcriptional regulatory sequence of the gene, (ii) the promoter, and (iii) a DNA sequence transcribable into mRNA coupled to and under the control of, the promoter, under conditions such that the molecule, if capable of acting as a transcriptional modulator of the gene, causes a measurable difference in the amount of mRNA transcribed from the DNA sequence, quantitatively determining the amount of the mRNA produced, comparing the amount so determined with the amount of mRNA detected in the absence of any molecule being tested or upon contacting the sample with any other molecule, and thereby identifying the molecule as one which causes a change in the detectable mRNA amount of, and thus identifying the molecule as a molecule capable of transcriptionally modulating the expression of the gene.

Further, the sample comprises cells in monolayers. Optionally, the sample comprises cells in suspension.

Cells may include animal cells (such as human cells), fungal cells, insect cells, and plant cells.

In accordance with the practice of the invention, the predefined number of cells may be from about 1 to about $5 \times 10^5$ cells. Alternatively, the predefined number of cells may be from about $2 \times 10^2$ to about $5 \times 10^4$ cells.

Further, in accordance with the practice of the invention, the predetermined amount of the molecule to be tested is based upon the volume of the sample. In one example of the invention, the predetermined amount is from about 1.0 pM to about 20 $\mu$M. In another example, the predetermined amount is from about 10 nM to about 500 $\mu$M.

Additionally, in keeping with the practice of the invention, the contacting is effected from about 1 to about 24 hours. In one example, the contacting is effected from about 2 to about 12 hours. Also, the contacting may be effected with more than one predetermined amount of the molecule to be tested.

Further, the molecule to be tested may be a purified molecule. Moreover, the modulatable transcriptional regulatory sequence may comprise a cloned genomic regulatory sequence. The DNA may consist essentially of more than one modulatable transcriptional regulatory sequence.

In accordance with this invention the polypeptide may be a luciferase, chloramphenicol acetyltransferase, β glucuronidase, β galactosidase, neomycin phosphotransferase, guanine xanthine, phosphoribosyltransferase.

Further, in accordance with the practice of this invention, the polypeptide may be capable of recognizing and binding to an antibody. Alternatively, the polypeptide may be capable of recognizing and binding to biotin.

Additionally, in accordance with the practice of this invention, mRNA may be detected by quantitative polymerase chain reaction.

The invention further provides the above-described screening method which further comprises separately contacting each of a plurality of substantially identical samples, each sample containing a predefined number of cells under conditions such that contacting is affected with a predetermined amount of each different molecule to be tested. In accordance with the practice of the invention, the plurality of samples may comprise more that about $10^4$ samples. Alternatively, the plurality of samples may comprise more than about $5 \times 10^4$ samples.

Additionally, the present invention provides a method of essentially simultaneously screening molecules to determine whether the molecules are capable of transcriptionally modulating one or more genes. The method comprises essentially simultaneously screening the molecules against the genes encoding the proteins of interest according to the above-described method. In accordance with the practice of this invention, more than about 10³ samples per week are contacted with different molecules.

Further, in accordance with the invention, a cell containing a gene comprising a strong promoter (such as an immunoglobulin promoter) may be fused to a coding sequence so as to produce a desired protein encoded by such sequence. Contacting the cell (which is capable of expressing the gene) with a molecule having the properties described herein may be effective to transcriptionally modulate expression of the gene and increase the level of the protein expressed by the cell.

Examples of suitable promoters include a viral promoter. Examples of such include an adenovirus promoter, an simian virus 40 (SV40) promoter, a cytomegalovirus (CMV) promoter, a mouse mammary tumor virus (MMTV) promoter, a Malony murine leukemia virus promoter, a murine sarcoma virus promoter, and a Rous sarcoma virus promoter.

Further, another suitable promoter is a heat shock promoter. Additionally, a suitable promoter is a bacteriophage promoter. Examples of suitable bacteriophage promoters include a T8 promoter, a T3 promoter, an SP6 promoter, a lambda promoter, a baculovirus promoter.

Also suitable as a promoter is an animal cell promoter such as an interferon promoter, a metallothionein promoter, an immunoglobulin promoter. A fungal promoter is also a suitable promoter. Examiner of fungal promoters include an ADC1 promoter, an ARG promoter, an ADH promoter, a CYC1 promoter, a CUP promoter, an ENO1 promoter, a GAL promoter, a PHO promoter, a PGK promoter, a GAPDH promoter, a mating type factor promoter.

Further, plant cell promoters and insect cell promoters are also suitable for the methods described herein.

This invention is illustrated in the Experimental Detail section which follow. These sections are set forth to aid in an understanding of the invention but are not intended to, and should not be construed to, limit in any way the invention as set forth in the claims which follow thereafter.

EXPERIMENTAL DETAILS

Materials and Methods

A. Cell Culture

All media and reagents used for routine cell culture were purchased from Gibco (Grand Island, N.Y.), Hazelton (Lenexa, Kans.), or Whittaker M.A. Biologicals (Walkersville, Md.). Fetal calf serum (FCS) was from Hyclone (Logan, Utah), and nutrients used for serum-free defined media were purchased from Sigma (St. Louis, Mo.), Boehringer Mannheim (Indianapolis, Ind.), Bachem (Torrance, Calif.) and Collaborative Research (Bedford, Mass.). (49, 50).

A human hepatocellular carcinoma derived cell line, Hep3B (ATCC# HB8064), was used for transfection of plasmids containing the SV40 and CMV promoters. These cells were maintained on MEM:OptiMEM (1:1) supplemented with 10% FCS.

A murine embryonic fibroblast cell line, NIH3T3 (ATCC# CCL92), was used for the transfection of plasmids carrying the MMTV promoter. These cells were maintained on DMEM, supplemented with 10% FCS.

A human colon adenocarcinoma cell line, SW480 (ATCC CCL 228) was used for experiments concerning expression of the K-ras proto-oncogene (used as a control). This cell line was maintained on DMEM, 15% fetal calf serum (FCS), 1% Nonessential amino acids (NEAA). Stable transfectants of this cell line were selected in the same medium with the addition of G418 (Geneticin, Gibco) to a final concentration of 0.6 mg/ml.

A human breast adenocarcinoma derived cell line, SK-BR-3 (ATCC HTB 30) was used for the experiments concerning expression of the neu (ErbB2) proto-oncogene (also used as a control). This cell line was maintained on DMEM, 15% FCS and 1 ug/ml insulin. Stable transfectants of this cell line were selected in this same medium with the addition of G418 to a final concentration of 0.4 mg/ml.

B. Construction of the OSI Luciferase-Fusion Reporter Vector

Unless otherwise indicated, molecular cloning procedures were performed essentially according to Maniatis et al. (51). Oligonucleotides were synthesized by the beta-cyanoethyl phosphoramidite method according to protocols provided by the manufacturer of the DNA-synthesizer (Model 380A, Applied Biosystems (Foster City, Calif.).

A mammalian expression shuttle vector was designed to allow the construction of the promoter-reporter gene fusions to be used in high-throughput screens to identify transcriptionally modulating chemicals. Features of the plasmid are shown in FIG. 1. The shuttle vector was constructed in several steps.

Figure 2:
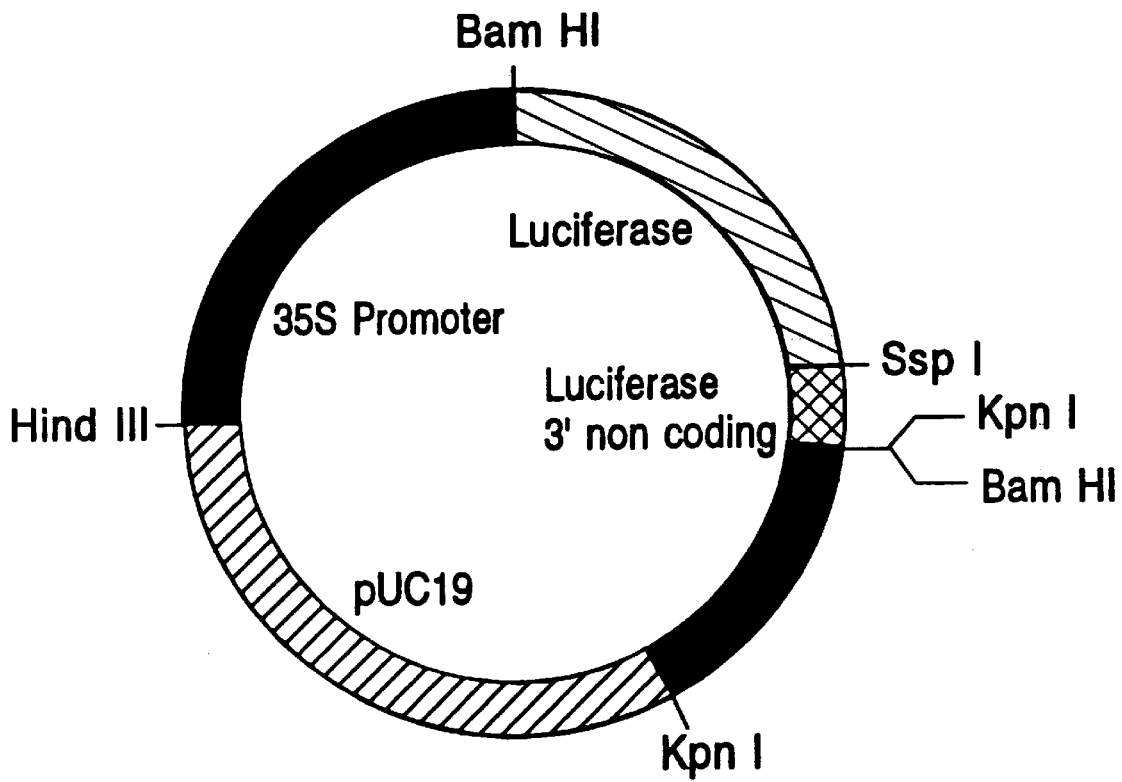
FIG. 2 is a partial restriction enzyme cleavage map of the plasmid pDO432 which contains the luciferase gene from the firefly, *Photinus pyralis*.
Figure 3:
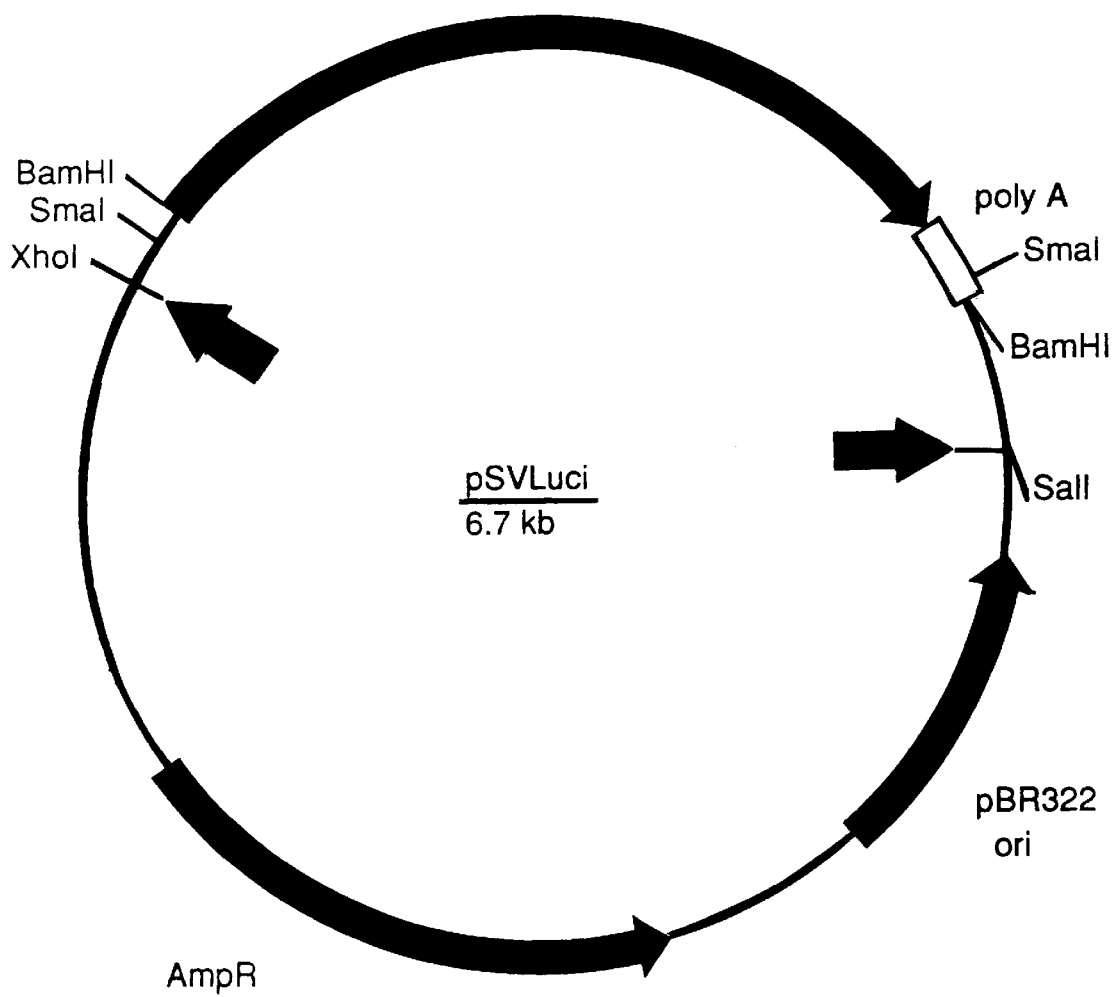
FIG. 3 is a partial restriction enzyme cleavage map of the plasmid pSVLuci which contains the luciferase gene from the firefly, *Photinus pyralis*.
Figure 4:
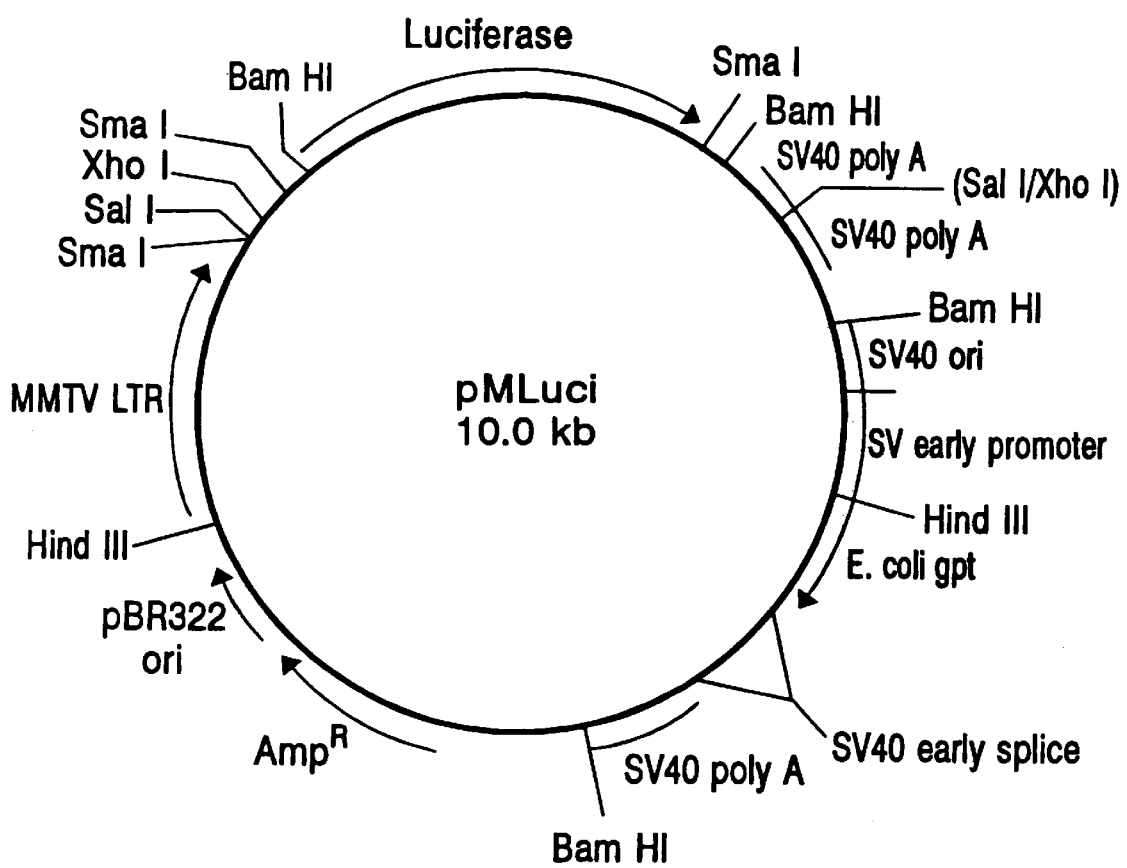
FIG. 4 is a partial restriction enzyme cleavage map of the plasmid pMLuci which contains the luciferase gene of the firefly, *Photinus pyralis* and the mouse mammary tumor virus long terminal repeat.

The firefly luciferase gene was removed from the plant expression plasmid pDO432 (52) (FIG. 2) as a 1.9 kb BamHI fragment and cloned into the BamHI site of pSVL (Pharmacia, Piscataway, N.J.), a mammalian expression vector containing the SV40 promoter. The resulting plasmid (pSVLuci; FIG. 3) was digested with XhoI and SalI to produce a 2.4 kb fragment containing the luciferase coding sequences and the SV40 late polyadenylation site. This fragment was inserted into the XhoI site of pMSG (Pharmacia, Piscataway, N.J.), a eukaryotic expression vector containing the MMTV promoter. The resulting MMTV promoter-luciferase fusion plasmid (pMLuci; FIG. 4) was used to transfect NIH/3T3 cells as described below. Similar constructs can be made using luciferase vectors from Clontech (Palo Alto, Calif.).

Figure 6:
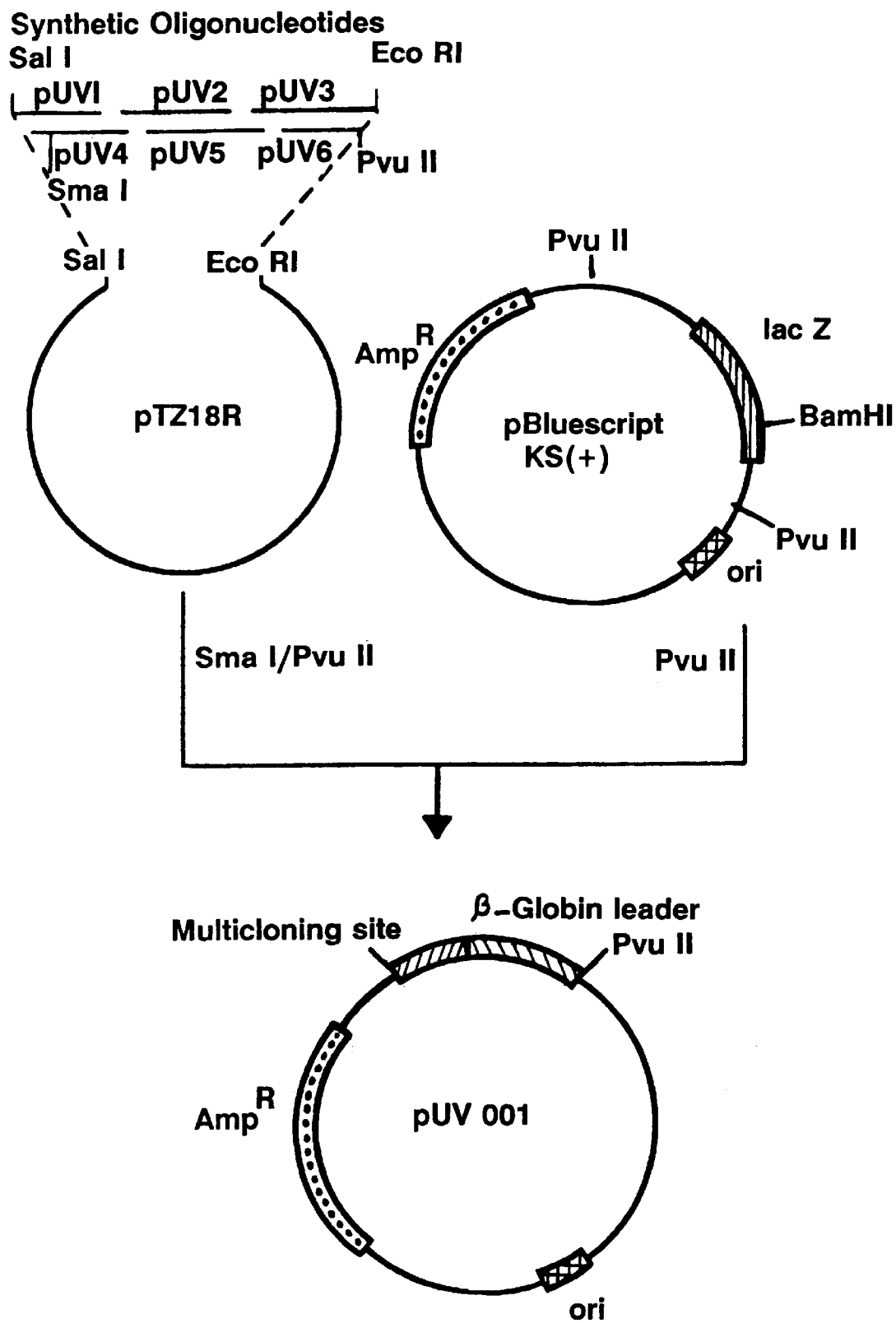
FIG. 6 is a diagrammatic representation of the construction of the plasmid pUV001 from the plasmids pTZ18R and pBluescript KS(+).
Figure 7:
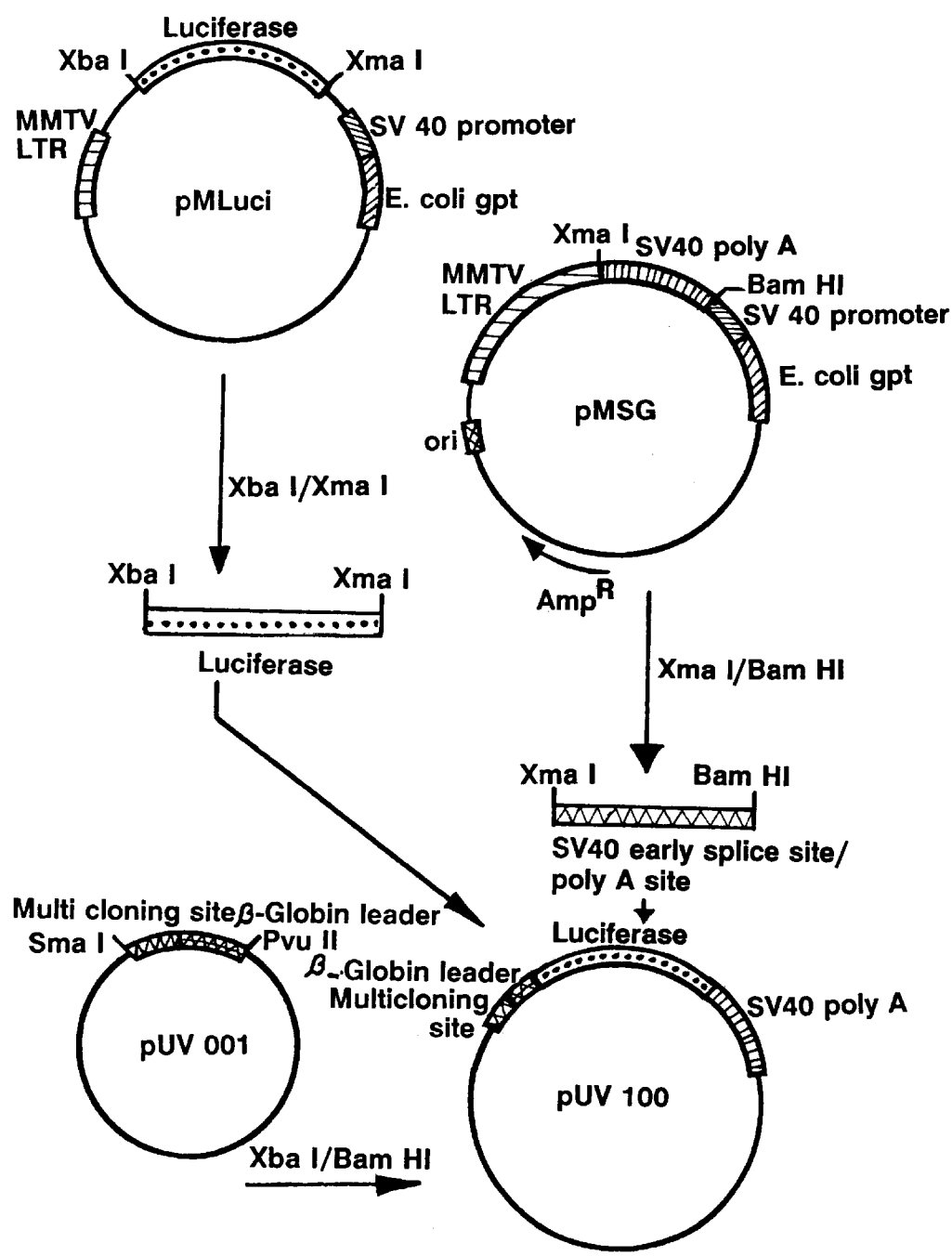
FIG. 7 is a diagrammatic representative of the construction of the plasmid pUV100 from the plasmid pUV01 and two DNA fragments, the XbaI/XmaI fragment from pMLuci and the XmaI/BamHI fragment from pMSG.

Six oligonucleotides (pUV-1 through pUV-6) (SEQ ID NO. 1–6) were synthesized (see FIG. 5 for sequence). The sequences of pUV-1, pUV-2 and pUV-3 correspond to a multicloning site, the beta-globin leader sequence and the first 53 bases of the firefly luciferase coding region. The sequences of pUV-4, pUV-5 and pUV-6 are complementary to the first three oligonucleotides. The pUV oligonucleotides were annealed, ligated and inserted into the SalI/EcoRI sites of pTZ18R (Pharmacia, Piscataway, N.J.) (FIG. 6). The resulting vector was then digested with SmaI/PvuII and the oligonucleotide containing fragment was cloned into the pBluescriptKS(+) plasmid (Stratagene, La Jolla, Calif.), previously digested with PvuII, to yield pUV001 (FIG. 6). Several fragments were ligated into pUV001 to create pUV100. The luciferase coding sequences (except first 53 bases) and polyadenylation site were obtained as a 1.8 kilobase XbaI/XmaI fragment from pMLuci (section B-1, FIG. 4). The SV40 early splice site and the SV40 late polyadenylation site were obtained as an 871 bp XmaI/BamHI fragment from pMSG (Pharmacia, Piscataway N.J., FIG. 7). Both DNA fragments were cloned into pUV001, previously digested with XbaI/BamHI to yield pUV100 (FIG. 7).

A 476 b fragment containing a dimeric SV40 polyadenylation site was then cloned into the BclI site of pUV100

Figure 8:
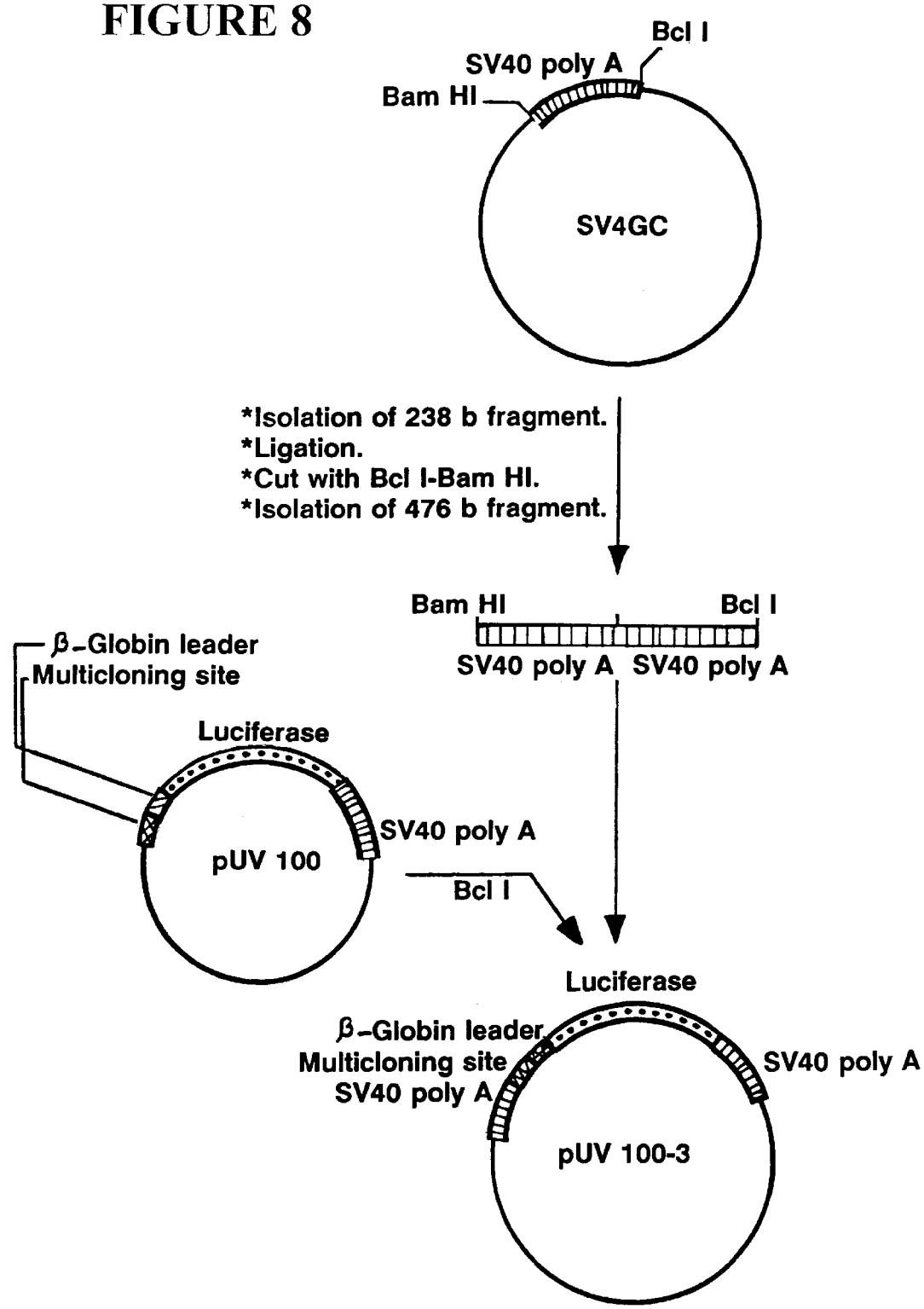
FIG. 8 is a diagrammatic representation of the construction of the plasmid pUV100-3 from the plasmid pUV100 and a 476 b fragment containing a dimeric SV40 polyadenylation site.

(FIG. 8). To do this, a 238 bp BclI/BamHI fragment was obtained from SV40 genomic DNA (BRL), ligated, digested with BclI/BamHI, gel isolated, and inserted into pUV100, resulting in the vector pUV100-3 (FIG. 8). Linkers containing one SfiI and one NotI restriction site were then cloned into the PvuII/BamHI sites of pUV100-3. Two sets of linkers were synthesized containing the SfiI site in opposite orientations (oligonucleotides D-link1 and D-link2 and oligonucleotides R-link1 and R-link2) (SEQ ID NO. 7–10). The sequences of the oligonucleotides were:

5' GATCGGCCCCTAGGGCCGCGGCCGCAT 3' (D-link1)

5' ATGCGGCCGCGGCCCTAGGGGCC 3' (D-link2)

5' GATCGGCCCTAGGGGCGGCCGCAT 3' (R-link1)

5' ATGCGGCCGCGGCCCCCTAGGGCC 3' (R-link2)

Figure 9:
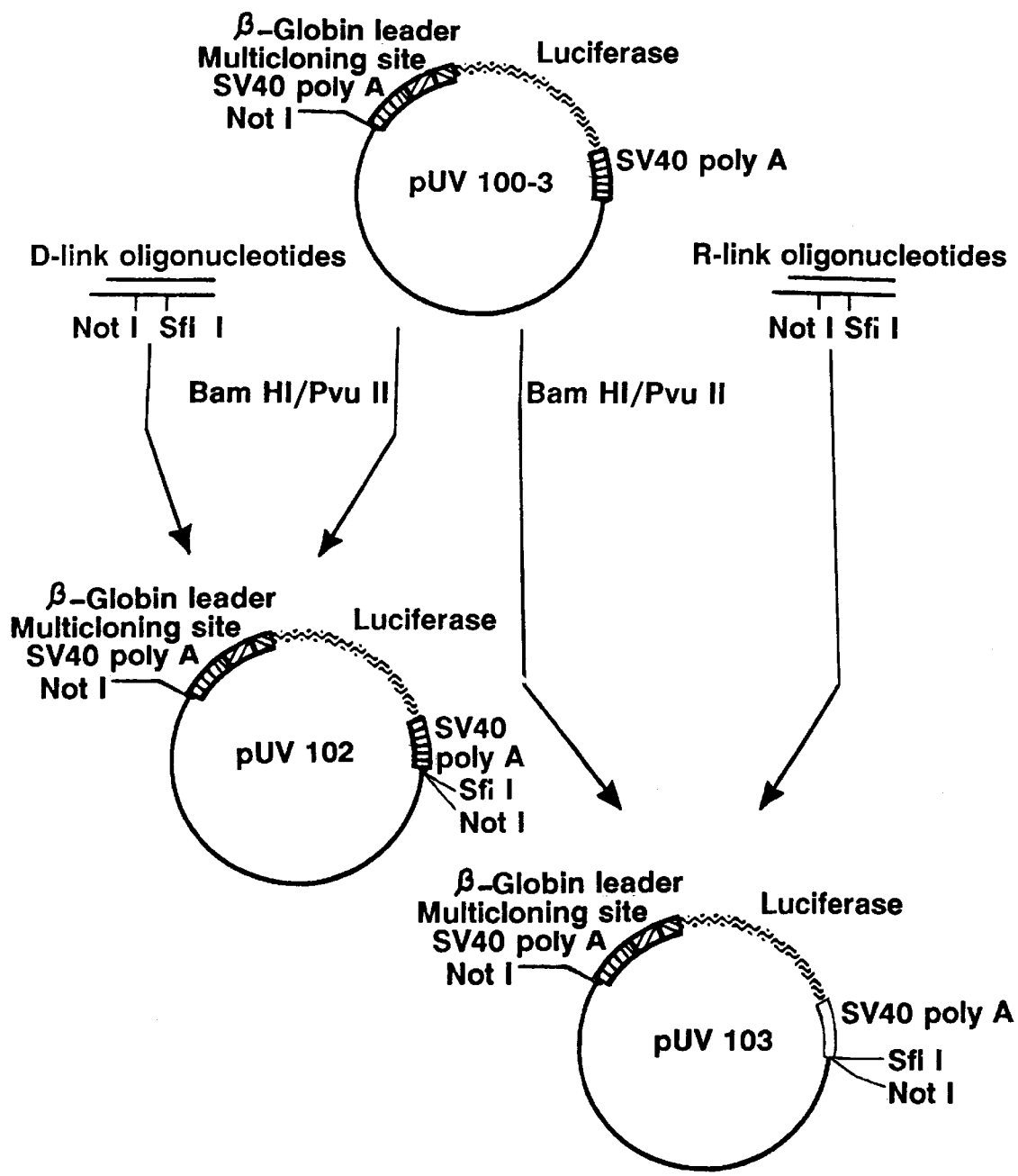
FIG. 9 is a diagrammatic representation of the construction of the plasmids pUV102 and pUV103 from the plasmid pUV100-3 and D-link oligonucleotides and the plasmid pUV100-3 and R-link oligonucleotides, respectively.

The plasmid that contains D-link oligonucleotides was named pUV102 and the plasmid that contains R-link oligonucleotides was named pUV103 (FIG. 9).

Figure 11:
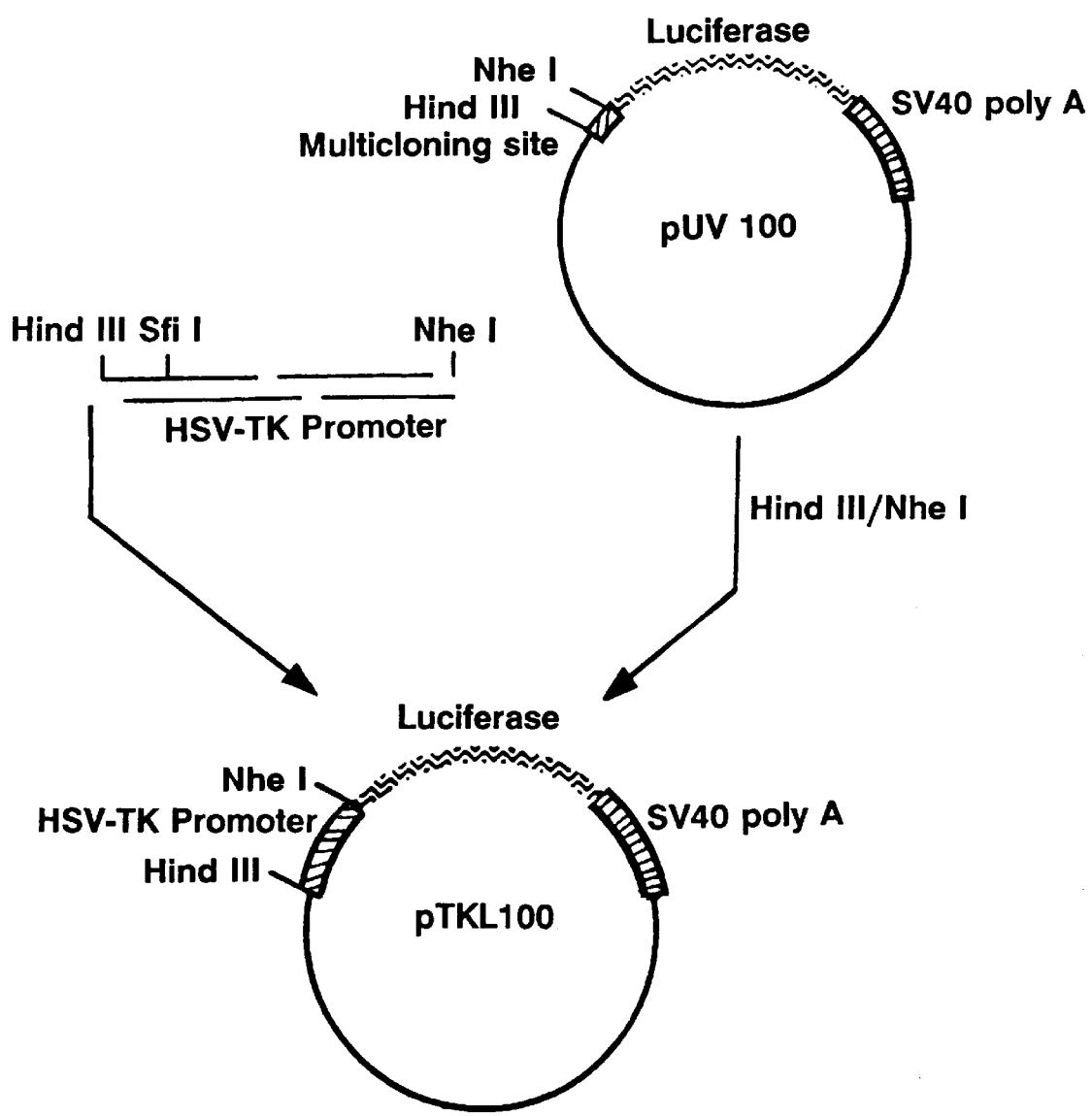
FIG. 11 is a diagrammatic representation of the construction of the plasmid pTKL100 which contains the luciferase gene from the firefly, *Photinus pyralis* and the HSV-TK promoter sequence.
Figure 12:
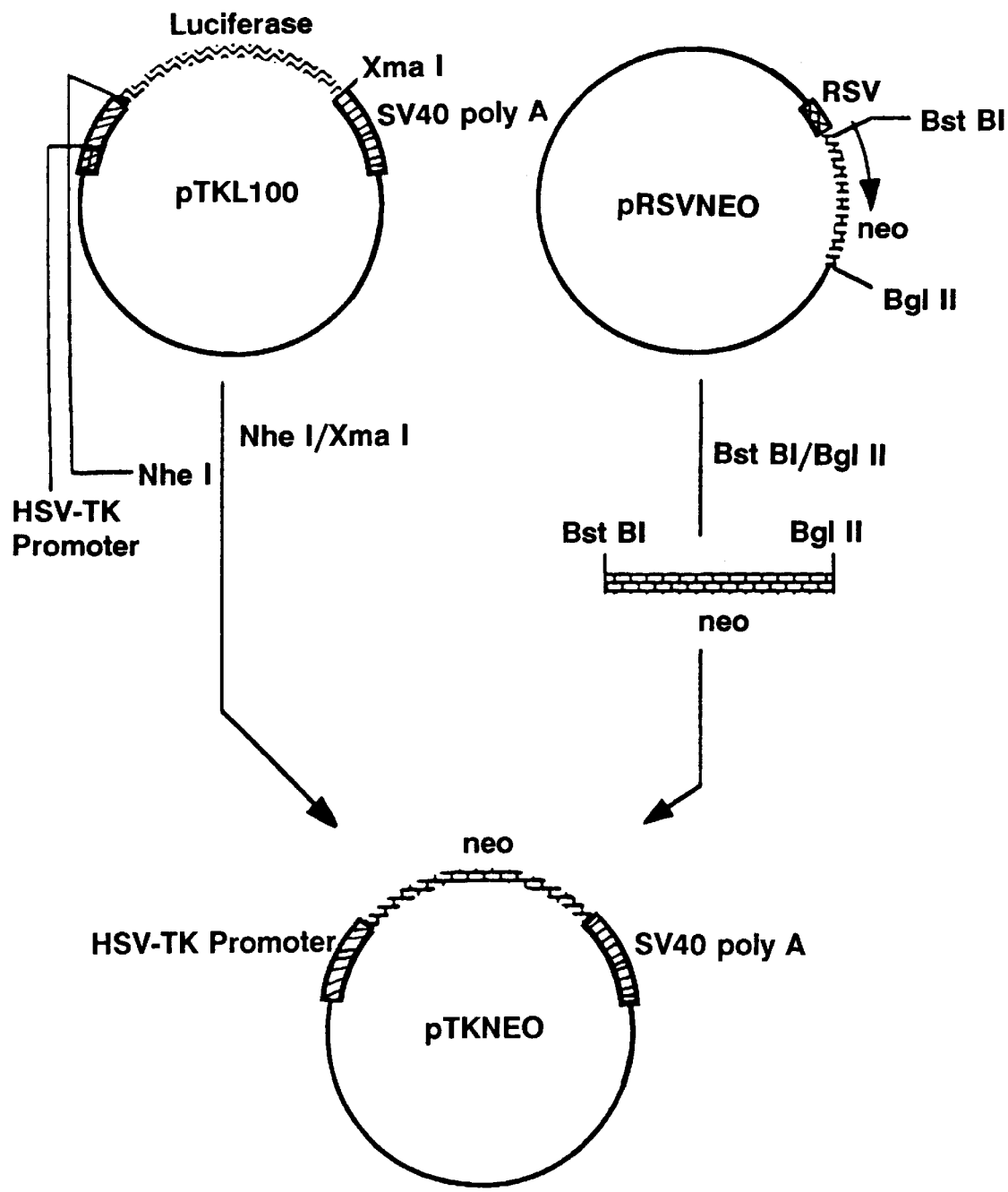
FIG. 12 is a diagrammatic representation of the construction of the plasmid pTKNEO which contains the new gene, from about 3.5 kb NheI/XmaI fragment from pTKL100, and the about 0.9 kb BstBI/BglII fragment containing the neo coding region from private.
Figure 13:
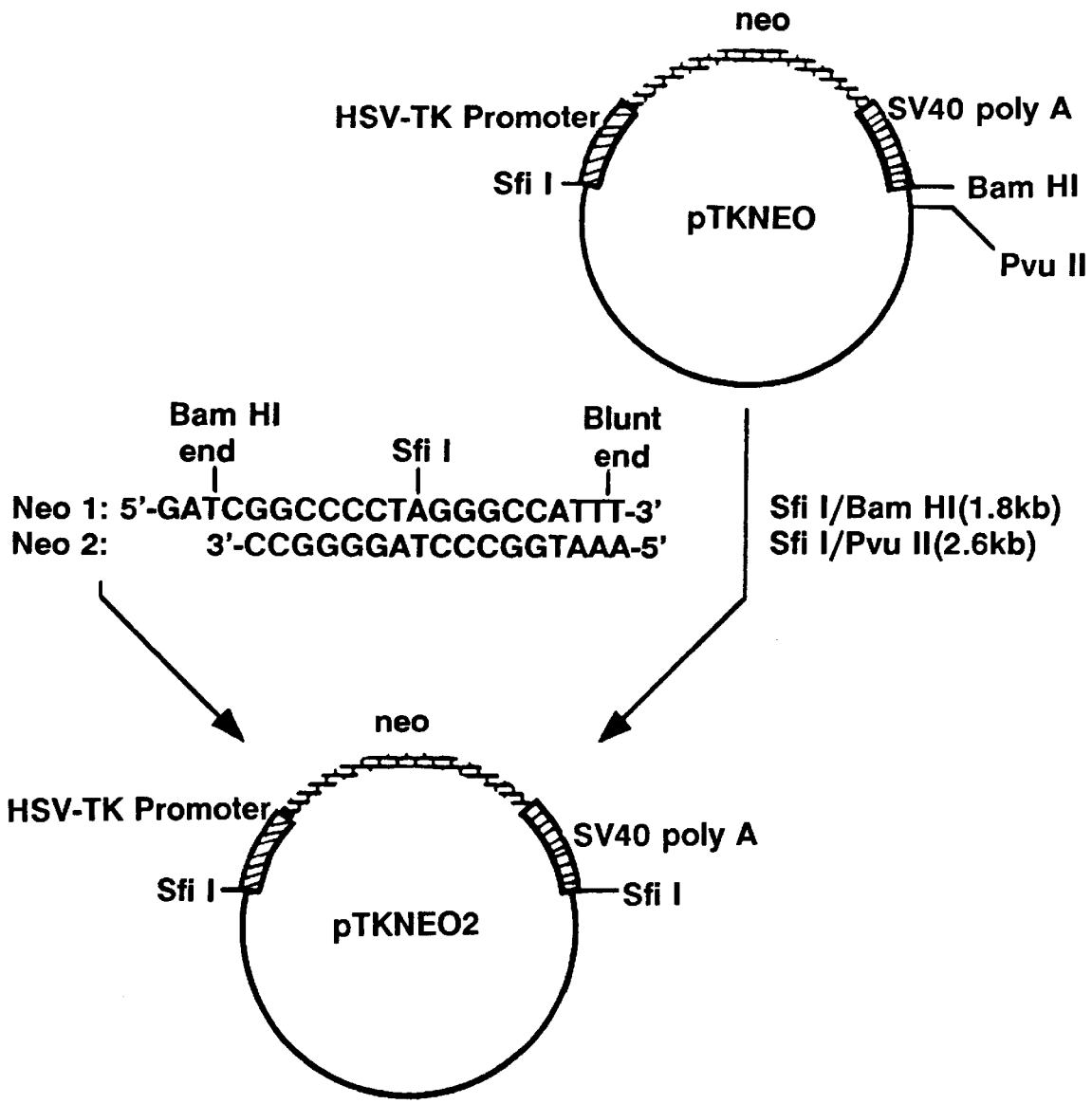
FIG. 13 is a diagrammatic representation of the construction of the plasmid pTKMEO2 from the plasmid pTKNEO and the oligonucleotides Neo 1 and 2.
Figure 14:
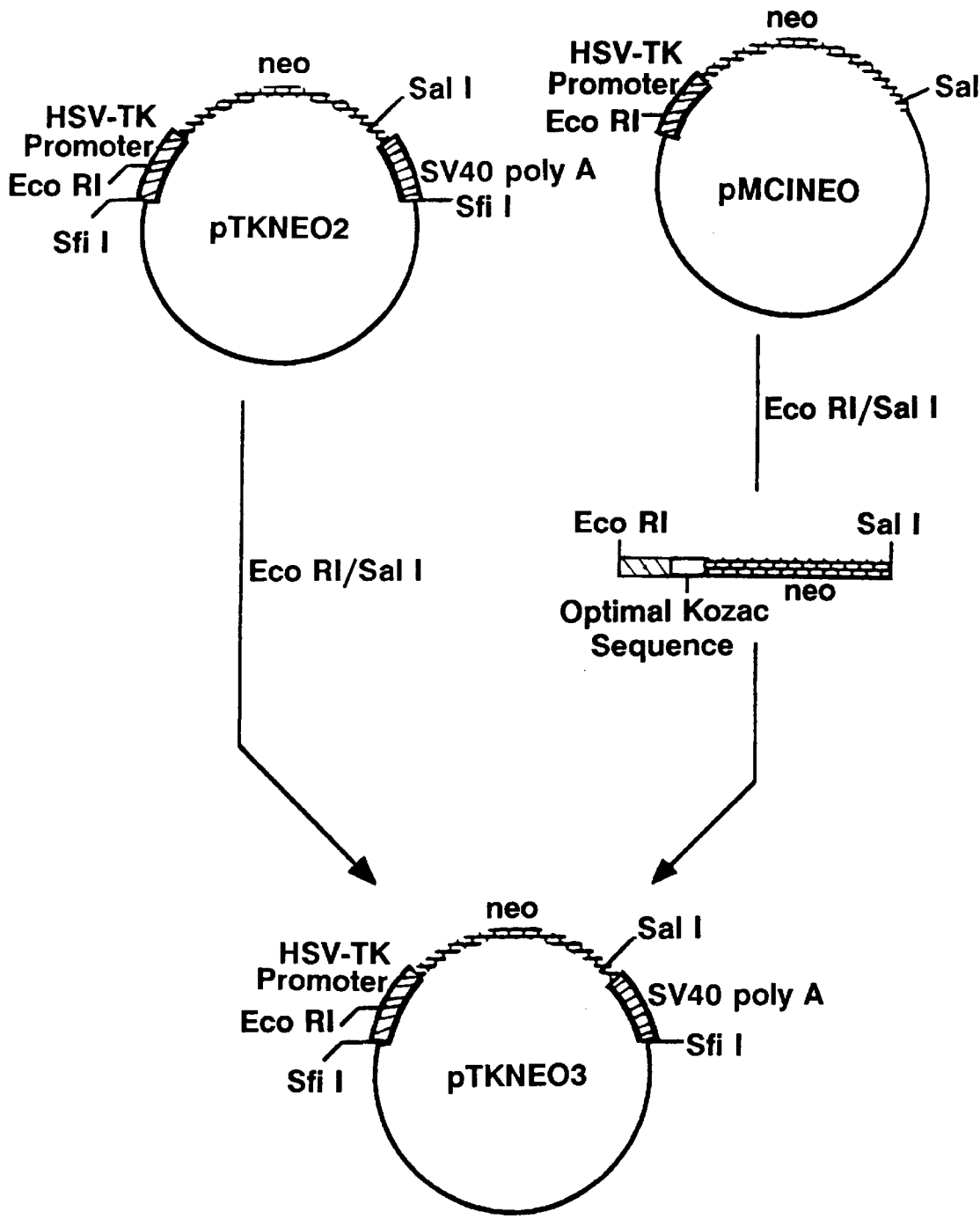
FIG. 14 is a diagrammatic representation of the construction of the plasmid pTKNEO3 from the plasmid PTKNEO2 and about 0.9 kb EcoRl/SalI fragment from pMC1NEO.

The neomycin resistance gene (neo) was then placed under control of the Herpes Simplex Virus thymidine kinase (HSV-TK) promoter to generate a resistance cassette which is free of known enhancer sequences. To do this the HSV-TK promoter was synthesized using four oligonucleotides (FIG. 10) (SEQ ID NO. 11–14) designed according to published sequence information (53), and including an SfiI restriction site 5' of the HSV-TK sequences. These oligonucleotides were phosphorylated, annealed, ligated and inserted into pUV100 digested previously with HindIII/NheI, generating the vector pTKL 100 (FIG. 11). After verifying the HSV-TK sequence, the about 3.5 kb NheI/SmaI fragment was isolated from pTKL100, and the about 0.9 kb BstBI/BglII fragment containing the neo coding region was isolated from pRSV-NEO (54). These two fragments were filled in with Klenow polymerase and ligated to form pTKNEO (FIG. 12). An additional SfiI site was then inserted 3' of the neo gene by isolating the about 1.8 kb SfiI/BamHI and about 2.6 kb SfiI/PVUII fragments of pTKNEO and conducting a three way ligation along with a synthesized SfiI oligonucleotide generating pTKNEO2 (FIG. 13) (SEQ ID NO. 15–16). The HSV-TK/NEO vector containing an optimized Kozac sequence was also utilized (Stratagene, La Jolla, Calif., pMC1NEO). An additional vector was constructed by replacing the about 0.9 kb EcoRI/SalI fragment of pTK-NEO2 with the about 0.9 kb EcoRl/SalI fragment from pMC1NEO. This vector was termed pTKNEO3. (FIG. 14). The SfiI fragment of pTKNEO3, containing the TK promoter and the neomycin resistance gene, was cloned into the SfiI site of pUV102 to yield pUV106.

C. SV40 reporter vector

Figure 15:
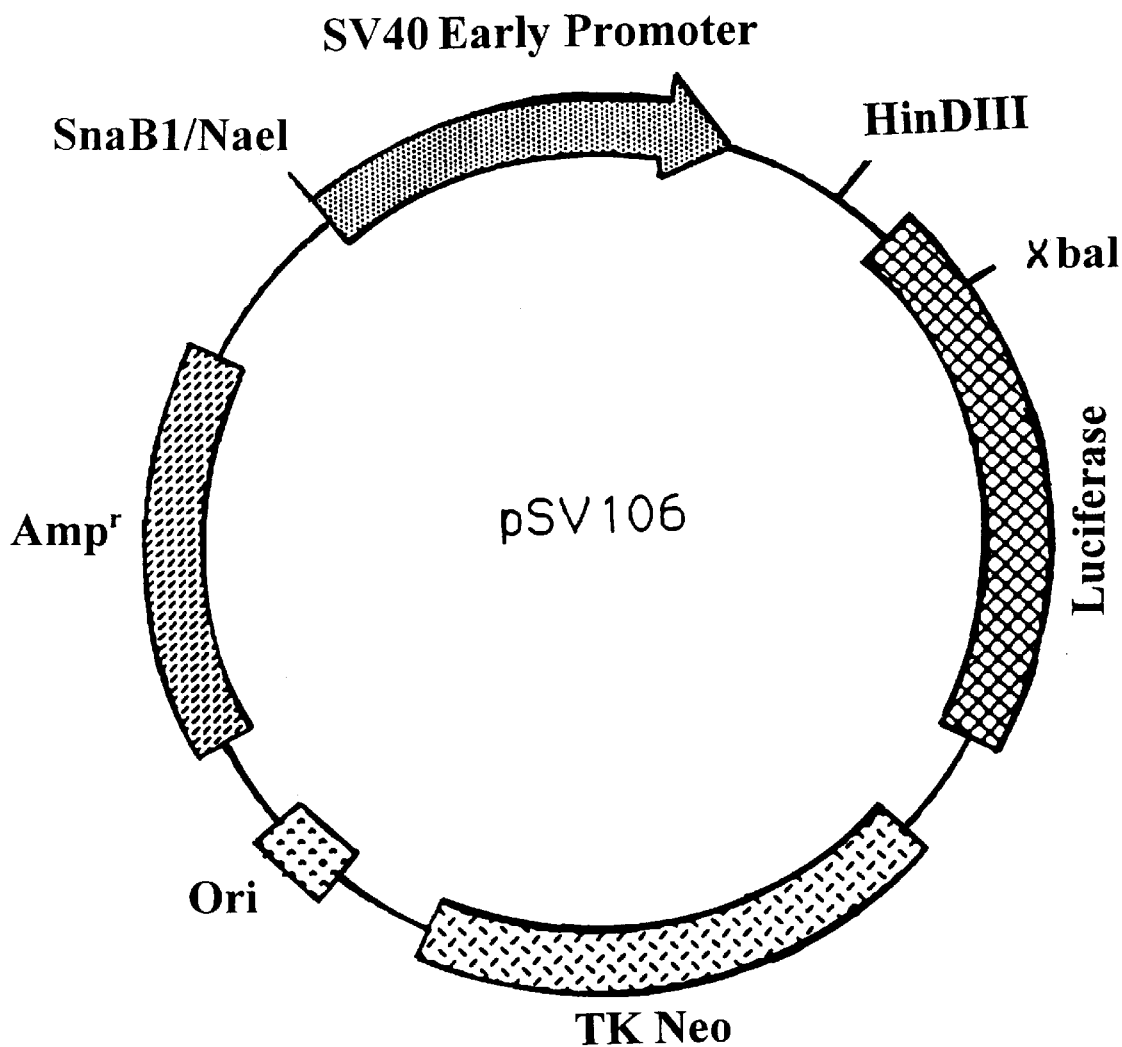
FIG. 15 is a partial restriction enzyme cleavage map of the plasmid pCM106 which contains CMV upstream sequences fused to the luciferase gene.

A 352 bp fragment containing the SV40 early promoter (55) was purified and ligated into pUV102 which had previously been digested with NotI (the ends rendered blunt by treatment with Klenow fragment) and HinDIII, generating pUVSV. A 666 bp NaeI-XbaI fragment from pUVSV containing the SV40 promoter and a portion of the luciferase open reading frame was purified by preparative gel electrophoresis, and ligated int pUV106 which had previously been digested with SnaBI and XbaI, generating pSV106 (FIG. 15), the vector used to transfect the SV40 reporter cell lines.

D. CMV reporter vector

Figure 16:
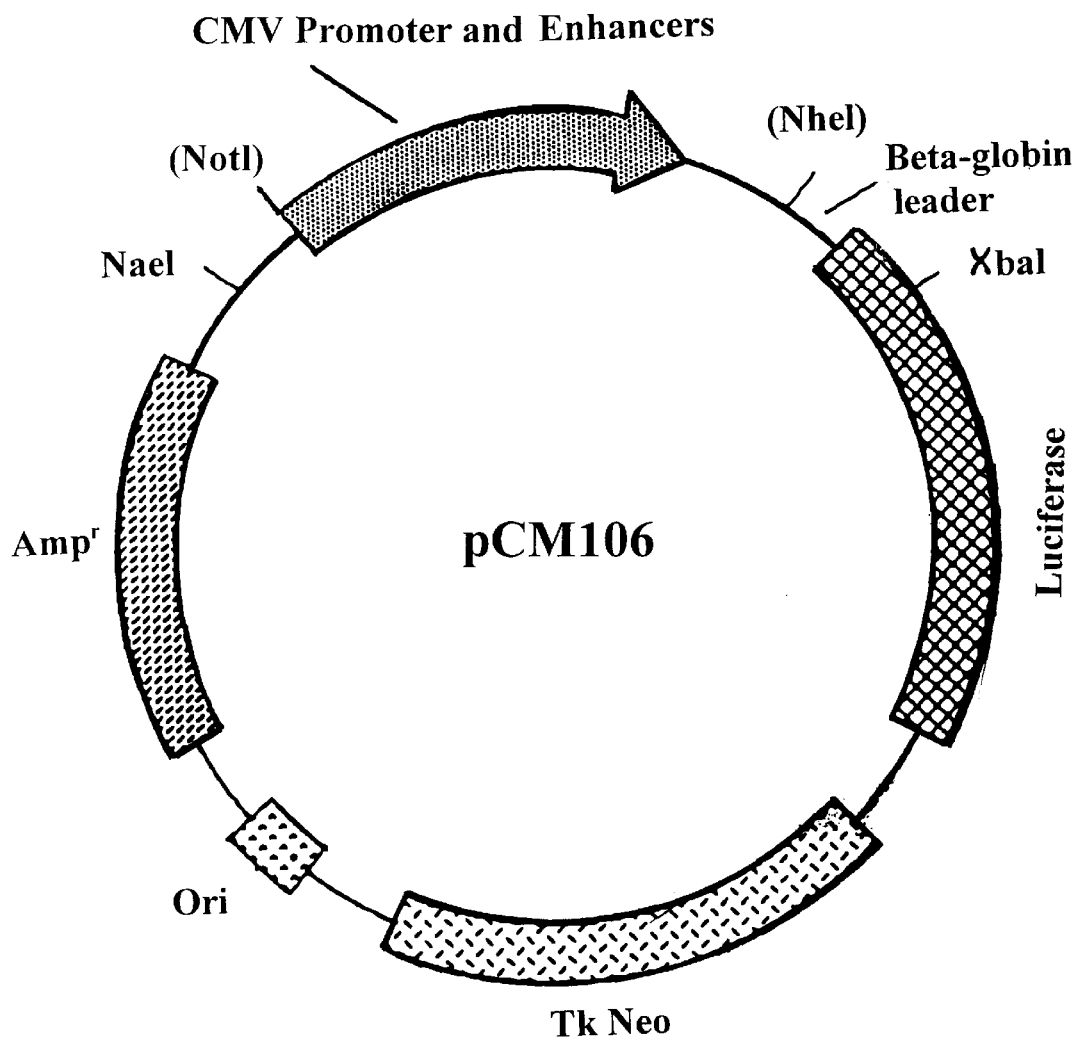
FIG. 16 is a partial restriction enzyme cleavage map of the plasmid pCM106 which contains the Cytomegalovirus immediate early promoter fused to the luciferase gene from the firefly, *Photinus pyralis*.

A 580 bp cytomegalovirus genomic fragment containing the immediate early promoters and enhancers (56) was ligated into pUV100 previously digested with NotI and NheI and rendered blunt ended by treatment with Klenow fragment, generating pUVCM. An 888 bp NaeI-XbaI fragment from pUVCM, including the CMV promoter and enhancers plus a portion of the luciferase coding region, was purified by preparative gel electrophoresis and ligated into pUV106 which had previously been digested with SnaBI and XbaI, generating pCMV106 (FIG. 16), the vector used to transfect the CMV reporter cell lines.

E. neu (c-ErbB2) reporter vector (a specificity control)

Oligonucleotide probes based on the published sequence of the 5' region of the c-ErbB2 gene were synthesized and used to screen a human leukocyte genomic library (Clontech Inc.). A 3.2 kb BglI fragment from a positive plaque, containing the upstream regulatory elements, the 5' untranslated leader and exon 1 was then subcloned into pBluscriptKS(+), generating pNEU001. A 1.8 kb HincII-NcoI fragment from pNEU001, containing the upstream regulatory elements and most of the 5' untranslated leader was purified by preparative gel electrophoresis and ligated into pUV103 previously digested with SnaBI and NcoI, generating pNEU002. Two oligonucleotides were synthesized (SEQ ID NO. 17–18):

5'-CATGGGGCCGGAGCCGCAGTGAGCAC-3' and

5'-CATGGTGCTCACTGCGGCTCCGGCCC-3'

Figure 17:
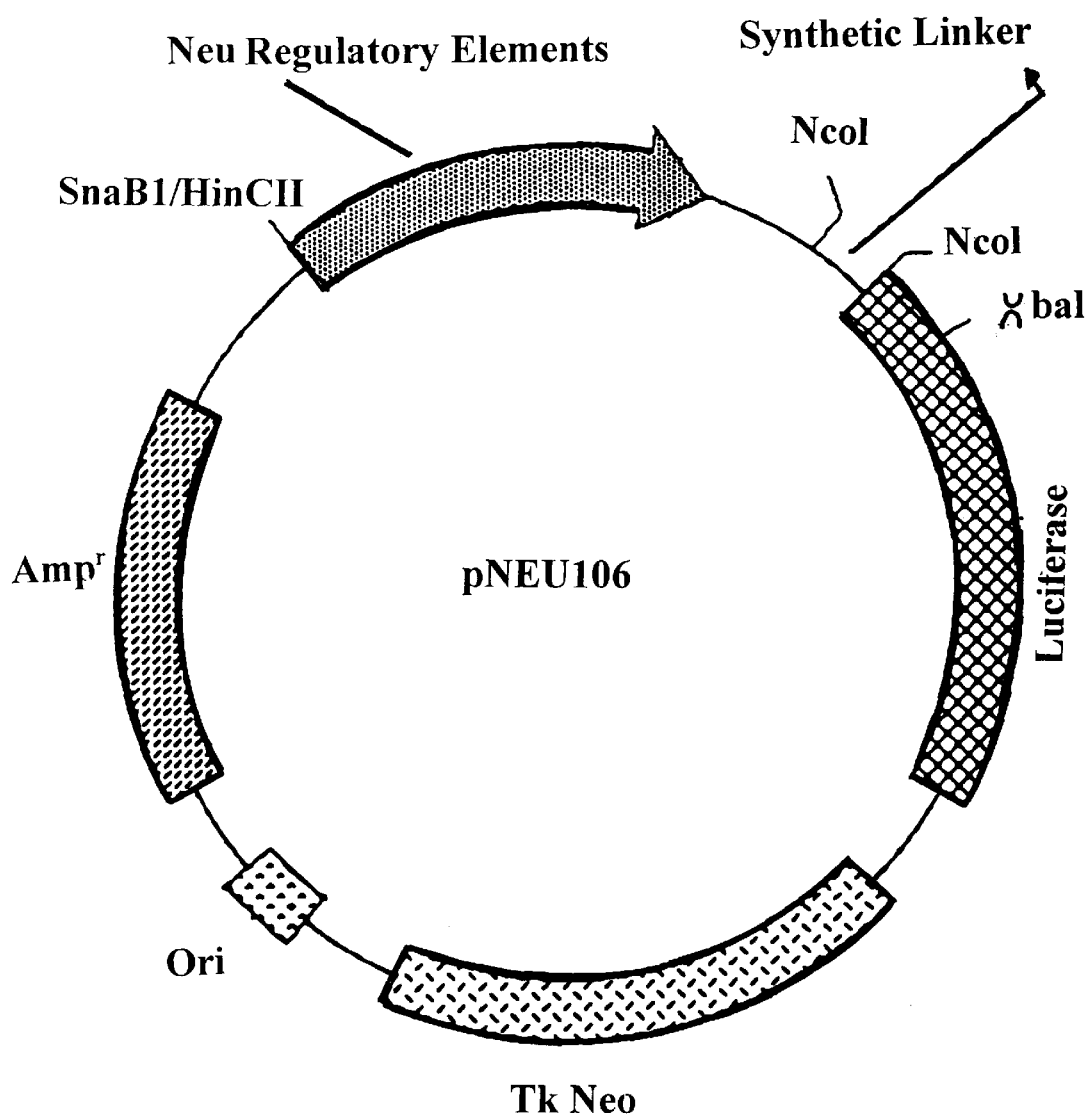
FIG. 17 is a partial restriction enzyme cleavage map of the plasmid pNEU106 which contains neu upstream sequences fused to the luciferase coding region.

These oligonucleotides were annealed to one another, phosphorylated and ligated into NcoI digested pNEU002, generating pNEU103. The synthetic linker fuses the DNA coding for the neu 5' untranslated leader to the luciferase open reading frame such that the AUG utilized for translation initiation of the neu gene forms the first codon of the luciferase gene. The ScaI-XbaI fragment of pNEU103, containing vector sequences, the upstream regulatory elements, the 5'untranslated leader and a portion of the luciferase open reading frame, was purified by preparative gel electrophoresis and ligated into pUV106 which had previously been digested with ScaI and XbaI, generating pNEU106 (FIG. 17). Linearized pNEU106 was used in the transfections to generate the neu-luciferase reporter cell lines as described below.

F. K-ras reporter vector (a specificity control)

Oligonucleotides based on the published K-ras sequence were used to isolate two genomic clones by standard methods from a human leukocyte library (Clontech). DNA from these two phages was subcloned into pBluscriptKS(+) (Stratagene) generating pKS4 and pKS11.

A 4 kb XhoI-StuI fragment of pKS11, containing most of intron 1 and exon 1 up to a point 11 bases 5' of the point of translation initiation, was isolated by preparative gel electrophoresis and ligated into XhoI-StuI digested pGEM7Zf (Promega) which had been previously modified by inserting an adaptor the ApaI and XhoI sites in the original vector. This adaptor comprised of two oligonucleotides (SEQ ID NO. 19–20) (5'-TCGAGATCTGAGGCCTGCTGACCATGGGGGCC-3' and 5'-CCCATGGTCAGCAGGCCTCAGATC-3') annealed to one another and was used to allow the proper alignment of the K-ras ATG initiator codon with the luciferase ORF in the final construct (below). The resulting plasmid was designated pGEM715.

A 3 kb HinDIII-XhoI fragment from pKS4, comprising 2.2 kb of K-ras untranscribed upstream DNA and sequences coding for exon 0 and part of intron 1 was purified by preparative gel electrophoresis and ligated into pGEM715 which ad been previously digested with HinDIII and XhoI to generate pGEM7.

Figure 18:
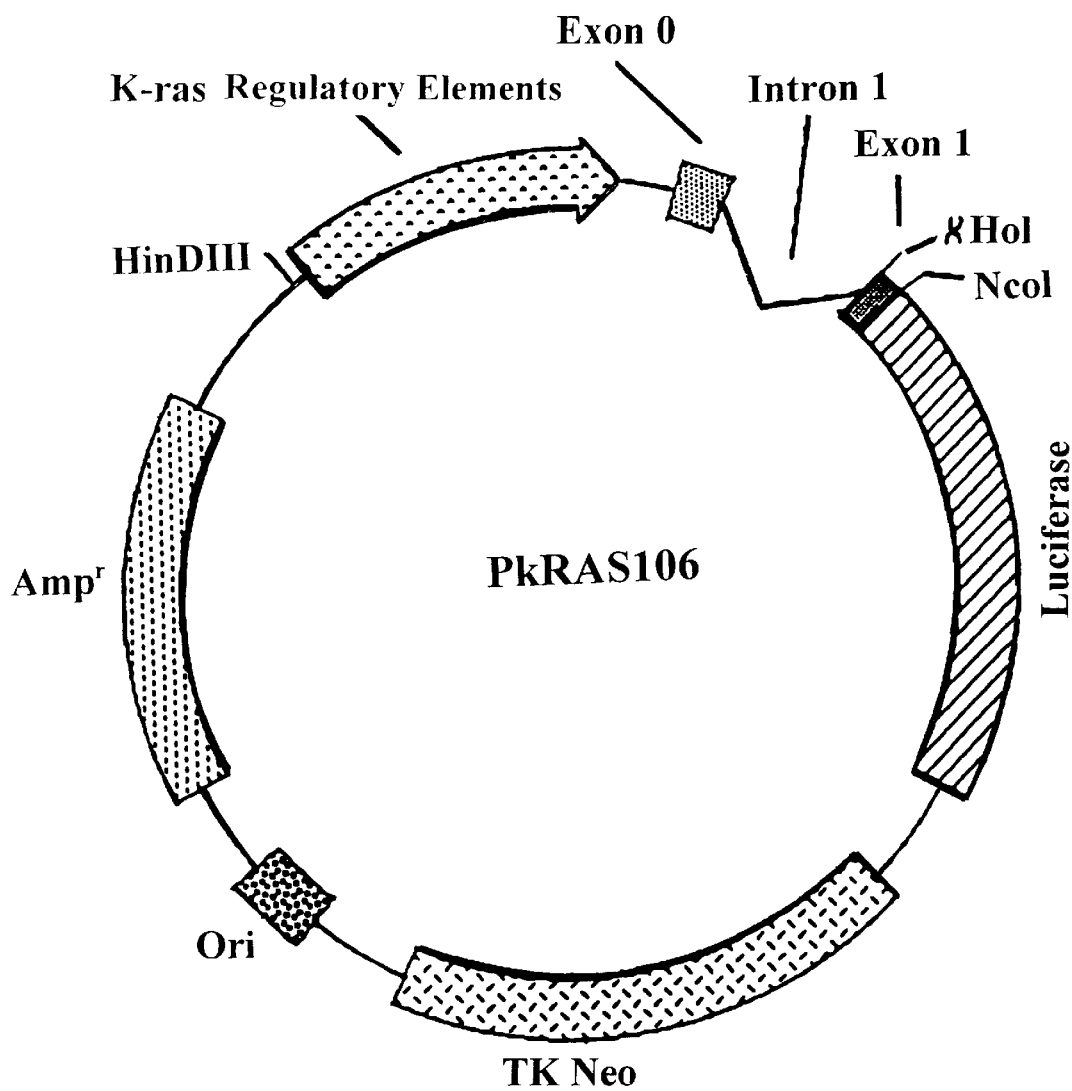
FIG. 18 is a partial restriction enzyme cleavage map of the plasmid pKRAS106 which contains K-ras upstream sequences fused to the luciferase gene from the firefly, *Photinus pyralis*.

A 7.7 kb HinDIII-NcoI fragment of pGEM7, comprising 2.2 kb of K-ras upstream regulatory elements, exon 0, intron 1, and part of exon 1 (to the ATG at the NcoI site), was purified by preparative gel electrophoresis and ligated into pUV102 which had previously been digested with HinDIII and NcoI to generate pKRAS102. The TK-Neo fragment from pTKNeo3 was then ligated into the SfiI site of pKRAS102 to generate pKRAS106 (FIG. 18), the vector used for transfections to generate the stable K-ras reporter cell lines.

G. Liquid Scintillation Counter Bioluminescence Assay

To assay for luciferase expression in transient expression assay in the various transfected clones, cells were incubated with various transcriptional inducers in serum free defined media, washed 3 times with Dulbecco's phosphate-buffered saline (D-PBS, Gibco) and lysed in Lysis Buffer 1 (50 mM Tris acetate pH7.9, 1 mM EGTA, 10 mM magnesium acetate, 1 mg/ml bovine serum albumin [BSA], 0.5% Brij 58, 2 mM ATP, 100 mM dithiothreitol [DTT]). all reagents were obtained from Sigma except for DTT which was from Boehringer Mannheim. After lysis, cell debris was sedimented by brief centrifugation, and 950 ul of supernatant extract were added to a glass scintillation vial. Samples were counted individually in an LKB (Gaithersburg, Md.) scintillation counter on a setting which allows measurement of individual photons by switching off the coincidence circuit. The reaction was started by addition of 50 ul of 2 mM luciferin (Sigma, St. Louis, Mo. or Boehringer Mannheim, Indianapolis In.) in Buffer B (Buffer B-Lysis Buffer 1 without Brij 58, ATP and DTT) to the 950 ul of lysate. Measurement was started 20 seconds after luciferin addition and continued for 1 minute. Results were normalized to protein concentration using the Bradford protein assay (BioRad, Richmond Calif.) or to cell numbers using Trypan Blue (Sigma) exclusion counting in a hemocytometer.

H. Transfection

Cell were transfected by one of three methods, following manufacturer's instructions; by Calcium phosphate precipitation (Pharmacia), Lipofection (Life Technologies Inc.) or electroporation (BioRad). In most cases, 25–75 ug of plasmid DNA, linearized by a single restriction endonuclease cut within the vector sequences, was electroporated into approximately 5 million cells. When co-transfection of a seperate neomycin resistant plasmid was employed the molar ratio of luciferase fusion plasmid to neomycin resistant plasmid was either 10:1 or 20:1. Neomycin resistant clones were selected by growth in media containing G418 (Geneticin, Gibco) (ref).

I. Isolation of Single Cell Clones Containing Various Promoter-Luciferase Fusion Constructs 1. pMluci (MMTV cell line) pMluci and pSV2Neo, an antibiotic resistance plasmid (112), were co-transfected into NIH/3T3 mouse fibroblast cells using the calcium phosphate precipitation method (103) with a commercially available kit (Pharmacia, Piscataway N.J.). Two days later, cells were transferred to media containing 0.4 mg/ml G418 and were grown for an additional 10–14 days. G418-resistant clones were isolated by standard methods. Once sufficient cell numbers were obtained, clones were analyzed based on several criteria: constitutive luciferase production, induction of luciferase expression by dexamethasone (1 $\mu$m, Sigma, St. Louis, Mo.), satisfactory attachment to microtiter plates used in the high-throughput screen and acceptable standard deviation in multiple luciferase expression assays (see below for assay protocol). This analysis was carried out using the luciferase assay conditions described above. Of the clones which satisfied the above criteria for the high throughput screen, one clone, M10, was selected for use.

2. pSV106

Hep3B hepatocellular carcinoma cells were transfected by electroporation with 75 micrograms of pSV106 which had been linearized by a single ScaI cut within the vector backbone. Neomycin resistant colonies were isolated and tested for luciferase activity. Luciferase positive, neomycin resistant clones were subjected to Southern blot analysis (see below). The best clone, producing the most luciferase activity from a single, correctly integrated vector was selected for use as the SV40 reporter cell line in the high throughput screen (this clone was designated SV12).

3. pCM106

Hep3B hepatocellular carcinoma cells were transfected by electroporation with 75 micrograms of pCM106 which had been linearized by a single ScaI cut within the vector backbone. Neomycin resistant colonies were isolated and tested for luciferase activity. Luciferase positive, neomycin resistant clones were subjected to Southern blot analysis (see below). The best clone, producing the most luciferase activity from a single, correctly integrated vector was selected for use as the CMV reporter cell line in the high throughput screen (this clone was designated CM1).

4. pNEU106

75 micrograms of the pNEU106 plasmid was linearized by a single restriction endonuclease cleavage within the vector backbone and electroporated into HTB30 human breast carcinoma cells. Neomycin resistant clones were isolated and tested for luciferase activity. Clones testing positive for luciferase production was subjected to Southern blot analysis (see below). The best clone (producing the highest signal and carrying a single intact copy of the transfected DNA) was utilized for high throughput screening (designated clone N2).

5. K-ras (pKRAS106) into SW480

75 micrograms of the pKRAS106 plasmid was linearized by a single restriction endonuclease cleavage within the vector backbone and electroporated into SW480 human colon carcinoma cells. Neomycin resistant clones were isolated and tested for luciferase activity. Clones testing positive for luciferase production were subjected to Southern blot analysis (see below). The best clone (producing the highest signal and carrying a single intact copy of the transfected DNA) was utilized for high throughput screening (designated clone K2).

J. Construction of a Yeast Expression Vector

Plasmid pHZ18 (97, 98) contains 2$\mu$ DNA for propagation in *S. cerevisiae*, the yeast promoter cyc 1, which is compatible with expression in yeast cells, and the URA 3 gene for selection. The plasmid was linearized with BamH1, the ends were filled-in using deoxynucleotides and *E. coli* DNA polymerase Klenow fragment, and then the plasmid was digested with Aat II. A 4.1 kb fragment containing the cyc1 promoter, URA3 and 2$\mu$ genes was separated by agarose gel electrophoresis and subsequently purified by electroelution onto ion-exchange paper (Whatman, DE81). Plasmid pBR322 was treated with encodnucleases Aat II and Pvu II and a 2.2 kb fragment containing the plasmid's origin of replication and the amp$^R$ gene was isolated by agarose gel electrophoresis and eluted onto DE81 paper.

The 2.2 kb pBR322 and 4.1 kb pHZ18 fragments were ligated using T4 DNA ligase according to standard procedures (94). The resulting 6.3 kb vector pHZBR was digested with BamH1 for subsequent insertion of the luciferase coding sequence downstream of the cyc1 promoter.

An Nco I-Sal I fragment of pUV102 containing the luciferase gene starting at the second ATG, was made blunt-ended by filling in and ligated into the filled-in BamH1 site of pHZBR. Clones of the correct orientation were identified via restriction mapping to yield plasmid pHZluci24. This plasmid was used to transform *S. cerevisiae* strain DB745.

K. Transformation of Yeast Cells

*S. cerevisiae* DB745 were made competent according to published methods (99). One and 4 µg of either pHZluci24 or pHZ18 (transfection control) were added to the competent cells and incubated at 30° C. for 30 minutes. Lithium acetate-PEG was mixed gently with the cells and allowed to incubate for another 45 minutes at which time the cells were shifted to 42° C. for 5 minutes. The cells were spread onto uracil(-) plates and incubated at 30° C. for several days. Cell colonies were picked, grown to saturation in YPD media and analyzed for luciferase activity. Stock cultures were made from positive clones, and each was subsequently analyzed for suitability for the 96-well plate high-throughput assay.

L. Yeast Luciferase Bioluminescence Assay in Microtiter Plates

Expression of the firefly luciferase gene was determined by measuring luminescence in the presence of substrates essentially as described above.

Formatting the assay to a 96-well plate required otpimization of cell lysis conditions, substrate concentrations and the reaction measurement time. Initial experiments were conducted using purified luciferase and substrates. Bioluminescence was measured either by scintillation counting or in a Dynatech ML1000 luminometer and the reaction conditions were optimized to provide the highest signal-to-noise ratio. Cell lysis conditions were optimized to result in complete lysis of the cells yet not interfere with the luciferase reaction. The detergent Brij 58 fulfilled these requirements. In the current format the 96-well assay was carried out as follows:

$1–2 \times 10^4$ yeast cells were seeded into 96-well plates which have been custom designed to allow filtration of the media while retaining the cells, and which are opaque to permit analysis using a luminometer (Millipore). After the media was removed from the cells by suction, 100 µl of lysis buffer (50 mM Tris/acetate pH 7.9, 1 mM EGTA, 10 mM Mg-acetate, 0.5% Brij 58, 100 mM DTT and 4 mM ATP, 0.2 mM Luciferin, 800 U/ml lyticase) was added and the plates were incubated at room temperature for 10 minutes. Bioluminescence was monitored in a Dynatech ML1000 luminometer.

M. Southern blotting

To monitor correct and complete stable integration of transfected promoter/reporter constructs, stably transfected cell clones were subjected to Southern blot analysis (57). Genomic DNA was prepared of each clone to be tested and restriction-cut with Dra I. After electrophoresis, transfer to nylon filters and immobilization by UV irradiation using a Stratalinker UV device (Stratagene, La Jolla, Calif.), integrated promoter/luciferase fusion constructs were visualized by probing with radioactively labelled XbaI-EcoRI fragments of the luciferase coding region. Probes were labelled using the random primer method (58). Since Dra I cuts in the SV40 polyadenylation sites located in the OSI mammalian expression shuttle vector just upstream the inserted promoter sequences as well as downstream of the luciferase coding region, but not in any of the promoter sequences used for generating stably transfected cell clones, a single fragment should be visualized by the probe used. The size of that fragment should be characteristic for each of the three promoter sequences analyzed.

N. High-Throughput (HTP) Screening of Mammalian Reporter Cells

Cell plating: Dynatech Microliter 96 well plates were custom pretreated for cell attachment by Dynatech Laboratories, Inc. (Chantilly, Va.). Alternatively, the 96 well plates were treated with 50 ul per well of human fibronectin (hFN, 15 lg/ml in PBS, Collaborative Research, Bedford, Mass.) overnight at 37° C. hFN-treated plates were washed with PBS using an Ultrawash 2 Microplate Washer (Dynatech Labs), to remove excess hFN prior to cell plating. M10 and G21 cells maintained in their respective serum media (with 0.2 mg/ml G418) were washed with PBS, harvested by trypsinization, and counted using a hemocytometer and the Trypan Blue exclusion method according to protocols provided by Sigma, St. Louis, Mo. Chemical Company. Cells were then diluted into serum free defined media (with 0.2 mg/ml G418), and 0.2 ml of cell suspension per well was plated onto Dynatech treated plates (G21) or hFN-treated plates (M10) using a Cetus Pro/Pette (Cetus, Emeryville Calif.). Plates were incubated overnight at 37° C. in a humidified 5% $CO_2$ atmosphere.

Addition of Chemicals to Cells: Chemicals from the Oncogene Science file were dissolved in DMSO at concentrations of 3–30 mg/ml. A liquid handling laboratory work station (RSP 5052, Tecan U.S. Chapel Hill, N.C.) was used to dilute the chemicals (three dilutions; 5 fold, 110 fold, and 726 fold). 10 ul of each dilution were added to each of quadruplicate samples of cells contained in the wells of 96-well Dynatech Microlite Plates. Cell plates were then shaken on a microplate shaker (Dynatech, medium setting, 30 sec.) and incubated for 6 hours at 37° C., 5% $CO_2$.

Bioluminescence Assay: After incubation with OSI-file chemicals, cell plates were washed 3 times with PBS using an Ultrawash 2 Microplate Washer (Dynatech Labs) and 75 ul of Lysis Buffer 2 were added to each well (Lysis Buffer 2 is the same as Lysis Buffer 1 exept that the ATP and DTT concentrations were changed to 2.67 mM and 133 mM, respectively). Bioluminescence was initiated by the addition of 25 ul 0.4 µm Luciferin in Buffer B to each well, and was measured in a Dynatech ML 1000 luminometer following a 1 minute incubation at room temperature. Data were captured and analyzed using Lotus-Measure (Lotus) software.

More recently the cell lysis buffer was modified to also contain the luciferin. Therefore, lysis of cells and the bioluminescence reaction begin simultaneously and the production of bioluminescent light reaches a maximum at about 5 min. The level of light output declines by about 20% within further 30 min. For better lysis buffer stability bovine serum albumin has been omitted. This improved lysis buffer has been shown to remain fully functional for at least 12 hours, when kept on ice and protected from direct light.

Also, more recently, a fully automated device as described in U.S. patent application Ser. No. 382,483 was used to incubate luciferase reporter cells in 96-well microtiter plates, transfer chemicals and known transcriptional modulators to the cells, incubate cells with the chemicals, remove the chemicals by washing with PBS, add lysis buffer to the cells and measure the bioluminescence produced.

An additional recent improvement is the ability to screen suspension cell lines in the automated high through-put mode using custom manufactured, opaque, 96 well filter plates (Millititer Plates, Millipore Corp.). This involved the manufacture of a robotic filtration and washing station.

RESULTS

A. Validation of the Reporter Cell Lines

1. Southern Blots

Figure 19:
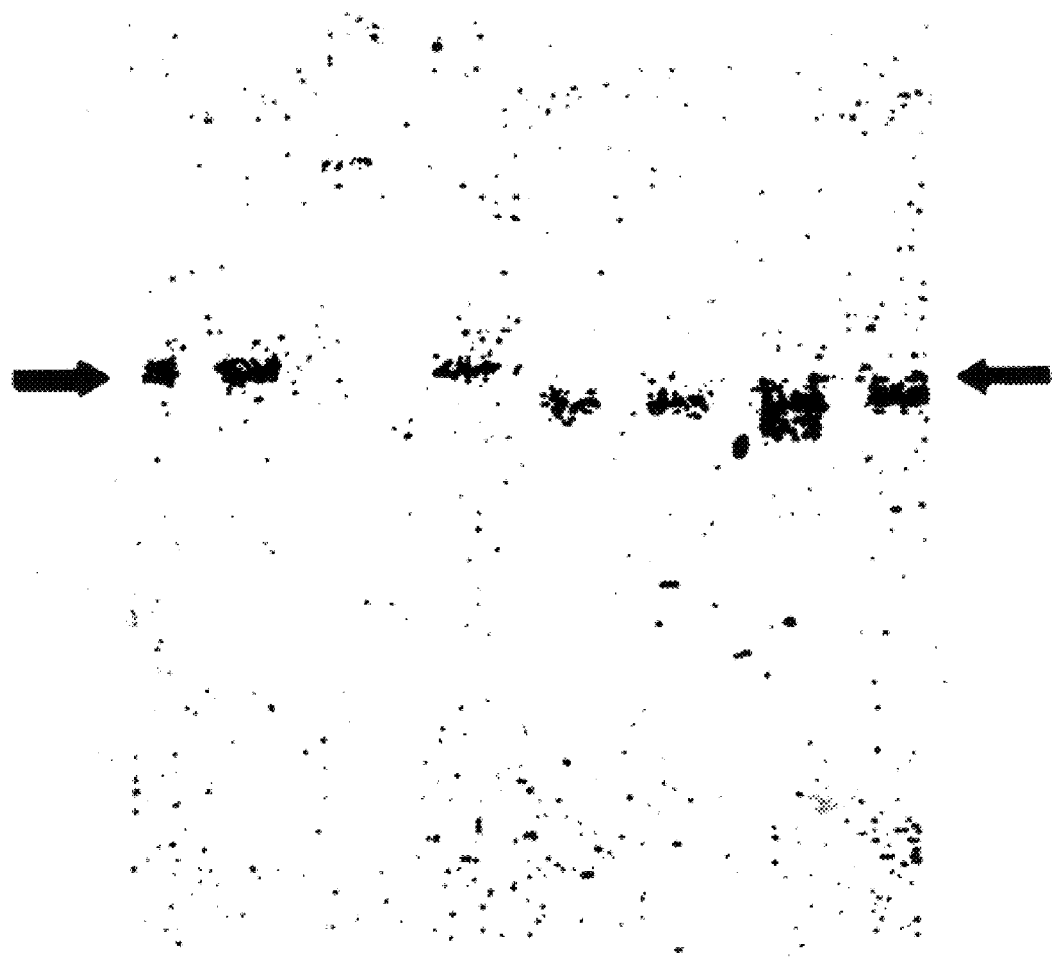
FIG. 19 is an autoradiogram of a Southern blot showing the correct luciferase vector integration of independently isolated SV40 reporter vector transfectants. Lane 1 is a plasmid control. The expected result is a single band of the same molecular weight as the control.
Figure 20:
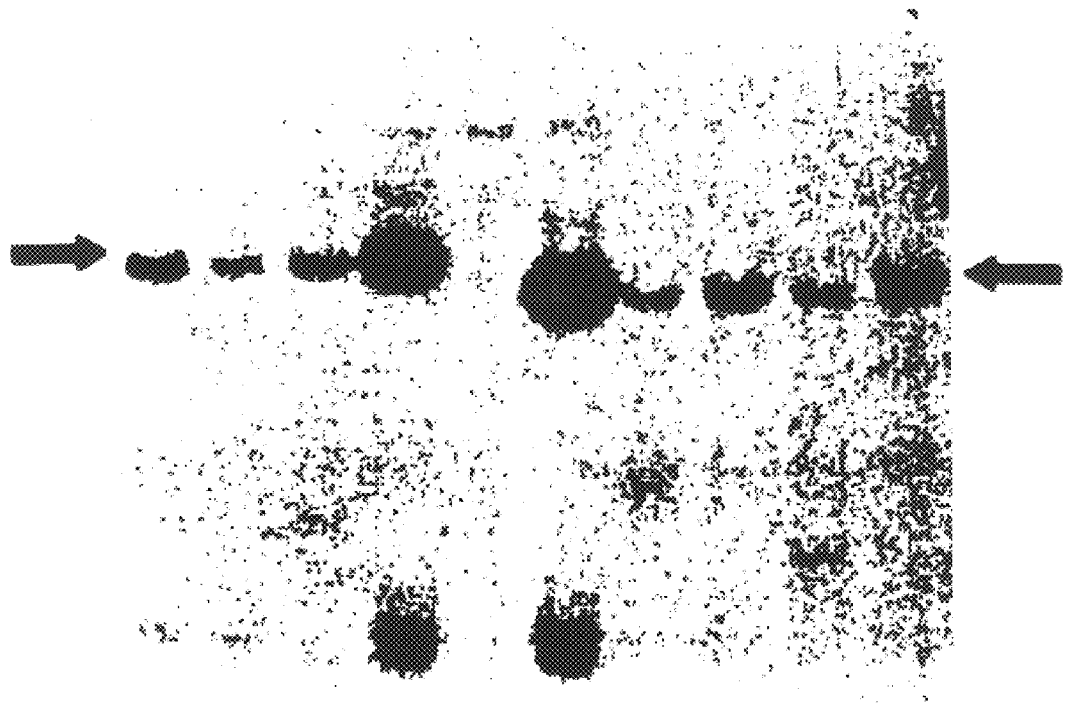
FIG. 20 is an autoradiogram of a Southern blot showing the correct luciferase vector integration of *Ins. D1* isolated CMV reporter vector transfectants. Lane 1 is a plasmid control. The expected result is a single band of the same molecular weight as the control.

Cell clones transfected with the OSI mammalian expression shuttle vector fused to the CMV, SV40 and MMTV promoters were analysed for correct and complete integration of the promoter/luciferase constructs by Southern blotting. Genomic DNA was prepared of each clone to be tested and restriction-cut with Dra I. Since Dra I cuts in the SV40 polyadenylation sites located in the OSI mammalian expression shuttle vector just upstream the inserted promoter sequences as well as downstream of the luciferase coding region, but not in any of the 3 promoter sequences used for generating stably transfected cell clones, a single fragment should be visualized on a blot if an appropriate probe is used. The size of that fragment should be characteristic for each of the three promoter sequences analyzed. The Southern blots were hybridized with either an end labelled luciferase-specific 40 nucleotide oligomer (OSI, ON277), or a random primer labelled DNA fragment corresponding to the 5' third of the luciferase open reading frame (an XbaI-EcoRI fragments of pUV106). FIGS. 19 and 20 show the resulting autoradiograms. All but one of the luciferase expressing clones show the correct characteristic fragment. One of the clones has an extra unexpected fragment that may be the result of two insertion events, one resulting in an intact vector and the other rearranged. We selected a single, correctly integrated clone from each transfection for use in the high throughput screen.

2. Inducer Experiments

Figure 21:
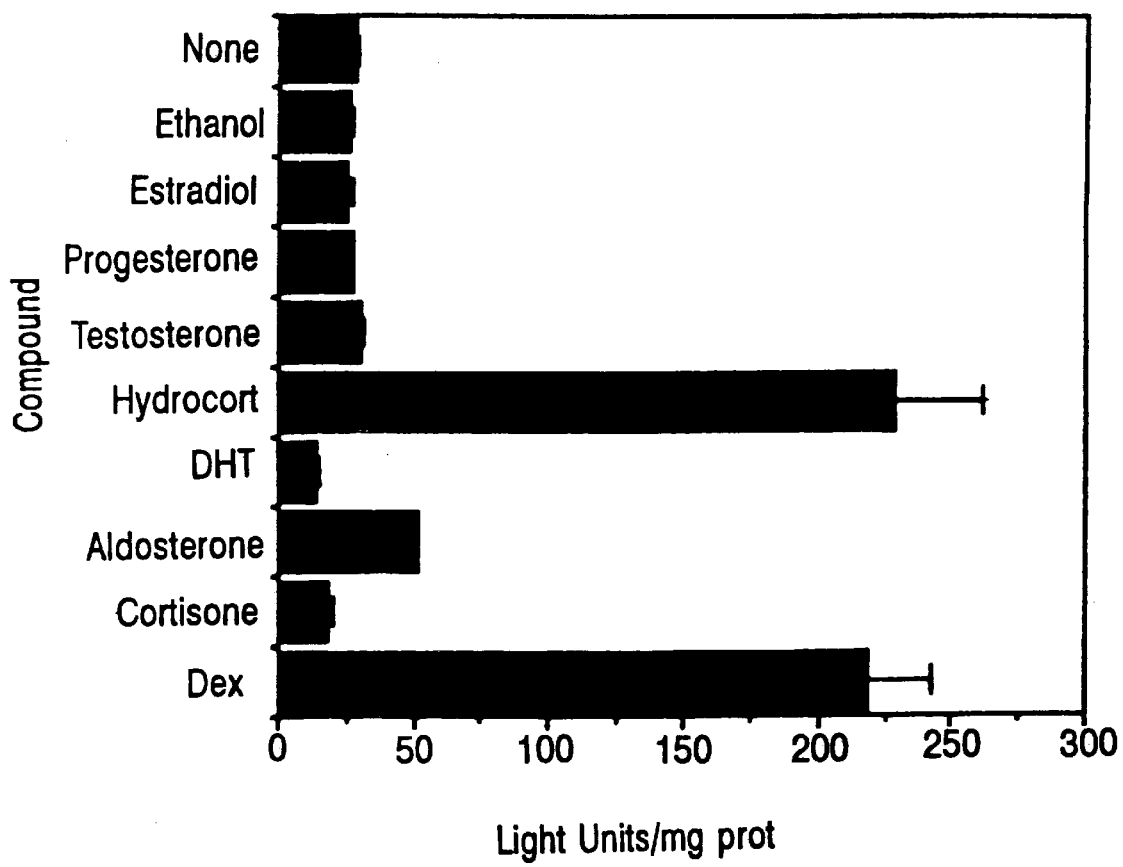
FIG. 21 is a graphical representation of the response of the MMTV reporter cell line to various steriods. Relative light production is compared to an untreated control.

Cell clones with correctly integrated promoter-reporter constructs are routinely analysed for correct reaction to known transcriptional inducers. In the case of the MMTV reporter cell line, M10, the response to steroid hormones is well documented. M10 cells were incubated with several different steroids for 6 hours. The cells were then harvested and assayed for luciferase as described above. The data are shown graphically in FIG. 21. Compared to an untreated control, the MMTV LTR was induced over 10 fold by the steroids known to have active steriod receptors in this cell line. The concentrations of steroids required for maximal induction of luciferase expression were approximately the same as those reported in the literature.

B. In vivo Signal Half-Life of the Luciferase Reporter System

Figure 22:
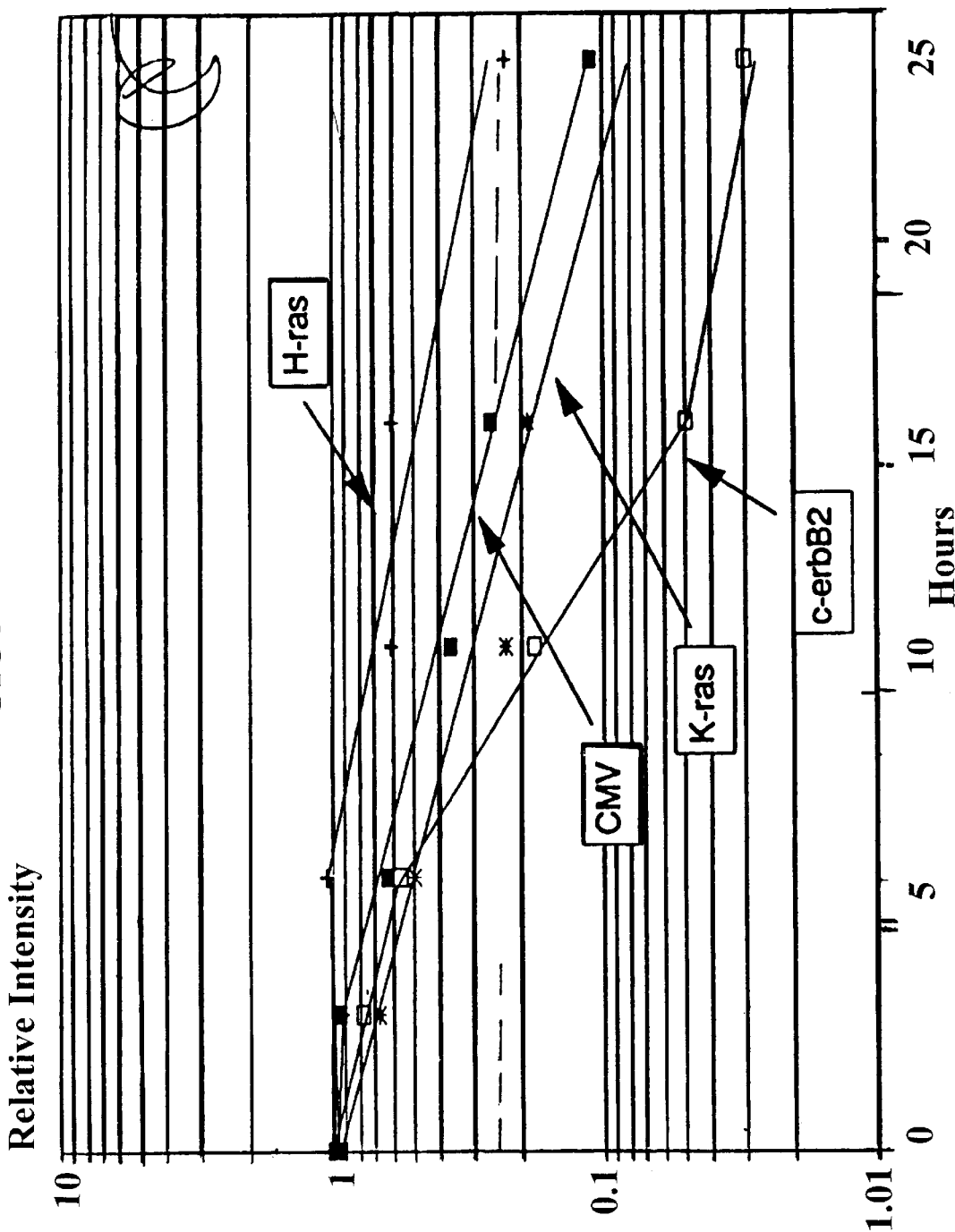
FIG. 22 is a graphical representation of the decay of reporter gene signal after treatment of cells with Actinomycin D. Plotted is relative intensity of the signal versus time after ActD addition.

When screening for inhibitors rather than inducers of transcription, the half-life of the reporter molecule becomes a crucial parameter in determining the minimal incubation time that would be necessary to allow enough decay of reporter molecules so that the inhibition of their synthesis became visible. The CMV reporter cell line was therefore tested for the time dependency of luciferase activity after treatment of the cells with Actinomycin D, an inhibitor of transcription. This experiment measured the combined half-life of luciferase mRNA and of the luciferase protein and compares the rate of signal decay of the CMV reporter to three other well characterized genes; H-ras, K-ras and c-erbB2. Cells derived from clones CM1 (CMV), K2 (K-ras), H21 (H-ras) and N2 (c-erbB2) were seeded into 96-well microtiter plates and incubated overnight. At time 0, Actinomycin D (25 microg/ml) was added. At the times indicated in FIG. 22, cells were washed with PBS and luciferase activity of Actinomycin-treated cells determined as described in Materials and Methods. The signal from the trated cells was compared to the luciferase activity of untreated controls. The logarithm of the treated/untreated ratio was plotted versus time, this data is shown in FIG. 22. The calculated halflife of the signal from each of the four cell lines is shown in table 1. The half-lifes were found to range from about 3 to 10 hours indicating that a 24 hour incubation with a 100% efficient inhibitor of transcription would be sufficient to reduce luciferase levels to 6% of the control in the tested cell lines.

TABLE 1

Halflife Determinations

| Cell Line | Reporter | Signal Halflife |
| --- | --- | --- |
| CM1 | CMV | 6.5 hours |
| K2 | K-ras | 6.5 hours |
| H21 | H-ras | 10 hours |
| N2 | neu | 3 hours |

C. Luciferase Expression Assay in Yeast

Figure 23:
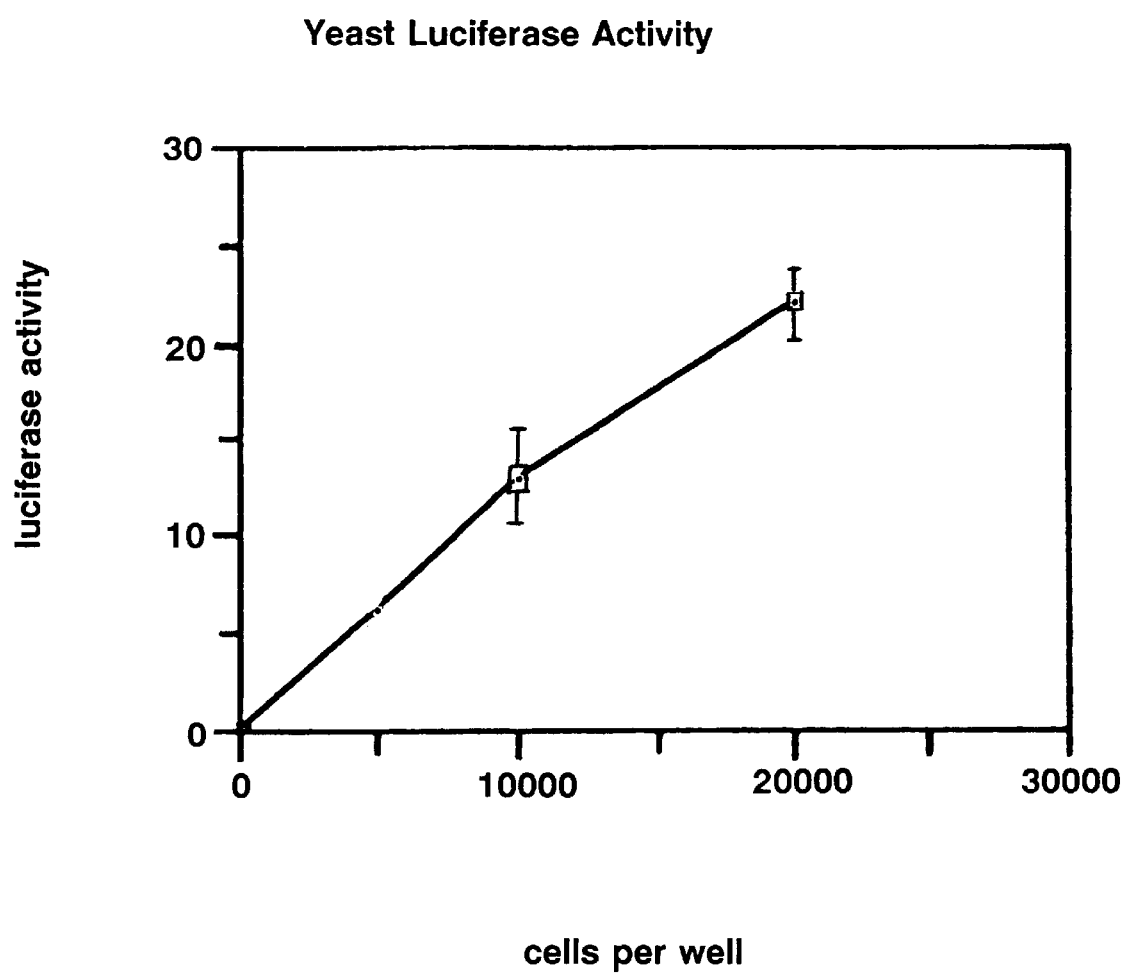
FIG. 23 is a graphical representation of the linearity of response of the yeast luciferase reporter system. Light intensity versus cell number is plotted.

The yeast expression plasmid carrying the luciferase gene under control of a yeast promoter was transfected into appropriate yeast cells. Using these cells as a model system, a format for a 96-well luciferase expression assay in yeast cells was developed as described in more detail in Materials and Methods. Luciferase activity was assayed essentially as described by De Wet et al. (1987) using a modified single step lysis-assay buffer which contained Lyticase, to break down the yeast cell wall, and the detergent Brij 58, to help effect lysis. Cells were grown in custom made, 96 well microtiter plates equipped with membrane-type filter bottoms. These plates retain liquid until vacuum is applied. Medium was removed by filtration, and the cells were washed with PBS. The lysis/assay buffer was added and resulting luminescence measured in a luminometer. Representative data are shown in FIG. 23. This simple assay is reliable and sensitive. Small changes in luciferase expression from as few as 5,000 yeast cells was easily detected.

G. Quality Assurance Analysis

Figure 24:
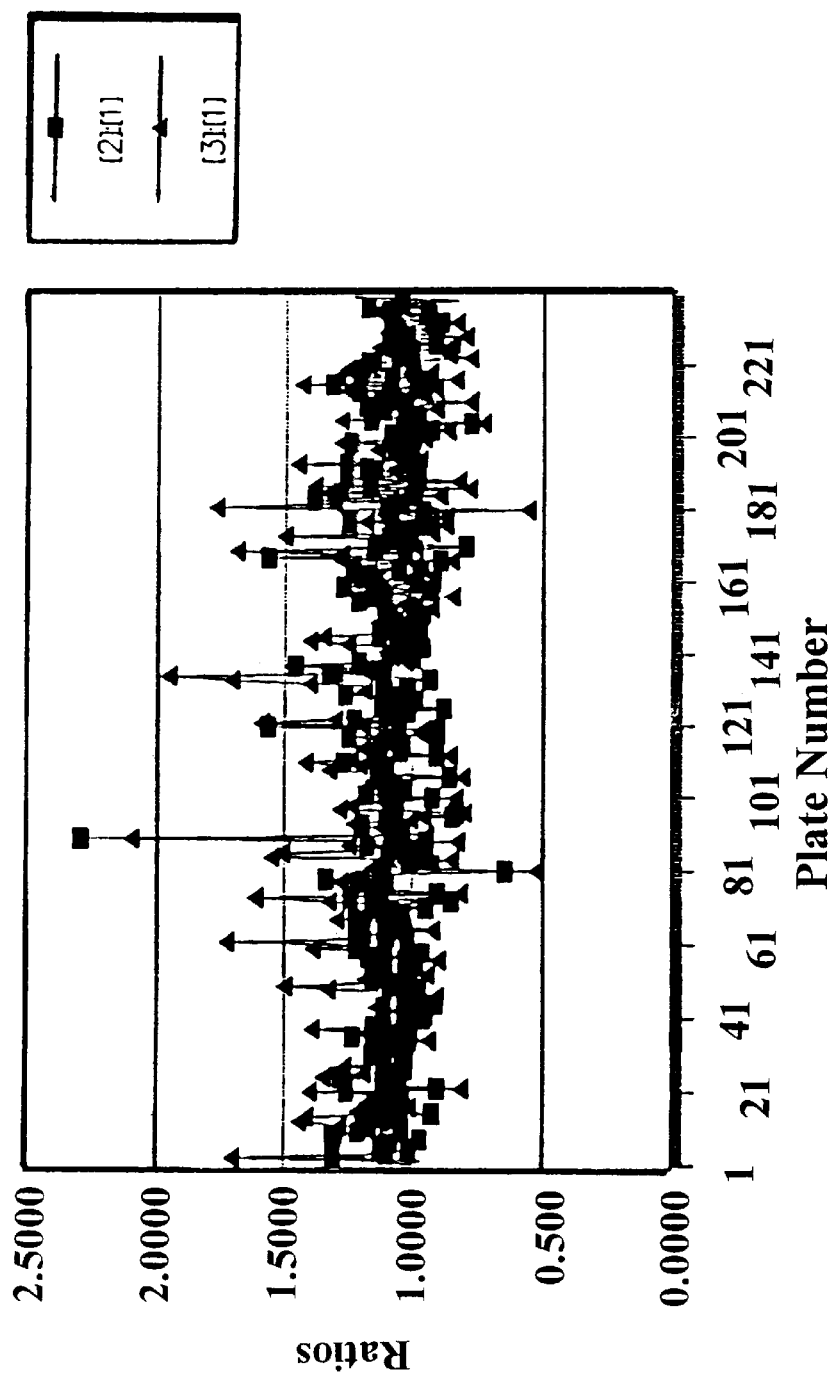
FIG. 24 is a quality assurance analysis of a high throughput screen measuring the ratios of negative values at various positions within a plate. The expected value is 1.0.
Figure 25:
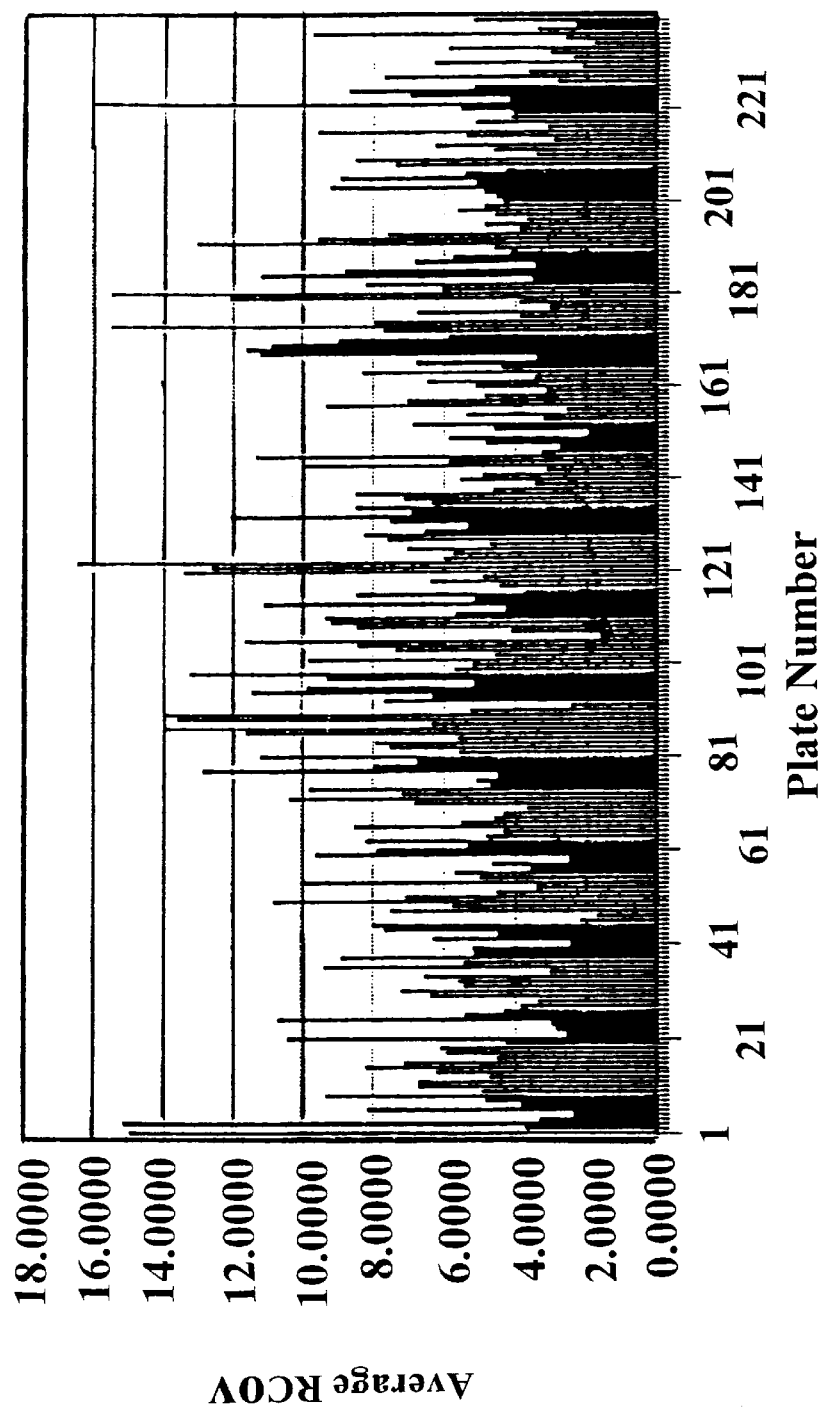
FIG. 25 is a quality assurance analysis of a high throughput screen measuring a robustified coefficient of varience for the negative controls on a number of plates. Values less than 10 are acceptable.
Figure 26:
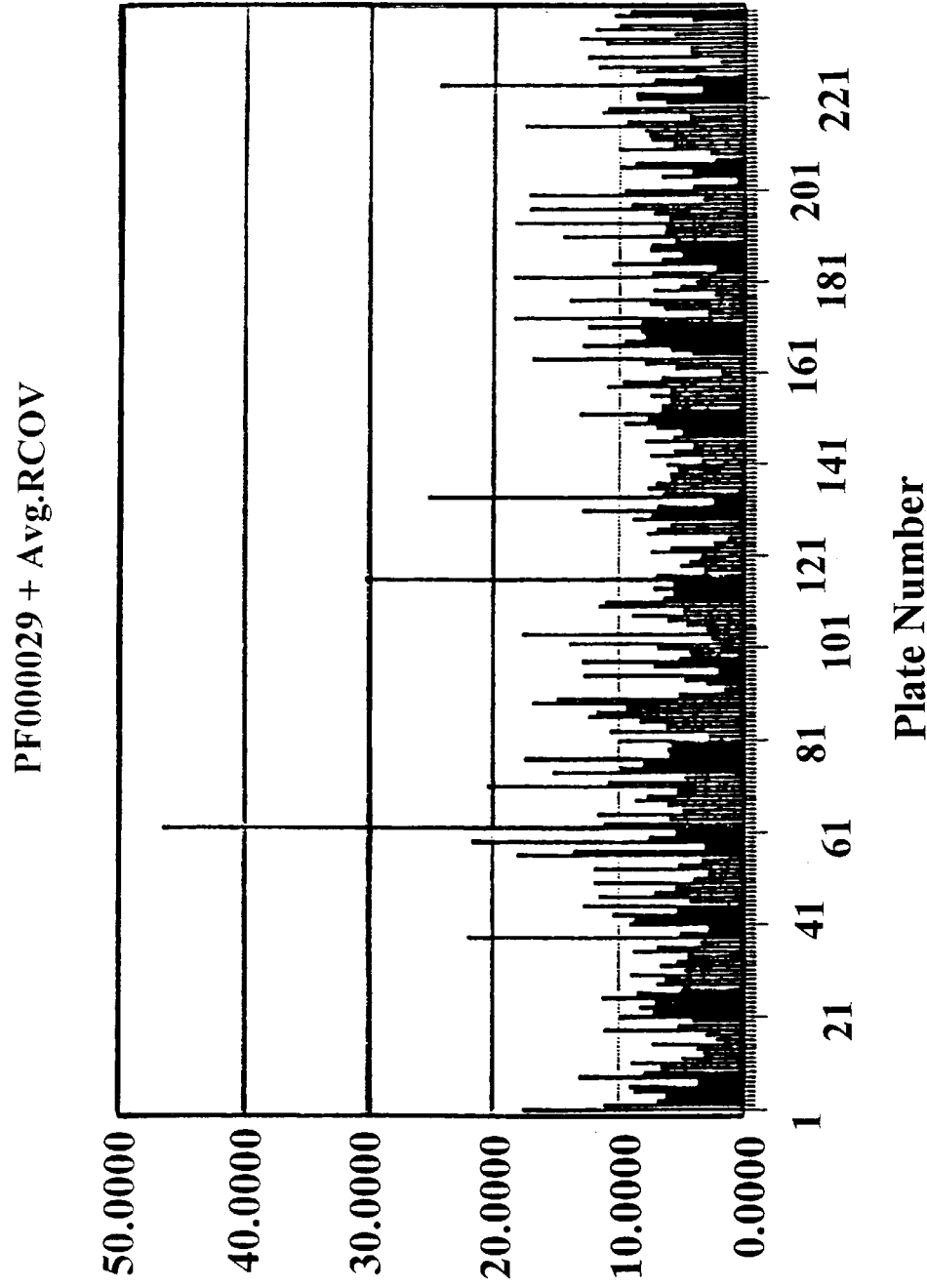
FIG. 26 is a quality assurance analysis of a high throughput screen measuring a robustified coefficient of varience for the positive controls on a number of plates. Values less than 10 are acceptable.
Figure 27:
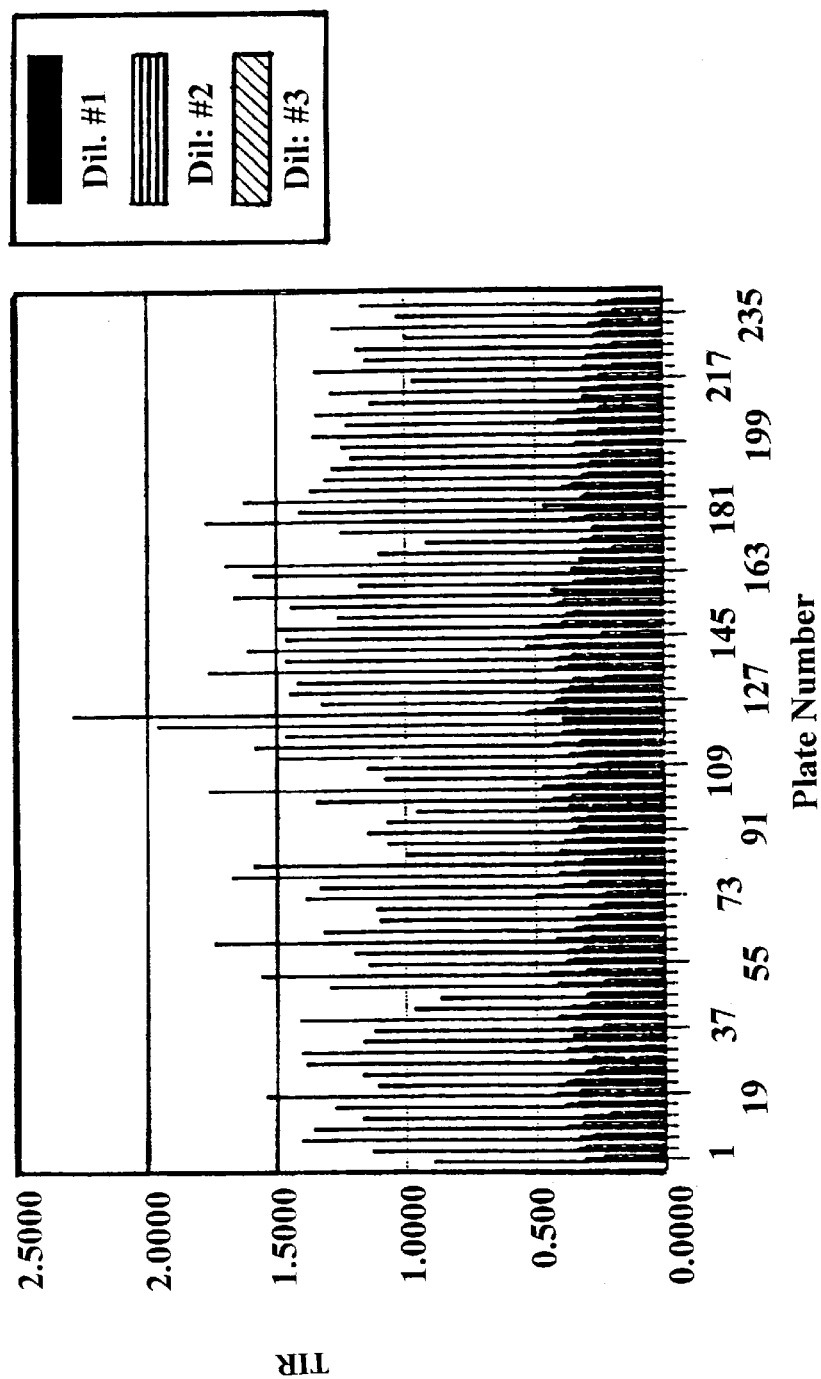
FIG. 27 is a quality assurance analysis of a high throughput screen measuring a response of a reporter cell line to three different concentrations of a compound known to induce transcription.

A number of quality assurance criteria are routinely assessed during the course of high throughput screens. Data from QA analysis of a portion of Screen IV are shown in FIGS. 24–27. FIG. 24 shows an analysis of the consistency of the luciferase signal on various areas of each plate. The ratios of negative control values from three different areas within each plate are calculated and plotted versus plate number. The expected value is 1.0. Values greater than 1.5 or less than 0.4 indicate uneven signal generation across the plate. In this example 240 plates, representing 1440 compounds, tested against three cell lines, are shown. The coefficient of variance for the 12 negative control values from each of the same 240 plates are represented by the data shown in FIG. 25. Values less than 20% are considered acceptable. Similar data for the 12 positive control values of the same plates are shown in FIG. 26. FIG. 27 shows the transcription induction ratio (TIR) for the positive controls of one cell line represented in the same set of 240 plates. The TIR is the ratio of the experimental values to the untreated controls. In this case the cell line is the K-ras reporter and the positive control is Actinomycin D a potent general inhibitor of transcription. Three values are shown for each plot, representing three different concentrations of Actinomycin D. The expected value for such an analysis depends on the other half life of the signal and the incubation time (here 24 hours), but for this combination, typical values range from 0.4 to 0.3 fold.

C. High-Throughput Screen

1. Screen I

In an initial high throughput screen (Screen I), 500 compounds, consisting of 96 fermentation broths and 404 pure chemicals, were tested against a G-CSF (G1002) reporter cell line and an MMTV reporter control cell line.

The number of lead compounds identified in this screen are shown in table 2.

TABLE 2

SUMMARY OF HIGH THROUGHPUT SCREEN I

Number (%) of Chemicals Which Activate Expression:

|  | 2–3X | 3–5X | 5–7X | 7–10X | >10X | Total |
|---|---|---|---|---|---|---|
| G-CSF | 0 | 2 | 0 | 0 | 0 | 2 |
|  | (0%) | (0.4%) | (0%) | (0%) | (0%) | (0.4%) |
| MMTV | 2 | 2 | 3 | 1 | 1 | 9 |
|  | (0.4%) | (0.4%) | (0.6%) | (0.2%) | (0.2%) | (1.8%) |

CYTOTOXIC COMPOUNDS: 5 (1%)

2. Screen II

An additional high throughput screen assayed aqueous clarified supernatants derived from individual Actinomyces colonies prepared by standard methods, as well as corresponding methanol extracts. These two sample types were subjected at 1:10 initial dilution to a fully automated, robotic High-Throughput luciferase assay using the system described in U.S. patent application Ser. No. 382,483. Out of 356 samples tested for modulation of the G-CSF, GM-CSF (both as specificity controls) and the MMTV promoters, 25 samples scored as positives, 7 of which were promoter-specific. A summary of the obtained results is contained in Tables 3 and 4.

TABLE 3

Promoter/Luciferase Pilot Screen
of Fermentation Broth Samples
Lead Samples

|  | Promoter/TIR | | | Number of Hits | |
|---|---|---|---|---|---|
| Fermentation Broths | G | GM | MTV | Inducers | Inhibitors |
| methanol extracts: | >2.0 | | | 0 | |
| 176 total | <0.6 | >0.8 | >0.8 | | 0 |
|  |  | >2.0 |  | 1 |  |
|  | >0.8 | <0.6 | >0.8 |  | 0 |
|  |  |  | >2.5 | 7 |  |
|  | >0.8 | >0.8 | <0.6 |  | 0 |
| aqueous fractions: | >2.0 | | | 7 | |
| 180 total | <0.6 | >0.8 | >0.8 | | 0 |
|  |  | >1.8 |  | 1 |  |
|  | >0.8 | <0.6 | >0.8 |  | 1 |
|  |  |  | >2.4 | 8 |  |
|  | >0.8 | >0.8 | <0.6 |  | 0 |

TABLE 4

Promoter/Luciferase Pilot Screen
of Fermentation Broth Samples
Promoter-Specific Leads

|  | Promoter/TIR | | | Number of Specific Leads | |
|---|---|---|---|---|---|
| Fermentation Broths | G | GM | MTV | Inducers | Inhibitors |
| methanol extracts: | >2.0 | <1.8 | <1.8 | 0 | |
| 176 total | <0.6 | >0.8 | >0.8 |  | 0 |
|  | <1.8 | >2.0 | <1.8 | 0 |  |
|  | >0.8 | <0.6 | >0.8 |  | 0 |
|  | <1.8 | <1.8 | >2.5 | 4 |  |
|  | >0.8 | >0.8 | <0.6 |  | 0 |
| aqueous fractions: | >2.0 | <1.8 | <1.8 | 0 | |
| 180 total | <0.6 | >0.8 | >0.8 |  | 0 |

TABLE 4-continued

Promoter/Luciferase Pilot Screen
of Fermentation Broth Samples
Promoter-Specific Leads

|  | Promoter/TIR | | | Number of Specific Leads | |
|---|---|---|---|---|---|
| Fermentation Broths | G | GM | MTV | Inducers | Inhibitors |
|  | <1.8 | >1.8 | <1.8 | 0 | |
|  | >0.8 | <0.6 | >0.8 |  | 1 |
|  | <1.8 | <1.8 | >2.4 | 2 |  |
|  | >0.8 | >0.8 | <0.6 |  | 0 |

3. Screen III

Figure 28:
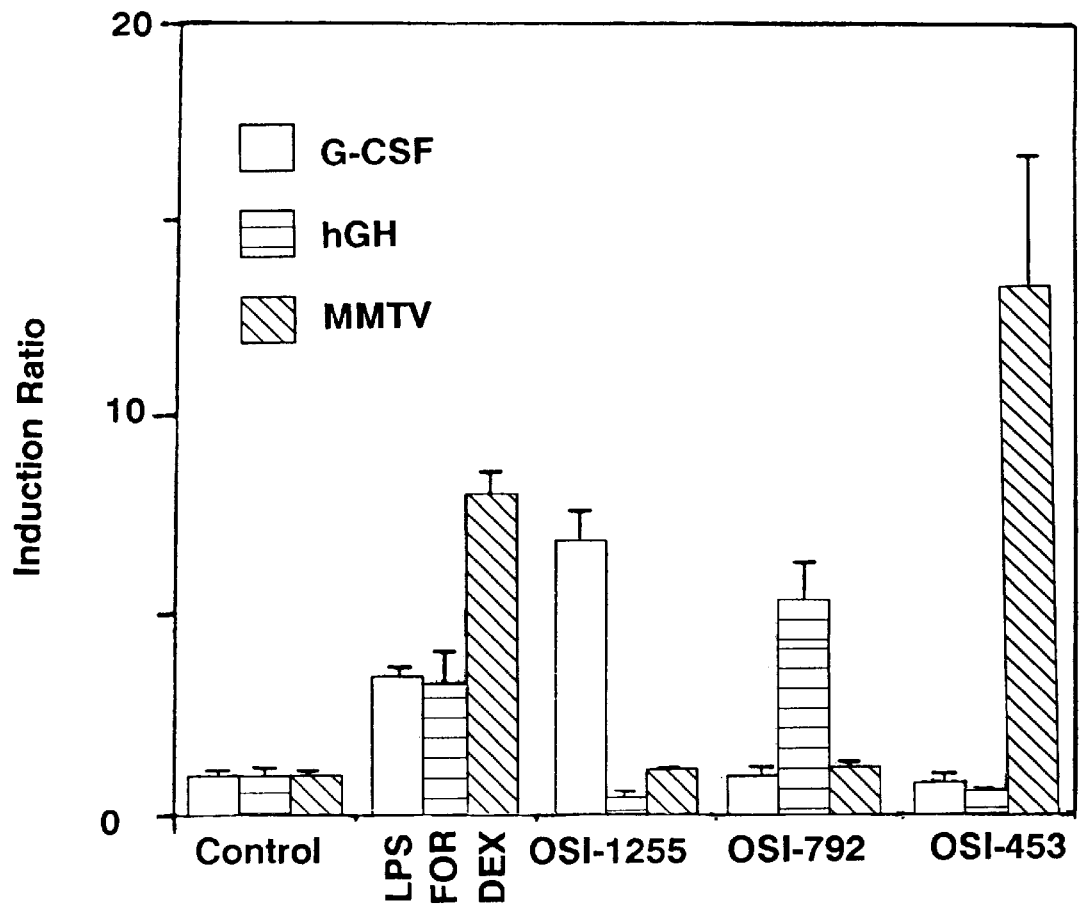
FIG. 28 is a bar graph illustrating specific induction of luciferase expression in reporter cell lines for MMTV (M10), human growth hormone (532) and human G-CSF (G21) promoters in response to chemicals identified in a high throughput screen and known transcriptional inducers.
Figure 29:
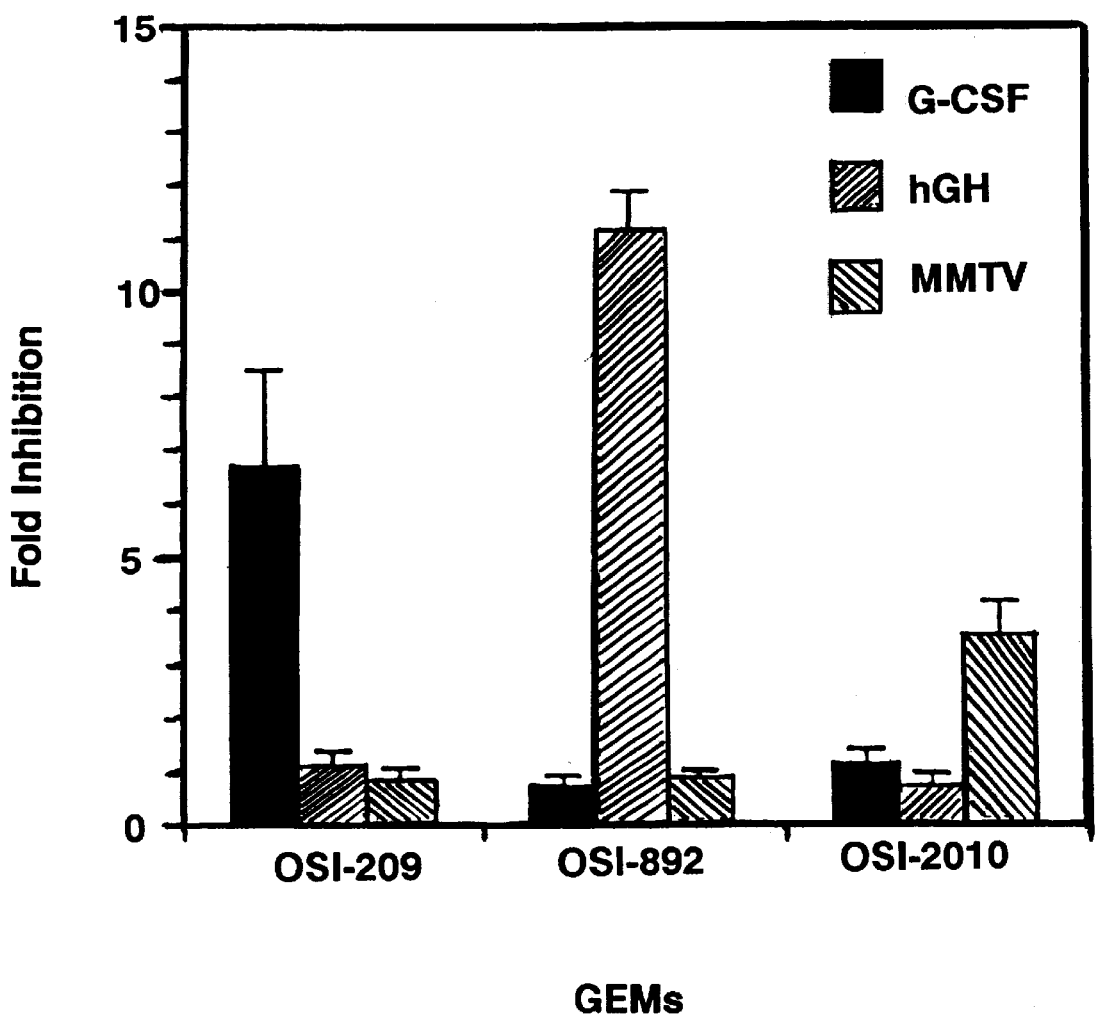
FIG. 29 is a bar graph illustrating specific inhibition of luciferase expression in reporter cell lines for MMTV (M10), human growth hormone (532), and human G-CSF (G21) in response to chemicals identified in a high throughput screen.

Table 5 shows a summary of the results of a one-week, high-throughput screen of 2,000 chemicals to identify those chemicals specifically stimulating or inhibiting transcription from the MMTV, G-CSF or human Growth Hormone (the last two as controls for specificity) promoters. This screen as with the other screens, concurrently tested chemicals at three concentrations on quadruplicate samples of the M10, 532 and G21 cell lines. A minimum stimulation of one promoter, to the degree indicated, and less than 50% activation of the other promoter was required for a chemical to be considered a selective activator. A minimum inhibition of 3 fold of one promoter and less than 20% inhibition of the other promoter was required for a chemical to be considered a selective inhibitor. Chemicals which scored as positive in this screen are identified in Table 6. FIG. 28 illustrates the transcriptional stimulation and FIG. 29 the transcriptional inhibition observed with some of the lead chemicals.

TABLE 5

SUMMARY OF HIGH-THROUGHPUT SCREEN III

Number (%) of Chemicals Which Activate Expression:

|  | 2–3X | 3–5X | 5–7X | 7–10X | >10X | Total |
|---|---|---|---|---|---|---|
| G-CSF | NA | 23 | 10 | 3 | 2 | 38 |
|  |  | (1.1%) | (0.5%) | (0.15%) | (0.10%) | (1.9%) |
| MMTV | 15 | 1 | 0 | 1 | 1 | 18 |
|  | (0.7%) | (0.05%) | (0%) | (0.05%) | (0.05%) | (0.9%) |
| hGH | NA | NA | 12 | 5 | 6 | 23 |
|  |  |  | (0.6%) | (0.03%) | (0.03%) | (1.14%) |

Number (%) of Chemicals Which Inhibit Expression >3 Fold

Promoter
G-CSF 7 (0.35%)
MMTV 1 (0.05%)
hGH 42 (2.1%)

To determine the number of lead chemicals, which reproducibly score as positives in repeated luciferase assays, two types of experiments were conducted:

1) G-CSF lead chemicals #1780, #58, #1783, #1374 were subjected to 48 independent luciferase assays performed on the same day. Compounds #58, #1780 and #1374 scored as positives in every single one of these assays inducing luciferase expression between 2 and 28 fold (#58), 20 and 80 fold (#1780) and 5 and 40 fold (#1374). Probably due to its relatively low induction of luciferase expression (1.5 to 8 fold), Compound #1783 scored as positive only in half of the 48 repeat assays.

2) All of the 18 lead chemicals inducing luciferase expression from the MMTV promoter were again subjected to luciferase assays: 10 chemicals (#453, #519, #562, #765,

828, #848, #1269, #1316, #1384 and #2148) (Table 6) again induced luciferase expression between 2.1 and 2.8 fold. Probably due to the relatively low induction level close to the background of the assay, the other eight lead chemicals did not repeat on that particular day. The most prominent lead chemical, #453 (13.3 fold induction in the original high-throughput assay), was repeated in a total of 3 independent assays and consistently induced luciferase expression from the MMTV promoter between 10 and 35 fold. Replacing DMSO by methanol to dissolve the chemical did not affect its ability to activate the MMTV promoter.

TABLE 6

| Chemical # | Chemical Name | FOLD INDUCTION RELATIVE TO SOLVENT CONTROL | | |
|---|---|---|---|---|
| | | GCSF | hGH | MMTV |
| A) SCREEN III TRANSCRIPTIONAL ACTIVATORS | | | | |
| G-CSF: | | | | |
| 40 | 3-Acetyl-2-6-Bis(tertiary butyl amino)-4-methyl-pyridine | 5.62 | 0.62 | 0.27 |
| 58 | 1-Acetylimidazole | 6.03 | 0.17 | 0.42 |
| 237 | N-Carbethoxy-phthalimide | 4.77 | 0.06 | 0.62 |
| 254 | 1-(2-Chloroethyl)piperidine | 4.09 | 0.90 | 0.98 |
| 364 | Melamine | 3.67 | 1.18 | 1.07 |
| 473 | 1,3,5,-Triazine | >3 | 0.50 | 0.87 |
| 542 | 5-Bromo-2'-deoxycytidine | 6.28 | 1.08 | 1.26 |
| 543 | 5-Bromo-2'-deoxyuridine | 7.17 | 0.72 | 0.98 |
| 878 | Blueberry leaf extract | 3.84 | 1.17 | 0.78 |
| 1025 | Culvers Root extract | 4.09 | 0.98 | 1.24 |
| 1234 | 4-Aminocinnamic Acid hydrochloride | 4.97 | 0.51 | 1.03 |
| 1255 | 1-Bromo-3,5-dichlorobenzene | 6.74 | 0.43 | 1.09 |
| 1374 | 4'-Amino-N-methylacetanilide | 11.03 | 0.05 | 1.05 |
| 1375 | 4'-(aminomethyl)benzene sulfonamide hydrochloride | 8.94 | 0.04 | 1.37 |
| 1376 | 2-Amino-5-Methyl benzene sulfonic acid | 6.37 | 0.04 | 1.32 |
| 1397 | 5-Amino-3-methylisothiazole hydrochloride | 3.63 | 0.57 | 1.13 |
| 1482 | 2-Aminophenyl disulfide | 3.99 | 0.54 | 1.07 |
| 1483 | 4-Aminophenyl disulfide | 4.64 | 0.38 | 1.09 |
| 1521 | 2-Amino-6-purinethiol | 3.59 | 0.73 | 0.92 |
| 1583 | 8-Bromoadenosine | 5.82 | 0.12 | 0.88 |
| 1592 | Bis(2,2,3,3,4,4,5,5,6,6,7,7,)dodecafluoroheptyl-(+)-camphorate | 3.20 | 0.74 | 1.34 |
| 1783 | Cupferron | 6.55 | 0.32 | 0.89 |
| 1793 | Cyanomethyl-N,N-dimethyl dithiocarbamate | 9.50 | 0.52 | 1.21 |
| 1994 | 3-Bromobiphenyl | 3.29 | 0.34 | 0.63 |
| 2001 | 1-Bromo-4-tertiary butyl benzene | 3.11 | 0.74 | 1.12 |
| 2030 | 4-Bromo-2-fluoro-6-nitroanizol | 5.53 | 0.67 | 0.87 |
| 2096 | (+)-1-Bromo-3-Chloro-2methyl propane | 3.27 | 0.61 | 0.89 |
| 2097 | 1-Bromo-5-Chloro pentane | 5.09 | 0.88 | 1.22 |
| 2129 | 4-Chlorobenzyl Chloride | 3.23 | 0.75 | 0.95 |
| GROUP A: | | | | |
| 378 | 7-Oxo-7H-benzo[e]perimidine 4-carboxylic acid | 4.12 | 0.26 | 0.59 |
| 423 | Quinacrine dihydrochloride hydrate | 2.39 | 0.56 | 0.64 |
| 427 | Resazurin | 3.14 | 0.43 | 0.71 |
| 836 | Thionin | 3.20 | 0.23 | 0.58 |
| 1776 | Cresyl Violet Acetate | 3.50 | 0.15 | 1.36 |
| 1904 | 9-Aminoacridine hydrochloride | 4.12 | 0.54 | 0.82 |
| GROUP B: | | | | |
| 670 | Methyl Green | >3 | 0.52 | 0.79 |
| 1780 | Crystal Violet | 20.39 | 0.38 | 1.15 |
| GROUP | | | | |

TABLE 6-continued

| Chemical # | Chemical Name | FOLD INDUCTION RELATIVE TO SOLVENT CONTROL | | |
|---|---|---|---|---|
| | | GCSF | hGH | MMTV |
| A AND B: | | | | |
| 80 | Acridine Orange | 5.87 | 0.66 | 0.83 |
| hGH: | | | | |
| 70 | 2-Acetylpyrrole | 0.43 | 9.26 | 0.85 |
| 299 | 10,11-Dihydrocarbamazepine | 0.53 | 5.46 | 0.47 |
| 322 | 1-ethyl-2-benzimidazolinone | 0.60 | 11.18 | 1.12 |
| 325 | Fisetin | 0.14 | 5.42 | 1.0 |
| 552 | 3-(4-chlorophenyl)-1-methoxy-1-methyl urea | 0.81 | 5.31 | 0.86 |
| 790 | Rivanol | 0.01 | 5.94 | 0.58 |
| 792 | Rose Bengal | 0.94 | 5.31 | 1.21 |
| 856 | Tripa$\mu$mitin | 0.28 | 6.49 | 0.42 |
| 1004 | Arnica 4x | 0.85 | 6.48 | 1.22 |
| 1160 | Rochester # 6180 | 0.38 | 5.79 | 0.80 |
| 1251 | Bromocresol Green | 0.14 | 15.19 | 0.33 |
| 1337 | 4-Amino-5-hydroxy-1-naphthalene sulfonic acid | 0.07 | 15.87 | 0.23 |
| 1499 | 2-Amino-4-phenylthiazole hydrobromide monohydrate | 0.24 | 5.55 | 0.61 |
| 1550 | 2-Aminothiazole | 0.04 | 5.44 | 0.87 |
| 1552 | 2-amino-2-thiazoline | 1.23 | 7.26 | 0.52 |
| 1561 | 4-Amino-3,5,6-trichloropicolinic acid | 0.23 | 8.05 | 0.48 |
| 1598 | N,N'-Bis-[3-(4,5-dihydro-1H-imidizol-2-yl)phenyl] urea dipropanoate | 0.72 | 5.32 | 1.27 |
| 1678 | 4,8-Bis(hydroxymethyl)-tricyclo [5,2,1,0$^{2.6}$]decane | 0.36 | 7.08 | 0.89 |
| 1740 | 5-carbethoxy-2-thiouracil | 0.74 | 17.77 | 0.87 |
| 1747 | $N_6$-carbobenzyloxy-L-lysine | 0.78 | 6.16 | 0.86 |
| 1804 | Cyclobutane carboxylic acid | 1.05 | 9.41 | 0.49 |
| 1876 | Alec Blue | 0.87 | 11.91 | 0.40 |
| 1881 | Alizarin Blue Black B | 0.21 | 18.87 | 0.69 |
| MMTV: | | | | |
| 189 | Bathocuproinedisulfonic Acid disodium salt hydrate | 1.06 | 1.47 | 2.80 |
| 453 | 2,2':6',2"-Terpyridine | 0.79 | 0.58 | 13.30 |
| 519 | b-Apo-8'-carotenal | 1.15 | 0.68 | 2.76 |
| 562 | Copaiva Balsam | 1.10 | 0.15 | 2.34 |
| 629 | Homoveratric acid | 0.85 | 1.05 | 2.48 |
| 633 | 5-Iodorotic acid | 1.02 | 0.86 | 2.46 |
| 765 | Prednisolone-21-Acetate | 0.96 | 1.30 | 2.66 |
| 828 | 2,4,5,4'-Tetrachlorodiphenyl-sulfide | 1.47 | 1.34 | 2.20 |
| 848 | Triamcinolone acetonide | 0.75 | 1.28 | 2.43 |
| 944 | Peanut | 1.15 | 0.91 | 2.10 |
| 1269 | 5-Amino-4,6-dichloropyrimidine | 0.72 | 0.91 | 2.18 |
| 1316 | 2-Aminofluorene | 0.74 | 1.39 | 2.33 |
| 1318 | 2-Amino-9-fluorenone | 1.13 | 0.85 | 2.41 |
| 1384 | 2-Amino-4'-methylbenzo-phenone | 1.33 | 0.50 | 2.43 |
| 1573 | 5-Bromoacenapthene | 1.49 | 0.34 | 4.30 |
| 2064 | 4-(Bromomethyl)-6,7-dimethoxy-coumarin | 0.82 | 1.10 | 2.53 |
| 2148 | 2-chlorocyclohexanone | 0.45 | 0.92 | 2.82 |
| 2191 | Chloramphenicol | 0.37 | 0.35 | 7.32 |
| B) SCREEN III TRANSCRIPTIONAL INHIBITORS | | | | |
| G-CSF: | | | | |
| 209 | 4-Benzoylpyridine | 6.66 | 1.08 | 0.81 |
| 371 | Morin hydrate | 11.11 | 0.41 | 0.89 |
| 660 | Maclurin | 10.0 | 0.34 | 1.04 |
| 798 | Salicylamide | 4.76 | 0.90 | 0.68 |
| 2009 | 4-Bromo-3,5-dimethylpyrazole | 3.70 | 0.57 | 0.64 |
| 2082 | 4-Bromo-3-Methylpyrazole | 5.26 | 0.65 | 1.23 |
| 2121 | 3-Chlorobenzyl alcohol | 4.76 | 0.40 | 1.14 |

TABLE 6-continued

| Chemical # | Chemical Name | FOLD INDUCTION RELATIVE TO SOLVENT CONTROL | | |
|---|---|---|---|---|
| | | GCSF | hGH | MMTV |
| hGH: | | | | |
| 183 | Auramine O | 0.72 | 4.00 | 0.70 |
| 240 | Carminic acid | 0.63 | 5.26 | 0.80 |
| 443 | Sulfamethazine | 0.60 | 4.76 | 0.79 |
| 512 | Amaranth | 0.81 | 5.26 | 0.68 |
| 541 | 5-Bromo-4-Chloro-3-indoxyl-phosphate K-salt | 0.90 | 6.25 | 0.86 |
| 556 | Chromazurol S | 0.73 | 33.33 | 0.87 |
| 561 | Clove Oil | 0.62 | 5.00 | 0.05 |
| 577 | Na—Ne-Diacetyl-L-lysine | 0.64 | 4.00 | 0.68 |
| 578 | Dibenzoyl-D-tartaric acid | 0.65 | 4.00 | 0.91 |
| 630 | Hydantoin-5-acetic acid | 0.70 | 3.57 | 0.74 |
| 640 | Kernechtrot | 0.64 | 5.00 | 0.59 |
| 759 | Piperidine | 0.64 | 5.88 | 0.95 |
| 764 | Prednisolone | 0.82 | 4.54 | 0.59 |
| 875 | Black Walnut extract | 0.69 | 6.25 | 0.80 |
| 892 | Colts Foot Leaves extract | 0.68 | 11.11 | 0.87 |
| 893 | Comfrey Leaf extract | 0.74 | 11.11 | 0.90 |
| 920 | Horehound Herb extract | 0.56 | 3.84 | 0.84 |
| 921 | Horsetail Grass extract | 0.72 | 3.44 | 0.86 |
| 942 | Pau D'Arco extract | 0.80 | 6.25 | 0.63 |
| 970 | Thyme extract | 0.57 | 4.34 | 1.07 |
| 1591 | 1,2-Bis(di-p-tolylphosphino)-ethane | 0.56 | 5.55 | 0.96 |
| 1604 | 2,4-Bis(5,6-bis(4-sulfophenyl)-1,2,4-Triazine-3-yl)-pyridine, tetrasodium salt hydrate | 0.77 | 5.00 | 0.97 |
| 1635 | [(15)-endo]-(–)-Borneol | 0.71 | 9.09 | 0.99 |
| 1640 | 1,2-Bis(2-pyridyl)-ethylene | 0.79 | 5.00 | 0.59 |
| 1641 | 2,3-Bis(2-pyridyl)-pyrazine | 0.83 | 5.55 | 0.60 |
| 1648 | 2-[5,6-Bis(4-sulfophenyl)-1,2,4-triazine-3-yl]-4-(4-sulfophenyl)-pyridine, trisodium salt | 0.86 | 7.69 | 1.00 |
| 1651 | Bis(2,2,2-trifluoroethyl) (methocarbonyl-methyl)-phosphonate | 0.69 | 3.57 | 0.70 |
| 1655 | 2,5-Bis(trifluoro-methyl)benzoic acid | 0.54 | 4.76 | 0.81 |
| 1703 | 3-Bromobenzonitrile | 0.76 | 10.00 | 0.90 |
| 1704 | 4-Bromobenzonitrile | 0.77 | 4.16 | 0.94 |
| 1705 | 4-Bromobenzophenone | 0.54 | 14.28 | 0.62 |
| 1712 | Calcein Blue | 0.74 | 8.33 | 0.94 |
| 1720 | (15)-(–)-Camphor | 0.65 | 4.76 | 0.66 |
| 1764 | 7-(Carboxymethoxy)-4-Methylcoumarin | 0.55 | 7.14 | 0.82 |
| 1770 | Carminic acid | 0.54 | 10.00 | 0.57 |
| 1771 | L-Carnosine | 0.71 | 10.00 | 0.72 |
| 1773 | O-Cresolphthalein Complexone | 0.62 | 10.00 | 0.67 |
| 1890 | Alloxazine | 0.80 | 5.26 | 0.58 |
| 2035 | 5-Bromofuroic acid | 0.57 | 7.14 | 0.89 |
| 2036 | 8-Bromoguanosine | 0.58 | 4.34 | 0.81 |
| 2037 | 1-Bromohexadecane | 0.51 | 4.00 | 0.50 |
| MMTV: | | | | |
| 2010 | 2-Bromo-4,6-dinitroaniline | 0.80 | 0.63 | 3.57 |

4. Screen IV

Table 7 presents the data from one more high throughput screen. In this case the data are from a three week high throughput screen of 2334 compounds. Three cell lines were utilized; CM1 (the CMV reporter cell line). N2 (the c-erbB2 reporter cell line) and K2 (the K-ras reporter cell line), both used as controls for specificity. Each compound was assayed at three concentrations in quadruplicate. Each microtiter plate included a negative control row (no added compound) and a positive control row (Actinomycin D at three concentrations). The data are reported as TIR (transcription induction ratio) which is the median of the samples quadruplicate values divided by the median of the negative control values. In this case, transcriptional inhibitors and inducers are sought, so the selection criteria for lead compounds is that the test promoter be inhibited to 0.4 or induced to 1.8× of the negative control while the other cell lines remain within 0.8× of the control value. During these three weeks 10 compounds scored positive for the specific inhibition of the K-ras promoter, 19 scored as leads for the inhibition of the c-erbB2 promoter and 39 compounds inhibited nonspecifically. Compounds scoring as leads in the primary screen are repeated and then subjected to secondary analysis such as effects on the minigene transfectant phenotypes (see above).

TABLE 7

The Number (and %) of Compounds Scoring as Specific Repressors

| Cell Line | Number | % |
|---|---|---|
| K-ras | 10 | 0.4 |
| neu | 19 | 0.8 |
| CMV | 1 | .04 |
| Toxic | 39 | 1.7 |

Note: During the course of this screen 16 compounds (0.7%) specifically stimulated the transcriptional activity of the CMV promoter. TIR values for these compounds ranged from 2.0 to 15.5.

High-throughput screening of pure chemical or fermentation broth samples using a luciferase expression assay consistently leads to the discovery of lead samples with the potential to be developed into novel compounds for the modulation of promoters useful for the expression of recombinant proteins, or compounds useful for treating viral diseases.

REFERENCES

1. Goeddel, D. V., 1990, In: Methods in Enzymology, Vol. 185, D. V. Goeddel, ed., pg. 3
2. Mocarski, E., 1988, Genes Dev. 2(8):926
3. Molecular Cloning: A Laboratory Manual, 1989, J. Sambrook, E. F. Fritsch and T. Manaitis, eds, pg 165
4. DNA Tumor Viruses, 1981, J. Tooze, ed.
5. McKnight, S. and Tjian, R., 1986, Cell 46:795
6. Kaufman, R. J., 1990, In: Methods in Enzymology, Vol. 185, D. V. Goeddel, ed., pg. 487
7. Smith, G. E., et al, 1983, J. Virol 46:584
8. Smith, G. E., et al, 1983, Mol. Cell. Biol. 3:2156
9. Emr, S. D., 1990, In: Methods in Enzymology, Vol. 185 (Goeddel, D. V., ed), pg. 231.
10. Mylin, L. M. et al, 1990, In: Methods in Enzymology, Vol. 185 (Goeddel, D. V., ed), pg. 287.
11. Etcheverry, T., 1990, In: Methods in Enzymology, Vol. 185 (Goeddel, D. V., ed), pg. 319.
12. Price, V. L. et al, 1990, In: Methods in Enzymology, Vol. 185 (Goeddel, D. V., ed), pg. 38.
13. Beier, D. R. et al, 1986, Mol. Cell. Biol. 5:1743
14. Shuster, J. et al, 1986, Mol. Cell. Biol. 6:1894
15. Macaset, F. F. et al (1975) Am.J.Clin. Pathol.63:859.
16. Mintz, L. et al (1983) Amm.Intern.Med.99:326.
17. Richman, R. C. (1990) in Antiviral Agents and viral Diseases of Man, 3rd edition. Galasso, G. J., Whitley, R. J. and Merigan, T. C., eds pg 301.

18. zur Hausen, H. (1985) Prog.Med.Virol.32:15.
19. Andiman, W. et al (1983) J.Infect.Dis. 148:367; Jones, J. F. et al (1988) N.Engl.J.Med. 318:733.
20. De-The, G. (1982) in the Herpesvirus, Vol 1 (Roizman, B., ed) p25.
21. Leyeraz, S. et al (1985) N.Engl. J.Med. 312:1296.
22. Tiollais, P. et al (1985) Nature 317:489.
23. Shafritz, D. A. and Kew, M. C. (1981) Hepatology 1:1.
24. Richman, D. D. (1990) in Antiviral Agents and Viral Diseases of Man, 3rd edition (Galasso, G. J., Whiley, R. J. and Merigan, T. C., eds.) pg581.
25. Cooper, D. A. et al (1985) Lancet i:35.
26. Maniatis, T., Goodbourn, S. and Fischer, J. A. (1987) Regulation of inducible and tissue-specific gene expression, Science, 236:1237.
27. Yanofsky, C. and Crawford, I. P. The Tryptophan Operon. In *Escherichia coli* and *Salmonella typhimurium*: Cellular and Molecular Biology (F. C. Neidhardt, J. L. Ingraham, K. Brooks Low, B. Magasanik, M. Schaechter, eds.) Vol. 2, p. 1453.
28. Schlief, R. The L-Arabinose Operon. In *Escherichia coli* and *Salmonella typhimurium*: Cellular and Molecular Biology (F. C. Neidhardt, J. L. Ingraham, K. Brooks Low, B. Maga Sanik, M. Schaecter, eds.) Vol. 2, p. 1473.
29. McClure (1985) Ann. Rev. Biochem., 54:171.
30. Hoopes, B. C. and McClure, W. R. Strategies in Regulation of Transcription Initiation. In *Escherichia coli* and *Saµmonella Typhimurium*: Cellular and Molecular Biology (F. C. Neidhardt, J. L. Ingraham, K. Brooks Low, B. Magasanik, M. Schaechter, eds.) Vol. 2, p. 1231.
31. Matthews, B. W. (1987) Cro repressor structure and its interaction with DNA. In DNA: Protein Interactions and Gene Regulation (E. B. Thompson and J. Papaconstantinou, eds.) University of Texas Press, Austin.
32. Schlief, R. (1988) DNA binding by proteins, Science, 241:1182.
33. Evans, R. M. and Hollenberg, S. M. (1988) Zinc fingers: Gilt by association, Cell, 52:1.
34. Landschulz, W. H., Johnson, P. F., and McKnight, S. L. (1988). The leucine zipper: A hypothetical structure common to a new class of DNA binding proteins, Science, 240:1759.
35. Levine, M. and Hoey, T. (1988) Homeobox proteins as sequence-specific transcription factors, Cell, 55:537.
36. Krainer, A. R. and Maniatis, T. (1988) RNA splicing. In Transcription and Splicing (Hames, B. D. and Glover, D. M., eds.) IRL Press, Washington, D.C., Vol. 1.
37. Proudfoot, N. J. and Whitelaw, E. (1988) Termination and 3' end processing of eukaryotic RNA. In Transcription and Splicing (Hames, B. D. and Glover, D. M., eds.) ERL Press, Washington, D.C., Vol. 1, p. 97.
38. La Thangue, N. B. and Rigby, P. W. J. (1988) Transacting protein factors and the regulation and eukaryotic transcription. In Transcription and Splicing (Hames, B. D. and Glover, D. M., eds) IRL Press, Washington, D. C., Vol. 1.
39. Maniatis, T., Goodbourn, S. and Fischer, J. A. (1987) Regulation of inducible and tissue-specific gene expression, Science, 236:1237.
40. Yamamoto, K. R. (1985) Steroid receptor regulated transcription of specific genes and gene networks, Ann. Rev., Genet., 19:209.
41. Denison, M. S., Fisher, Springfield, N.J., J. M., and Whitlock, Jr., J. P. (1988) Inducible, receptor-dependent protein-DNA interactions at a dioxin-responsive transcriptional enhancer, Proc. Natl. Acad. Sci. USA, 85:2528.
42. Hoeffler, J. P., Meyer, T. E., Yun, Y., Jameson, J. L., and Habener, J. F. (1988) Cyclic AMP-responsive DNA-binding protein: Structure based on a cloned placental cDNA, Science, 242:1430.
43. Angel, P., Baumann, I., Stein, B., Delius, H., Rahmsdorf, H. J. and Herrlich, P. (1987) 12-0-tetradecanoyl-phorbol-13-acetate (TPA) induction of the human collagenase gene is mediated by an inducible enhancer element located in the 5'-flanking region. Mol. Cell. Biol., 7:2256.
44. Angel, P., Imagawa, M., Chiu, R. Stein, B., Imbra, R. J., Rahmsdorf, H. J., Jonat, C., Herrlich, P. and Karin, M. (1987) Phorbol ester-inducible genes contain a common cis element recognized by a TPA-modulated trans-acting factor, Cell 49:729.
45. Edeµman, A. M., Blumenthal, D. R. and Krebs, E. G. (1987) Protein Serine/Threonine Kinases Ann. Rev. 56:567–613.
46. Yamamoto, K. K., Gonzalez, G. A., Biggs III, W. H., and Montminy, M. R. (1988) Phosphorylation-induced binding and transcriptional efficacy of nuclear factor CREB, Nature, 334:494.
47. De Wet, J. R., Wood, K. V., Helinski, D. R., and DeLuca, M. (1985) Cloning of firefly luciferase cDNA and the expression of active luciferase in *Escherichia coli*, Proc. Natl. Acad. Sci. USA, 82:7870.
48. Engebrecht, J. M., Simon, M., and Silverman, M. (1985) Measuring gene expression with light. Science, 227:1345.
49. Bottenstein, J., Hayashi, I., Hutchings, S., Masui, H., Mather, J., McClure, D. B., Ohasa, S., Rizzino, A., Sato G., Serrero, G., Wolfe, R., and Wu, R. (1979) The growth of cells in serum-free hormone-supplemented media, Methods of Enzymology, 58:94.
50. Hayashi, I., Larner, J., and Sato, G. (1978) Hormonal growth control of cells in culture, In Vitro, 14:23.
51. Maniatis, T., Goodbourn, S. Fischer, J. A. (1987) Regulation of inducible and tissue-specific gene expression, Science, 236:1237.
52. Ow, D. W., Wood, K. U., Deluca, M., Dewet, J. R., Melinski, D., and Howell, S. H. Science 234:856–859.
53. McKnight, S. L. (1982) Functional relationships between transcriptional control signals of teh thymidine kinase gene of herpes simplex virus, Cell, 31:355.
54. Gorman, C., (185) Vectors used in mammalian cell expression. In DNA Cloning, Vol. II (D. M. Glover, ed). IRL Press, Washington, D.C.
55. Kadesch, T. and Berg, P. (1986) Effects of position of the simian virus 40 enhancer on expression of multiple transcription units in a single plasmid. Mol. Cell. Biol. 6:2593–2601.
56. Boshart, M., Weber, F., Jahan, G., Dorsch-Kasler, K., Fleckenstein, B. and Schaffner, W. (1985) A very strong enhancer is located upstream of a immediate early gene of human cytoomegalovirus. Cell 41:521–530.
57. Southern, E. (1980) Methods in Enzymology, 69:152.
58. Feinberg, A. and Vogelstein (1984) Anal, Biochem. 137:266.

What is claimed is:

1. A method of specifically transcriptionally modulating the expression of a gene encoding a viral protein, the expression of which gene is associated with a defined pathological effect within a multicellular organism, which comprises contacting a cell, which is capable of expressing the gene, with a concentration of a molecule effective to specifically transcriptionally modulate expression of the gene and thereby affect the level of the protein encoded by the gene which is expressed by the cell, wherein the molecule does not naturally occur in the cell, and specifically modulates transcription of the gene by:
        1) binding directly to the nucleotide sequence regulating transcription, or
        2) by binding directly to RNA produced by transcription from the gene of interest, or
        3) by binding directly to a protein regulating transcription of said gene, with the proviso that the molecule binds the protein at a site distinct from the normal ligand binding site if the protein is a receptor
    with the proviso that the molecule is not a nucleic acid molecule complementary to a sequence within the gene.

2. A method of claim 1, wherein the molecule does not naturally occur in any cell of a lower eucaryotic organism.

3. A method of claim 1, wherein the molecule does not naturally occur in any cell.

4. A method of claim 1, wherein the molecule is not a naturally occurring molecule.

5. A method of claim 1, wherein the cell is a cell of the multicellular organism.

6. A method of claim 1, wherein the cell is an insect cell.

7. A method of claim 1, wherein the cell is an animal cell.

8. A method of claim 7, wherein the animal cell is a human cell.

9. A method of claim 1, wherein the transcriptional modulation comprises upregulation of the expression of the gene.

10. A method of claim 1, wherein the transcriptional modulation comprises downregulation of the expression of the gene.

11. A method of claim 1, wherein the defined pathological effect is a disorder and modulation of the expression of the gene is associated with the amelioration of the disorder.

12. A method of claim 11, wherein the disorder is a viral infection.

13. A method of claim 12, wherein the viral infection is an hepatitis virus infection.

14. A method of claim 12, wherein the viral infection is an herpes virus infection.

15. A method of claim 14, wherein the viral infection is a cytomegalovirus infection.

16. A method of claim 12, wherein the viral infection is an HIV virus infection.

17. A method of claim 14, wherein the viral infection is an EBV virus infection.

18. A method of claim 12, wherein the viral infection is a papilloma virus infection.

19. A method of claim 11, wherein the disorder is cancer.

20. A method of claim 19, wherein the cancer is an hepatocellular carcinoma.

21. A method of claim 19, wherein the cancer is a leukemia.

22. A method of claim 19, wherein the cancer is a cervical carcinoma.

23. A method of claim 1, wherein the molecule binds to a modulatable transcriptional regulatory sequence of the gene.

\* \* \* \* \*

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 65 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

TCGACCCGGG CGGCCGCTGA TCAGACGTCG GGCCCGGTAC CGTGCACTAC GTAAGATCTA      60

AGCTT                                                                 65

(2) INFORMATION FOR SEQ ID NO:2:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

ACTAGTCTGC AGGCTAGCAC TCTTCTGGTC CCCACAGACT CAGAGAGAAC CCACCATGGA      60

(2) INFORMATION FOR SEQ ID NO:3:

(i) SEQUENCE CHARACTERISTICS:
       (A) LENGTH: 61 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

AGACGCCAAA AACATCAAGA AAGGCCCGGC GCCATTCTAT CCTCTAGAGG GGATCCAGCT      60

G                                                                     61

(2) INFORMATION FOR SEQ ID NO:4:

(i) SEQUENCE CHARACTERISTICS:
       (A) LENGTH: 56 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

TAGATCTTAC GTAGTGCACG GTACCGGGCC CGACGTCTGA TCAGCGGCCG CCCGGG          56

(2) INFORMATION FOR SEQ ID NO:5:

(i) SEQUENCE CHARACTERISTICS:
       (A) LENGTH: 59 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

GGTGGGTTCT CTCTGAGTCT GTGGGGACCA AAGAGTGCT AGCCTGCGAC TAGTAAGCT            59

(2) INFORMATION FOR SEQ ID NO:6:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

AATTCAGCTG GATCCCCTCT AGAGGATAGA ATGGCGCCGG GCCTTTCTTG ATGTTTTTGG           60

CGTCTTCCAT                                                                 70

(2) INFORMATION FOR SEQ ID NO:7:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GATCGGCCCC TAGGGCCGCG GCCGCAT                                              27

(2) INFORMATION FOR SEQ ID NO:8:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

ATGCGGCCGC GGCCCTAGGG GCC                                                  23

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

GATCGGCCCT AGGGGCGGCC GCAT                                                 24

(2) INFORMATION FOR SEQ ID NO:10:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

ATGCGGCCGC GGCCCCCTAG GGCC                                           24

(2) INFORMATION FOR SEQ ID NO:11:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGCTTGGCCC CTAGGGCCAC TAGTCTGCAG CTATGATGAC ACAAACCCCG CCCAGCGTCT    60

TGTCATTGGC GA                                                       72

(2) INFORMATION FOR SEQ ID NO:12:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TCGAATTCGC CAATGACAAG ACGCTGGGCG GGGTTTGTGT CATCATAGCT CAGACTAGTG    60

GCCCTAGGGG CCA                                                      73

(2) INFORMATION FOR SEQ ID NO:13:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

ATTCGAACAC GCAGATGCAG TCGGGGCGGC GCGGTCCGAG GTCCACTTCG CATATTAAGG    60

TGACGCGTGT GGG                                                      73

(2) INFORMATION FOR SEQ ID NO:14:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CTAGCCCACA CGCGTCACCT TAATATGCGA AGTGGACCTC GGACCGCGCC GCCCCGACTG    60

CATCTGCGTG T                                                        71

```
(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GATCGGCCCC TAGGGCCATT T                                              21

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AAATGGCCCT AGGGGCC                                                   17

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CATGGGGCCG AGCCGCAGT GAGCAC                                          26

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CATGGTGCTC ACTGCGGCTC CGGCCC                                         26

(2) INFORMATION FOR SEQ ID NO:19:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TCGAGATCTG AGGCCTGCTG ACCATGGGGG CC                                  32
```

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

CCCATGGTCA GCAGGCCTCA GATC        24